(12) United States Patent
Wardle et al.

(10) Patent No.: US 11,992,437 B2
(45) Date of Patent: *May 28, 2024

(54) OCULAR IMPLANTS FOR DELIVERY INTO AN ANTERIOR CHAMBER OF THE EYE

(71) Applicant: Alcon Inc., Fribourg (CH)

(72) Inventors: John Wardle, San Clemente, CA (US); Andrew T. Schieber, Tustin, CA (US)

(73) Assignee: Alcon Inc., Fribourg (CH)

( * ) Notice: Subject to any disclaimer, the term of this patent is extended or adjusted under 35 U.S.C. 154(b) by 476 days.

This patent is subject to a terminal disclaimer.

(21) Appl. No.: 17/314,699

(22) Filed: May 7, 2021

(65) Prior Publication Data

US 2021/0330499 A1 Oct. 28, 2021

Related U.S. Application Data

(60) Continuation of application No. 15/150,175, filed on May 9, 2016, now Pat. No. 11,026,836, which is a division of application No. 13/793,638, filed on Mar. 11, 2013, now Pat. No. 9,358,156.

(60) Provisional application No. 61/635,104, filed on Apr. 18, 2012.

(51) Int. Cl.
*A61F 9/007* (2006.01)
(52) U.S. Cl.
CPC ................ *A61F 9/00781* (2013.01)
(58) Field of Classification Search
CPC .................................................. A61F 9/00781
See application file for complete search history.

(56) References Cited

U.S. PATENT DOCUMENTS

| | | | |
|---|---|---|---|
| 703,296 | A | 6/1902 | Arnold |
| 1,601,709 | A | 10/1926 | Windom |
| 2,716,983 | A | 9/1955 | George et al. |
| 3,071,135 | A | 1/1963 | Baldwin et al. |
| 3,788,327 | A | 1/1974 | Donowitz et al. |
| 3,811,442 | A | 5/1974 | Maroth |
| 3,858,577 | A | 1/1975 | Bass et al. |
| 3,884,236 | A | 5/1975 | Krasnov |
| 3,948,271 | A | 4/1976 | Akiyama |
| 3,982,541 | A | 9/1976 | L'Esperance |

(Continued)

FOREIGN PATENT DOCUMENTS

| | | |
|---|---|---|
| AU | 1998/76197 B2 | 2/1999 |
| DE | 4226476 C1 | 8/1993 |

(Continued)

OTHER PUBLICATIONS

Bahler, et al.; Trabecular bypass stents decrease intraocular pressure in cultured human anterior segments; Amer. Journal of Ophthalmology; vol. 138, No. 6; pp. 988-994.e2; Dec. 2004.

(Continued)

*Primary Examiner* — Jessica Arble

(57) ABSTRACT

An ocular implant adapted to be disposed within Schlemm's canal of a human eye with a body extending along a curved longitudinal central axis in a curvature plane, a first strut on one side of the implant and a second strut on an opposite side of the implant, the circumferential extent of the first strut with respect to the plane of curvature being greater than the circumferential extent of the second strut with respect to the plane of curvature. The invention also includes methods of using the implant.

14 Claims, 30 Drawing Sheets

(56) References Cited

U.S. PATENT DOCUMENTS

| | | |
|---|---|---|
| 4,037,604 A | 7/1977 | Newkirk |
| 4,134,405 A | 1/1979 | Smit |
| 4,273,109 A | 6/1981 | Enderby |
| 4,391,275 A | 7/1983 | Fankhauser et al. |
| 4,428,746 A | 1/1984 | Mendez |
| 4,457,757 A | 7/1984 | Molteno |
| 4,461,294 A | 7/1984 | Baron |
| 4,470,407 A | 9/1984 | Hussein |
| 4,497,319 A | 2/1985 | Sekine et al. |
| 4,501,274 A | 2/1985 | Skjaerpe |
| 4,517,973 A | 5/1985 | Sunago et al. |
| 4,538,608 A | 9/1985 | L'Esperance |
| 4,548,205 A | 10/1985 | Armeniades et al. |
| 4,551,129 A | 11/1985 | Coleman et al. |
| 4,558,698 A | 12/1985 | O'Dell |
| 4,559,942 A | 12/1985 | Eisenberg |
| 4,566,438 A | 1/1986 | Liese et al. |
| 4,580,559 A | 4/1986 | L'Esperance |
| 4,583,539 A | 4/1986 | Karlin et al. |
| 4,601,713 A | 7/1986 | Fuquo |
| 4,604,087 A | 8/1986 | Joseph |
| 4,633,866 A | 1/1987 | Peyman et al. |
| 4,658,816 A | 4/1987 | Ector |
| 4,660,546 A | 4/1987 | Herrick et al. |
| 4,671,273 A | 6/1987 | Lindsey |
| 4,689,040 A | 8/1987 | Thompson |
| 4,699,140 A | 10/1987 | Holmes et al. |
| 4,706,669 A | 11/1987 | Schlegel |
| 4,722,350 A | 2/1988 | Armeniades et al. |
| 4,722,724 A | 2/1988 | Schocket |
| 4,729,373 A | 3/1988 | Peyman |
| 4,733,665 A | 3/1988 | Palmaz |
| 4,750,901 A | 6/1988 | Molteno |
| 4,770,654 A | 9/1988 | Rogers et al. |
| 4,791,927 A | 12/1988 | Menger |
| 4,826,478 A | 5/1989 | Schocket |
| 4,846,172 A | 7/1989 | Berlin |
| 4,861,341 A | 8/1989 | Woodburn |
| 4,876,250 A | 10/1989 | Clark |
| 4,880,000 A | 11/1989 | Holmes et al. |
| 4,886,488 A | 12/1989 | White |
| 4,919,130 A | 4/1990 | Stoy et al. |
| 4,925,299 A | 5/1990 | Meisberger et al. |
| 4,934,363 A | 6/1990 | Smith et al. |
| 4,934,809 A | 6/1990 | Volk |
| 4,936,825 A | 6/1990 | Ungerleider |
| 4,946,436 A | 8/1990 | Smith |
| 4,968,296 A | 11/1990 | Ritch et al. |
| 4,994,060 A | 2/1991 | Rink et al. |
| 5,034,010 A | 7/1991 | Kittrell et al. |
| 5,092,837 A | 3/1992 | Ritch et al. |
| 5,123,902 A | 6/1992 | Muller et al. |
| 5,127,901 A | 7/1992 | Odrich |
| 5,129,895 A | 7/1992 | Vassiliadis et al. |
| 5,178,604 A | 1/1993 | Baerveldt et al. |
| 5,180,362 A | 1/1993 | Worst |
| 5,190,552 A | 3/1993 | Kelman |
| 5,213,569 A | 5/1993 | Davis |
| 5,246,452 A | 9/1993 | Sinnott |
| 5,254,112 A | 10/1993 | Sinofsky et al. |
| 5,273,056 A | 12/1993 | McLaughlin et al. |
| 5,290,267 A | 3/1994 | Zimmermann |
| 5,300,020 A | 4/1994 | L'Esperance |
| 5,359,685 A | 10/1994 | Waynant et al. |
| 5,360,399 A | 11/1994 | Stegmann |
| 5,371,078 A | 12/1994 | Clark et al. |
| 5,372,577 A | 12/1994 | Ungerleider |
| 5,445,637 A | 8/1995 | Bretton |
| 5,454,796 A | 10/1995 | Krupin |
| 5,458,615 A | 10/1995 | Klemm et al. |
| 5,501,274 A | 3/1996 | Nguyen et al. |
| 5,536,259 A | 7/1996 | Utterberg |
| 5,575,780 A | 11/1996 | Saito |
| 5,591,223 A | 1/1997 | Lock et al. |
| 5,607,966 A | 3/1997 | Hellberg et al. |
| 5,613,972 A | 3/1997 | Lee et al. |
| 5,626,558 A | 5/1997 | Suson |
| 5,643,250 A | 7/1997 | O'Donnell |
| 5,653,753 A | 8/1997 | Brady et al. |
| 5,657,760 A | 8/1997 | Ying et al. |
| 5,676,669 A | 10/1997 | Colvard |
| 5,704,907 A | 1/1998 | Nordquist et al. |
| 5,713,844 A | 2/1998 | Peyman |
| 5,722,970 A | 3/1998 | Colvard et al. |
| 5,738,676 A | 4/1998 | Hammer et al. |
| 5,738,677 A | 4/1998 | Colvard et al. |
| 5,785,658 A | 7/1998 | Benaron et al. |
| 5,792,099 A | 8/1998 | DeCamp et al. |
| 5,792,103 A | 8/1998 | Schwartz et al. |
| 5,807,302 A | 9/1998 | Wandel |
| 5,811,453 A | 9/1998 | Yanni et al. |
| 5,865,831 A | 2/1999 | Cozean et al. |
| 5,868,697 A | 2/1999 | Richter et al. |
| 5,879,319 A | 3/1999 | Pynson et al. |
| 5,885,279 A | 3/1999 | Bretton |
| 5,893,837 A | 4/1999 | Eagles et al. |
| 5,895,831 A | 4/1999 | Brasier et al. |
| 5,919,171 A | 7/1999 | Kira et al. |
| 5,948,427 A | 9/1999 | Yamamoto et al. |
| 5,968,058 A | 10/1999 | Richter et al. |
| 5,984,963 A | 11/1999 | Ryan et al. |
| 5,990,099 A | 11/1999 | Clark |
| 5,993,438 A | 11/1999 | Juhasz et al. |
| 5,997,531 A | 12/1999 | Loeb et al. |
| 6,002,480 A | 12/1999 | Izatt et al. |
| 6,007,511 A | 12/1999 | Prywes |
| 6,050,970 A | 4/2000 | Baerveldt |
| 6,083,193 A | 7/2000 | Kadziauskas et al. |
| 6,099,521 A | 8/2000 | Shadduck |
| 6,102,045 A | 8/2000 | Nordquist et al. |
| 6,142,990 A | 11/2000 | Burk |
| 6,146,375 A | 11/2000 | Juhasz et al. |
| 6,177,544 B1 | 1/2001 | Kanal et al. |
| 6,186,974 B1 | 2/2001 | Allan et al. |
| 6,217,584 B1 | 4/2001 | Nun |
| 6,221,078 B1 | 4/2001 | Bylsma |
| 6,238,409 B1 | 5/2001 | Hojeibane |
| 6,241,721 B1 | 6/2001 | Cozean et al. |
| D444,874 S | 7/2001 | Haffner et al. |
| 6,297,228 B1 | 10/2001 | Clark |
| 6,319,274 B1 | 11/2001 | Shadduck |
| 6,328,747 B1 | 12/2001 | Nun |
| 6,375,642 B1 | 4/2002 | Grieshaber et al. |
| 6,398,809 B1 | 6/2002 | Hoffmann et al. |
| 6,409,752 B1 | 6/2002 | Boatman et al. |
| 6,450,984 B1 | 9/2002 | Lynch et al. |
| 6,464,724 B1 | 10/2002 | Lynch et al. |
| 6,471,666 B1 | 10/2002 | Odrich |
| 6,494,857 B1 | 12/2002 | Neuhann |
| 6,508,779 B1 | 1/2003 | Suson |
| 6,517,523 B1 | 2/2003 | Kaneko et al. |
| 6,524,275 B1 | 2/2003 | Lynch et al. |
| 6,533,764 B1 | 3/2003 | Haffner et al. |
| 6,533,768 B1 | 3/2003 | Hill |
| 6,544,208 B2 | 4/2003 | Ethier et al. |
| 6,544,249 B1 | 4/2003 | Yu et al. |
| 6,551,289 B1 | 4/2003 | Higuchi et al. |
| 6,626,858 B2 | 9/2003 | Lynch et al. |
| 6,638,239 B1 | 10/2003 | Bergheim et al. |
| 6,666,841 B2 | 12/2003 | Gharib et al. |
| 6,699,210 B2 | 3/2004 | Williams et al. |
| 6,699,211 B2 | 3/2004 | Savage |
| 6,702,790 B1 | 3/2004 | Ross |
| 6,726,676 B2 | 4/2004 | Stegmann et al. |
| D490,152 S | 5/2004 | Myall et al. |
| 6,730,056 B1 | 5/2004 | Ghaem et al. |
| 6,736,791 B1 | 5/2004 | Tu et al. |
| 6,780,164 B2 | 8/2004 | Bergheim et al. |
| 6,783,544 B2 | 8/2004 | Lynch et al. |
| 6,827,699 B2 | 12/2004 | Lynch et al. |
| 6,827,700 B2 | 12/2004 | Lynch et al. |
| 6,881,198 B2 | 4/2005 | Brown |
| 6,899,717 B2 | 5/2005 | Weber et al. |
| 6,939,298 B2 | 9/2005 | Brown et al. |

(56) References Cited

U.S. PATENT DOCUMENTS

| | | |
|---|---|---|
| 6,955,656 B2 | 10/2005 | Bergheim et al. |
| 6,962,573 B1 | 11/2005 | Wilcox |
| 6,981,958 B1 | 1/2006 | Gharib et al. |
| 6,989,007 B2 | 1/2006 | Shadduck |
| 7,018,376 B2 | 3/2006 | Webb et al. |
| 7,094,225 B2 | 8/2006 | Tu et al. |
| 7,125,119 B2 | 10/2006 | Farberov |
| 7,133,137 B2 | 11/2006 | Shimmick |
| 7,135,009 B2 | 11/2006 | Tu et al. |
| 7,147,650 B2 | 12/2006 | Lee |
| 7,163,543 B2 | 1/2007 | Smedley et al. |
| 7,186,232 B1 | 3/2007 | Smedley et al. |
| 7,192,412 B1 | 3/2007 | Zhou et al. |
| 7,207,965 B2 | 4/2007 | Simon |
| 7,207,980 B2 | 4/2007 | Christian et al. |
| 7,220,238 B2 | 5/2007 | Lynch et al. |
| 7,273,475 B2 | 9/2007 | Tu et al. |
| 7,297,130 B2 | 11/2007 | Bergheim et al. |
| 7,331,984 B2 | 2/2008 | Tu et al. |
| 7,488,303 B1 | 2/2009 | Haffner et al. |
| 7,699,882 B2 | 4/2010 | Stamper et al. |
| 7,740,604 B2 | 6/2010 | Schieber et al. |
| 7,931,596 B2 | 4/2011 | Rachlin et al. |
| 7,967,772 B2 | 6/2011 | McKenzie et al. |
| 8,012,115 B2 | 9/2011 | Karageozian |
| 8,123,729 B2 | 2/2012 | Yamamoto et al. |
| 8,172,899 B2 | 5/2012 | Silvestrini et al. |
| 8,267,882 B2 | 9/2012 | Euteneuer et al. |
| 8,282,592 B2 | 10/2012 | Schieber et al. |
| 8,308,701 B2 | 11/2012 | Horvath et al. |
| 8,337,509 B2 | 12/2012 | Schieber et al. |
| 8,372,026 B2 | 2/2013 | Schieber et al. |
| 8,414,518 B2 | 4/2013 | Schieber et al. |
| 8,425,449 B2 | 4/2013 | Wardle et al. |
| 8,475,374 B2 | 7/2013 | Irazoqui et al. |
| 8,512,404 B2 | 8/2013 | Frion et al. |
| 8,529,494 B2 | 9/2013 | Euteneuer et al. |
| 8,540,659 B2 | 9/2013 | Berlin |
| 8,551,166 B2 | 10/2013 | Schieber et al. |
| 8,629,161 B2 | 1/2014 | Mizuno et al. |
| 8,636,647 B2 | 1/2014 | Silvestrini et al. |
| 8,647,659 B2 | 2/2014 | Robinson et al. |
| 8,657,776 B2 | 2/2014 | Wardle et al. |
| 8,663,150 B2 | 3/2014 | Wardle et al. |
| 8,663,303 B2 | 3/2014 | Horvath et al. |
| 8,734,377 B2 | 5/2014 | Schieber et al. |
| 8,808,222 B2 | 8/2014 | Schieber et al. |
| 8,939,906 B2 | 1/2015 | Huang et al. |
| 8,939,948 B2 | 1/2015 | De Juan, Jr. et al. |
| 8,945,038 B2 | 2/2015 | Yablonski |
| 8,951,221 B2 | 2/2015 | Stegmann et al. |
| 8,961,447 B2 | 2/2015 | Schieber et al. |
| 8,974,511 B2 | 3/2015 | Horvath et al. |
| 9,039,650 B2 | 5/2015 | Schieber et al. |
| 9,050,169 B2 | 6/2015 | Schieber et al. |
| 9,066,750 B2 | 6/2015 | Wardle et al. |
| 9,066,783 B2 | 6/2015 | Euteneuer et al. |
| 9,155,655 B2 | 10/2015 | Schieber et al. |
| 9,211,213 B2 | 12/2015 | Wardle et al. |
| 9,226,852 B2 | 1/2016 | Schieber et al. |
| 9,301,875 B2 | 4/2016 | Tu et al. |
| 9,351,874 B2 | 5/2016 | Schieber et al. |
| 9,358,156 B2 * | 6/2016 | Wardle ............... A61F 9/00781 |
| 9,402,767 B2 | 8/2016 | Schieber et al. |
| 9,510,973 B2 | 12/2016 | Wardle |
| 9,579,234 B2 | 2/2017 | Wardle et al. |
| 9,603,741 B2 | 3/2017 | Berlin |
| 9,610,196 B2 | 4/2017 | Schieber et al. |
| 9,636,254 B2 | 5/2017 | Yu et al. |
| 9,642,746 B2 | 5/2017 | Berlin |
| 9,693,899 B2 | 7/2017 | Wardle et al. |
| 9,693,901 B2 | 7/2017 | Horvath et al. |
| 9,693,902 B2 | 7/2017 | Euteneuer et al. |
| 9,730,638 B2 | 8/2017 | Haffner et al. |
| 9,757,276 B2 | 9/2017 | Penhasi |
| 9,775,729 B2 | 10/2017 | McClain et al. |
| 9,782,293 B2 | 10/2017 | Doci |
| 9,820,883 B2 | 11/2017 | Berlin |
| 9,833,357 B2 | 12/2017 | Berlin |
| 9,931,243 B2 | 4/2018 | Wardle et al. |
| 10,159,601 B2 | 12/2018 | Berlin |
| 10,335,314 B2 | 7/2019 | Berlin |
| 10,363,168 B2 | 7/2019 | Schieber et al. |
| 10,390,993 B1 | 8/2019 | Berlin |
| 10,406,025 B2 | 9/2019 | Wardle et al. |
| 10,492,949 B2 | 12/2019 | Wardle et al. |
| 10,537,474 B2 | 1/2020 | Euteneuer et al. |
| 10,617,558 B2 | 4/2020 | Schieber et al. |
| 10,687,978 B2 | 6/2020 | Berlin |
| 10,709,547 B2 | 7/2020 | Schieber |
| 11,026,836 B2 | 6/2021 | Wardle et al. |
| 2001/0002438 A1 | 5/2001 | Sepetka et al. |
| 2001/0021835 A1 | 9/2001 | Mitchell et al. |
| 2002/0003546 A1 | 1/2002 | Mochimaru et al. |
| 2002/0013546 A1 | 1/2002 | Grieshaber et al. |
| 2002/0013572 A1 | 1/2002 | Berlin |
| 2002/0052653 A1 | 5/2002 | Durgin |
| 2002/0072673 A1 | 6/2002 | Yamamoto et al. |
| 2002/0082591 A1 | 6/2002 | Haefliger |
| 2002/0133168 A1 | 9/2002 | Smedley et al. |
| 2002/0143284 A1 | 10/2002 | Tu et al. |
| 2002/0165504 A1 | 11/2002 | Sharp et al. |
| 2002/0165522 A1 | 11/2002 | Holmen |
| 2002/0193805 A1 | 12/2002 | Ott et al. |
| 2003/0004457 A1 | 1/2003 | Andersson |
| 2003/0014092 A1 | 1/2003 | Neuhann |
| 2003/0040754 A1 | 2/2003 | Mitchell et al. |
| 2003/0055372 A1 | 3/2003 | Lynch et al. |
| 2003/0060748 A1 | 3/2003 | Baikoff |
| 2003/0060752 A1 | 3/2003 | Bergheim et al. |
| 2003/0060784 A1 | 3/2003 | Hilgers et al. |
| 2003/0093084 A1 | 5/2003 | Nissan et al. |
| 2003/0097151 A1 | 5/2003 | Smedley et al. |
| 2003/0105456 A1 | 6/2003 | Lin |
| 2003/0125351 A1 | 7/2003 | Azuma et al. |
| 2003/0175324 A1 | 9/2003 | Robinson et al. |
| 2003/0181848 A1 | 9/2003 | Bergheim et al. |
| 2003/0187384 A1 | 10/2003 | Bergheim et al. |
| 2003/0212387 A1 | 11/2003 | Kurtz et al. |
| 2003/0229303 A1 | 12/2003 | Haffner et al. |
| 2003/0236483 A1 | 12/2003 | Ren |
| 2003/0236484 A1 | 12/2003 | Lynch et al. |
| 2004/0024345 A1 | 2/2004 | Gharib et al. |
| 2004/0024453 A1 | 2/2004 | Castillejos |
| 2004/0030302 A1 | 2/2004 | Kamata et al. |
| 2004/0070761 A1 | 4/2004 | Horvath et al. |
| 2004/0082939 A1 | 4/2004 | Berlin |
| 2004/0088048 A1 | 5/2004 | Richter et al. |
| 2004/0092856 A1 | 5/2004 | Dahan |
| 2004/0098124 A1 | 5/2004 | Freeman et al. |
| 2004/0102729 A1 | 5/2004 | Haffner et al. |
| 2004/0106975 A1 | 6/2004 | Solovay et al. |
| 2004/0111050 A1 | 6/2004 | Smedley et al. |
| 2004/0116909 A1 | 6/2004 | Neuberger et al. |
| 2004/0122380 A1 | 6/2004 | Utterberg |
| 2004/0127843 A1 | 7/2004 | Tu et al. |
| 2004/0147870 A1 | 7/2004 | Burns et al. |
| 2004/0193095 A1 | 9/2004 | Shadduck |
| 2004/0193262 A1 | 9/2004 | Shadduck |
| 2004/0199149 A1 | 10/2004 | Myers et al. |
| 2004/0199171 A1 | 10/2004 | Akahoshi |
| 2004/0210185 A1 | 10/2004 | Tu et al. |
| 2004/0210501 A1 | 10/2004 | Vass et al. |
| 2004/0216749 A1 | 11/2004 | Tu |
| 2004/0225357 A1 | 11/2004 | Worst et al. |
| 2004/0228013 A1 | 11/2004 | Goldstein et al. |
| 2004/0249333 A1 | 12/2004 | Bergheim et al. |
| 2004/0254517 A1 | 12/2004 | Quiroz-Mercado et al. |
| 2004/0254519 A1 | 12/2004 | Tu et al. |
| 2004/0254520 A1 | 12/2004 | Porteous et al. |
| 2004/0260228 A1 | 12/2004 | Lynch et al. |
| 2005/0041200 A1 | 2/2005 | Rich |
| 2005/0043722 A1 | 2/2005 | Lin |
| 2005/0049578 A1 | 3/2005 | Tu et al. |

(56) References Cited

U.S. PATENT DOCUMENTS

| | | |
|---|---|---|
| 2005/0090806 A1 | 4/2005 | Lynch et al. |
| 2005/0090807 A1 | 4/2005 | Lynch et al. |
| 2005/0101967 A1 | 5/2005 | Weber et al. |
| 2005/0107734 A1 | 5/2005 | Coroneo |
| 2005/0119601 A9 | 6/2005 | Lynch et al. |
| 2005/0119636 A1 | 6/2005 | Haffner et al. |
| 2005/0125003 A1 | 6/2005 | Pinchuk et al. |
| 2005/0131514 A1 | 6/2005 | Hijlkema et al. |
| 2005/0149114 A1 | 7/2005 | Cartledge et al. |
| 2005/0154443 A1 | 7/2005 | Linder et al. |
| 2005/0165385 A1 | 7/2005 | Simon |
| 2005/0192527 A1 | 9/2005 | Gharib et al. |
| 2005/0197667 A1 | 9/2005 | Chan et al. |
| 2005/0203542 A1 | 9/2005 | Weber et al. |
| 2005/0209549 A1 | 9/2005 | Bergheim et al. |
| 2005/0209550 A1 | 9/2005 | Bergheim et al. |
| 2005/0240168 A1 | 10/2005 | Neuberger et al. |
| 2005/0244464 A1 | 11/2005 | Hughes |
| 2005/0245916 A1 | 11/2005 | Connor |
| 2005/0250788 A1 | 11/2005 | Tu et al. |
| 2005/0260186 A1 | 11/2005 | Bookbinder et al. |
| 2005/0266047 A1 | 12/2005 | Tu et al. |
| 2005/0271704 A1 | 12/2005 | Tu et al. |
| 2005/0273033 A1 | 12/2005 | Grahn et al. |
| 2005/0277864 A1 | 12/2005 | Haffner et al. |
| 2005/0279369 A1 | 12/2005 | Lin |
| 2005/0288619 A1 | 12/2005 | Gharib et al. |
| 2005/0288745 A1 | 12/2005 | Andersen et al. |
| 2006/0020247 A1 | 1/2006 | Kagan et al. |
| 2006/0021623 A1 | 2/2006 | Miller et al. |
| 2006/0032507 A1 | 2/2006 | Tu |
| 2006/0052879 A1 | 3/2006 | Kolb |
| 2006/0069340 A1 | 3/2006 | Simon |
| 2006/0074375 A1 | 4/2006 | Bergheim et al. |
| 2006/0079828 A1 | 4/2006 | Brown |
| 2006/0084907 A1 | 4/2006 | Bergheim et al. |
| 2006/0084954 A1 | 4/2006 | Zadoyan et al. |
| 2006/0106370 A1 | 5/2006 | Baerveldt et al. |
| 2006/0110428 A1 | 5/2006 | deJuan et al. |
| 2006/0116626 A1 | 6/2006 | Smedley et al. |
| 2006/0129141 A1 | 6/2006 | Lin |
| 2006/0149194 A1 | 7/2006 | Conston et al. |
| 2006/0154981 A1 | 7/2006 | Klimko et al. |
| 2006/0155238 A1 | 7/2006 | Shields |
| 2006/0155265 A1 | 7/2006 | Juhasz et al. |
| 2006/0155300 A1 | 7/2006 | Stamper et al. |
| 2006/0167421 A1 | 7/2006 | Quinn |
| 2006/0167466 A1 | 7/2006 | Dusek |
| 2006/0173397 A1 | 8/2006 | Tu et al. |
| 2006/0173399 A1 | 8/2006 | Rodgers et al. |
| 2006/0178674 A1 | 8/2006 | McIntyre |
| 2006/0189915 A1 | 8/2006 | Camras et al. |
| 2006/0189916 A1 | 8/2006 | Bas et al. |
| 2006/0189917 A1 | 8/2006 | Mayr et al. |
| 2006/0195055 A1 | 8/2006 | Bergheim et al. |
| 2006/0195056 A1 | 8/2006 | Bergheim et al. |
| 2006/0195187 A1 | 8/2006 | Stegmann et al. |
| 2006/0200113 A1 | 9/2006 | Haffner et al. |
| 2006/0224146 A1 | 10/2006 | Lin |
| 2006/0241749 A1 | 10/2006 | Tu et al. |
| 2006/0259021 A1 | 11/2006 | Lin |
| 2006/0264971 A1 | 11/2006 | Akahoshi |
| 2006/0276759 A1 | 12/2006 | Kinast et al. |
| 2007/0010827 A1 | 1/2007 | Tu et al. |
| 2007/0021725 A1 | 1/2007 | Villette |
| 2007/0027452 A1 | 2/2007 | Varner et al. |
| 2007/0073275 A1 | 3/2007 | Conston et al. |
| 2007/0088432 A1 | 4/2007 | Solovay et al. |
| 2007/0093794 A1 | 4/2007 | Wang et al. |
| 2007/0093796 A1 | 4/2007 | Raksi et al. |
| 2007/0106200 A1 | 5/2007 | Levy |
| 2007/0106236 A1 | 5/2007 | Coroneo |
| 2007/0112292 A1 | 5/2007 | Tu et al. |
| 2007/0118147 A1 | 5/2007 | Smedley et al. |
| 2007/0121120 A1 | 5/2007 | Schachar |
| 2007/0135681 A1 | 6/2007 | Chin et al. |
| 2007/0173791 A1 | 7/2007 | Raksi |
| 2007/0179520 A1 | 8/2007 | West |
| 2007/0191863 A1 | 8/2007 | De Juan, Jr. et al. |
| 2007/0202186 A1 | 8/2007 | Yamamoto et al. |
| 2007/0208325 A1 | 9/2007 | Kurtz |
| 2007/0219509 A1 | 9/2007 | Tashiro et al. |
| 2007/0219541 A1 | 9/2007 | Kurtz |
| 2007/0235543 A1 | 10/2007 | Zadoyan et al. |
| 2007/0236771 A1 | 10/2007 | Zadoyan et al. |
| 2007/0265582 A1 | 11/2007 | Kaplan et al. |
| 2007/0270945 A1 | 11/2007 | Kobayashi et al. |
| 2007/0276315 A1 | 11/2007 | Haffner et al. |
| 2007/0276316 A1 | 11/2007 | Haffner et al. |
| 2007/0282244 A1 | 12/2007 | Tu et al. |
| 2007/0282245 A1 | 12/2007 | Tu et al. |
| 2007/0293807 A1 | 12/2007 | Lynch et al. |
| 2007/0293872 A1 | 12/2007 | Peyman |
| 2007/0298068 A1 | 12/2007 | Badawi et al. |
| 2008/0015488 A1 | 1/2008 | Tu et al. |
| 2008/0027519 A1 | 1/2008 | Guerrero |
| 2008/0045878 A1 | 2/2008 | Bergheim et al. |
| 2008/0058704 A1 | 3/2008 | Hee et al. |
| 2008/0058777 A1 | 3/2008 | Kurtz et al. |
| 2008/0082088 A1 | 4/2008 | Kurtz et al. |
| 2008/0091224 A1 | 4/2008 | Griffis et al. |
| 2008/0119827 A1 | 5/2008 | Kurtz et al. |
| 2008/0228127 A1 | 9/2008 | Burns et al. |
| 2008/0278687 A1 | 11/2008 | Somani |
| 2008/0288082 A1 | 11/2008 | Deal |
| 2008/0312661 A1 | 12/2008 | Downer et al. |
| 2009/0005852 A1 | 1/2009 | Gittings et al. |
| 2009/0028953 A1 | 1/2009 | Yamamoto et al. |
| 2009/0030363 A1 | 1/2009 | Gellman |
| 2009/0030381 A1 | 1/2009 | Lind et al. |
| 2009/0036843 A1 | 2/2009 | Erskine |
| 2009/0043321 A1 | 2/2009 | Conston et al. |
| 2009/0054723 A1 | 2/2009 | Khairkhahan et al. |
| 2009/0069786 A1 | 3/2009 | Vesely et al. |
| 2009/0082860 A1* | 3/2009 | Schieber .................. A61F 2/14 623/4.1 |
| 2009/0082862 A1 | 3/2009 | Schieber et al. |
| 2009/0104248 A1 | 4/2009 | Rapacki et al. |
| 2009/0118716 A1 | 5/2009 | Brownell |
| 2009/0118717 A1 | 5/2009 | Brownell et al. |
| 2009/0118718 A1 | 5/2009 | Raksi et al. |
| 2009/0131921 A1 | 5/2009 | Kurtz et al. |
| 2009/0132040 A1* | 5/2009 | Frion .................. A61F 9/00781 623/6.12 |
| 2009/0137988 A1 | 5/2009 | Kurtz |
| 2009/0138081 A1 | 5/2009 | Bergheim et al. |
| 2009/0157062 A1 | 6/2009 | Hauger et al. |
| 2009/0171327 A1 | 7/2009 | Kurtz et al. |
| 2009/0182421 A1 | 7/2009 | Silvestrini et al. |
| 2009/0198248 A1 | 8/2009 | Yeung et al. |
| 2009/0204053 A1 | 8/2009 | Nissan et al. |
| 2009/0247955 A1 | 10/2009 | Yamamoto et al. |
| 2009/0259126 A1 | 10/2009 | Saal et al. |
| 2009/0281520 A1 | 11/2009 | Highley et al. |
| 2009/0281530 A1 | 11/2009 | Korn |
| 2009/0291423 A1 | 11/2009 | Hara |
| 2010/0004580 A1 | 1/2010 | Lynch et al. |
| 2010/0036488 A1 | 2/2010 | de Juan et al. |
| 2010/0057072 A1 | 3/2010 | Roman et al. |
| 2010/0114309 A1 | 5/2010 | de Juan et al. |
| 2010/0137981 A1 | 6/2010 | Silvestrini et al. |
| 2010/0173866 A1 | 7/2010 | Hee et al. |
| 2010/0191176 A1 | 7/2010 | Ho et al. |
| 2010/0191177 A1 | 7/2010 | Chang et al. |
| 2010/0234726 A1 | 9/2010 | Sirimanne et al. |
| 2010/0234790 A1 | 9/2010 | Tu et al. |
| 2010/0262174 A1 | 10/2010 | Sretavan et al. |
| 2010/0324543 A1 | 12/2010 | Kurtz et al. |
| 2010/0331858 A1 | 12/2010 | Simaan et al. |
| 2011/0009958 A1* | 1/2011 | Wardle .................. A61F 9/0017 623/4.1 |
| 2011/0028948 A1 | 2/2011 | Raksi et al. |
| 2011/0028949 A1 | 2/2011 | Raksi et al. |
| 2011/0028950 A1 | 2/2011 | Raksi et al. |

(56) References Cited

U.S. PATENT DOCUMENTS

| | | |
|---|---|---|
| 2011/0028951 A1 | 2/2011 | Raksi et al. |
| 2011/0028952 A1 | 2/2011 | Raksi et al. |
| 2011/0028953 A1 | 2/2011 | Raksi et al. |
| 2011/0028954 A1 | 2/2011 | Raksi et al. |
| 2011/0028955 A1 | 2/2011 | Raksi |
| 2011/0028957 A1 | 2/2011 | Raksi et al. |
| 2011/0028958 A1 | 2/2011 | Raksi et al. |
| 2011/0098809 A1 | 4/2011 | Wardle et al. |
| 2011/0196487 A1 | 8/2011 | Badawi et al. |
| 2011/0218523 A1 | 9/2011 | Robl |
| 2011/0224597 A1 | 9/2011 | Stegmann et al. |
| 2012/0010702 A1 | 1/2012 | Stegmann et al. |
| 2012/0021397 A1 | 1/2012 | Van Dalen et al. |
| 2012/0022424 A1 | 1/2012 | Yamamoto et al. |
| 2012/0035524 A1 | 2/2012 | Silvestrini |
| 2012/0191064 A1 | 7/2012 | Conston et al. |
| 2012/0271272 A1 | 10/2012 | Hammack et al. |
| 2012/0283557 A1 | 11/2012 | Berlin |
| 2012/0302861 A1 | 11/2012 | Marshall et al. |
| 2013/0023837 A1 | 1/2013 | Becker |
| 2013/0182223 A1 | 7/2013 | Wardle et al. |
| 2013/0184631 A1 | 7/2013 | Pinchuk |
| 2013/0253402 A1 | 9/2013 | Badawi et al. |
| 2013/0253403 A1 | 9/2013 | Badawi et al. |
| 2013/0253437 A1 | 9/2013 | Badawi et al. |
| 2013/0253438 A1 | 9/2013 | Badawi et al. |
| 2013/0253528 A1 | 9/2013 | Haffner et al. |
| 2013/0267887 A1 | 10/2013 | Kahook et al. |
| 2013/0281908 A1 | 10/2013 | Schaller et al. |
| 2014/0018720 A1 | 1/2014 | Horvath et al. |
| 2014/0066821 A1 | 3/2014 | Freidland et al. |
| 2014/0066831 A1 | 3/2014 | Silvestrini et al. |
| 2014/0081195 A1 | 3/2014 | Clauson et al. |
| 2015/0018746 A1 | 1/2015 | Hattenbach |
| 2015/0022780 A1 | 1/2015 | John et al. |
| 2015/0038893 A1 | 2/2015 | Haffner et al. |
| 2015/0045714 A1 | 2/2015 | Horvath et al. |
| 2015/0057591 A1 | 2/2015 | Horvath et al. |
| 2015/0065940 A1 | 3/2015 | Rangel-Friedman et al. |
| 2015/0290033 A1 | 10/2015 | Wardle et al. |
| 2015/0305939 A1 | 10/2015 | Vera et al. |
| 2015/0305940 A1 | 10/2015 | Vera et al. |
| 2015/0313759 A1 | 11/2015 | Vera et al. |
| 2017/0143541 A1 | 5/2017 | Badawi et al. |
| 2017/0172794 A1 | 6/2017 | Varner et al. |
| 2017/0172795 A1 | 6/2017 | Lemer |
| 2017/0172799 A1 | 6/2017 | Horvath |
| 2017/0172800 A1 | 6/2017 | Romoda et al. |
| 2017/0202708 A1 | 7/2017 | Berlin |
| 2017/0239272 A1 | 8/2017 | Ambati et al. |
| 2017/0281409 A1 | 10/2017 | Haffner et al. |
| 2017/0360609 A9 | 12/2017 | Schieber et al. |
| 2018/0369017 A1 | 12/2018 | Schieber et al. |
| 2019/0076296 A1 | 3/2019 | Van Meter et al. |
| 2019/0343679 A1 | 11/2019 | Wardle et al. |
| 2019/0380874 A1 | 12/2019 | Schieber et al. |
| 2020/0060876 A1 | 2/2020 | Wardle et al. |
| 2020/0085620 A1 | 3/2020 | Euteneuer |
| 2020/0197221 A1 | 6/2020 | Schieber et al. |
| 2020/0222238 A1 | 7/2020 | Schieber et al. |
| 2020/0261270 A1 | 8/2020 | Berlin |
| 2021/0030590 A1 | 2/2021 | Blanda et al. |
| 2021/0361479 A1 | 11/2021 | Wardle et al. |
| 2022/0054314 A1 | 2/2022 | Van Meter et al. |
| 2022/0096271 A1 | 3/2022 | Wardle et al. |

FOREIGN PATENT DOCUMENTS

| | | |
|---|---|---|
| DE | 102012221350 A1 | 5/2014 |
| EP | 0168201 B1 | 6/1988 |
| EP | 0957949 A1 | 11/1996 |
| EP | 0766544 B1 | 5/1998 |
| EP | 1615604 B1 | 8/2009 |
| EP | 2193821 A1 | 6/2010 |
| EP | 1715827 B1 | 12/2010 |
| EP | 2380622 A1 | 10/2011 |
| EP | 2468327 A1 | 6/2012 |
| EP | 2471563 A1 | 7/2012 |
| EP | 1833440 B1 | 8/2012 |
| EP | 1732484 B1 | 8/2017 |
| EP | 1740153 B2 | 8/2017 |
| EP | 3205333 A1 | 8/2017 |
| JP | 10504978 A | 5/1998 |
| JP | 11123205 A | 5/1999 |
| JP | 2002542872 A | 12/2002 |
| JP | 2006517848 A | 8/2006 |
| JP | 2006289075 A | 10/2006 |
| JP | 2009523545 A | 6/2009 |
| JP | 2010509003 A | 3/2010 |
| JP | 2011502649 A | 1/2011 |
| JP | 2012527318 A | 11/2012 |
| JP | 2015517836 A | 6/2015 |
| WO | WO96/20742 A1 | 7/1996 |
| WO | WO99/01063 A1 | 1/1999 |
| WO | WO99/45868 A1 | 9/1999 |
| WO | WO00/07525 A1 | 2/2000 |
| WO | WO00/64389 A1 | 11/2000 |
| WO | WO00/64393 A1 | 11/2000 |
| WO | WO00/67687 A1 | 11/2000 |
| WO | WO01/89437 A2 | 11/2001 |
| WO | WO01/97727 A1 | 12/2001 |
| WO | WO02/36052 A1 | 5/2002 |
| WO | WO02/074052 A2 | 9/2002 |
| WO | WO02/080811 A2 | 10/2002 |
| WO | WO03/015659 A2 | 2/2003 |
| WO | WO03/045290 A1 | 6/2003 |
| WO | WO2004/054643 A1 | 7/2004 |
| WO | WO2004/093761 A1 | 11/2004 |
| WO | WO2005/105197 A2 | 11/2005 |
| WO | WO2006/066103 A2 | 6/2006 |
| WO | WO2007/035356 A2 | 3/2007 |
| WO | WO2007/047744 A2 | 4/2007 |
| WO | WO2007/087061 A2 | 8/2007 |
| WO | WO2008/002377 A1 | 1/2008 |
| WO | WO2008/005873 A2 | 1/2008 |
| WO | WO2009/120960 A2 | 10/2009 |
| WO | WO2011/053512 A1 | 5/2011 |
| WO | WO2011/057283 A1 | 5/2011 |
| WO | WO2011/106781 A1 | 9/2011 |
| WO | WO2011/150045 A1 | 12/2011 |
| WO | WO2012/051575 A2 | 4/2012 |
| WO | WO2012/083143 A1 | 6/2012 |
| WO | WO2013/147978 A2 | 10/2013 |

OTHER PUBLICATIONS

Cambridge Dictionary; Sensor (definition); 2 pages; retrived from the internet (http://dictionary.cambridge.org/define.asp?dict=CALD &key=71811 >) on Aug. 14, 2018.

Camras et al.; A novel schlemm's canal scaffold increases outflow facility in a human anterior segment perfusion model; Invest. Opthalmol. Vis. Sci. ; 53(10); pp. 6115-6121; Sep. 1, 2012.

D'Ermo, et al.; Our results with the operation of ab externo trabeculotomy; Ophthalmologica; vol. 163; pp. 347-355; Feb. 1971.

Dietlein et al.; Morphological variability of the trabecular meshwork in glaucoma patients: implications for non-perforating glaucoma surgery; British Journal of Ophthalmology; 84(12); pp. 1354-1359; Dec. 2000.

Ellingsen et al.; Trabeculotomy and sinusotomy in enucleated human eyes; Investigative Ophthalmology; vol. 11; pp. 21-28; Jan. 1972.

Grant; Experimental aqueous perfusion in enucleated human eyes; Archives of Ophthalmology; vol. 69; pp. 783-801; Jun. 1963.

Gulati et al; A novel 8-mm schlemm's canal scaffold reduces outflow resistance in a human anterior segment perfusion model; Invest. Ophthalmol. Vis. Sci.; 54(3); pp. 1698-1704; Mar. 5, 2013.

Huang et al.; Optical coherence tomography; Science; 254(5035); pp. 1178-1181; 12 pages (Author Manuscript); Nov. 1991.

Johnstone et al.; "Microsurgery of Schlemm's Canal and the Human Aqueous Outflow System;" American Journal of Ophthalmology, vol. 76 (6): 906-917; Dec. 1973.

(56) References Cited

OTHER PUBLICATIONS

Johnstone; Aqueous humor outflow system overview; Becker-Shaffer's Diagnosis and Therapy of the Glaucomas; Part 2 Aqueous Humor Dynamics; Chapter 3; pp. 25-46; Mosby Elseveir; (year of pub. sufficiently earlier than effective US filing date and any foreign priority date) 2009.
Kirkness et al.; The Use of Silicone Drainage Tubing to Control Post-Keratoplasty Glaucoma; Eye; 2 (pt 5); pp. 583-590; Apr. 1988.
Lee et al.; Aqueous-venous shunt and intraocular pressure. Preliminary report of animal studies; Investigative Ophthalmology; vol. 5; No. 1; pp. 59-64; Feb. 1966 .
Lee et al.; Short-pulsed neodymium-YAG laser trabeculotomy. An in vivo morphological study in the human eye; Investigative Ophthalmology and Visual Science; 29(11); pp. 1698-1707; Nov. 1988.
Lynch, Mary G.; U.S. Appl. No. 60/131,030 entitled "Devices and methods for treating glaucoma by enhancing aqueous outflow through schlemm's canal and anterior chamber angle," filed Apr. 26, 1999.
Macmilla Online Dictionary; Detector (definition); Macmilla On Line Dictionary; 2 pages; retrived from the internet (https://www.macmillandictionary.com/dictionary/british/detector) on Aug. 14, 2018.
Mäepea et al.; The pressures in the episcleral veins, schlemm's canal and the trabecular meshwork in monkeys: effects of changes in intraocular pressure; Exp. Eye Res.; vol. 49; pp. 645-663; Oct. 1989.
Molteno et al., Long Tube Implants in the Management of Glaucoma; SA Medical Journal; 26; pp. 1062-1066; Jun. 1976.
Molteno; New implant for drainage in glaucoma; Brit. J. Ophthal; 53; pp. 606-615; Sep. 1969.
Moses, Robert; The effect of intraocular pressure on resistance to outflow; Survey of Ophthalmology; vol. 22; No. 2; pp. 88-100; Sep.-Oct. 1977.
Nakamura et al.; Femtosecond laser photodisruption of primate trabecular meshwork: an ex vivo study; Investigative Ophthalmology and Visual Science; 50(3); pp. 1198-1204; Mar. 2009.
Owen; A moving-mirror gonioscope for retinal surgery; British Journal of Ophthalmology; 61(3); pp. 246-247; Mar. 1977 .
Oxford Dictionaries; Detector (definition); 1 page; retrieved from the internet (https://en.oxforddictionaries.com/definition/detector) on Aug. 14, 2018.
Oxford Dictionaries; Sensor (definition); 1 page; retrieved from te internet (http://www.askoxford.com/concise_oed/sensor?view=uk>) on Aug. 14, 2018.
Radhakrishnan et al.; Real-time optical coherence tomography of the anterior segment at 1310 nm; Archives of Opthhalmology: 119(8); pp. 1179-1185; Aug. 2001.
Rosenquist et al.; Outflow resistance of enucleated human eyes at two different perfusion pressures and different extents of trabeculotomy; Current Eye Res.; vol. 8; No. 12; pp. 1233-1240; Dec. 1989.
Savage, James; Gonioscopy in the management of glaucoma; Am. Academy of Ophthalmology; Focal Points; vol. XXIV; No. 3; pp. 1-14; Mar. 2006.
Schocket et al.; Anterior Chamber Tube Shunt to an Encircling Band in the Treatment of Neovascular Glaucoma and other Refractory Glaucomas; Ophthalmology; 92; pp. 553-562; Apr. 1985.
Schultz, Jared; Canaloplasty procedure shows promise for open-angle glaucoma in European study; Ocular Surgery News; vol. 34; Mar. 1, 2007.
Smit et al.; Effects of viscoelastic injection into schlemm's canal in primate and human eyes; J. Am. Academy of Ophthalmology; vol. 109; No. 4; pp. 786-792; Apr. 2002.
Spiegel et al.; Schlemm's canal implant: a new method to lower intraocular pressure in patients with POAG?; Ophthalmic Surgery and Lasers; vol. 30; No. 6; pp. 492-494; Jun. 1999.
Sugiyama et al.; Micro-Diaphragm Pressure Sensor; 1986 International Electron Devices Meeting; pp. 184-187; Dec. 7, 1986.
Toyran et al.; Femtosecond laser photodisruption of human trabecular meshwork: an in vitro study; Experimental Eye Research; 81(3); pp. 298-305; Sep. 2005.
Wilcox et al.; Hypothesis for Improving Accessory Filtration by Using Geometry; Journal of Glaucoma; 3; pp. 244-247; Fall 1994.
Noda et al.; U.S. Appl. No. 17/572,064 entitled "Systems and methods for viscoelastic delivery," filed Jan. 10, 2022.

\* cited by examiner

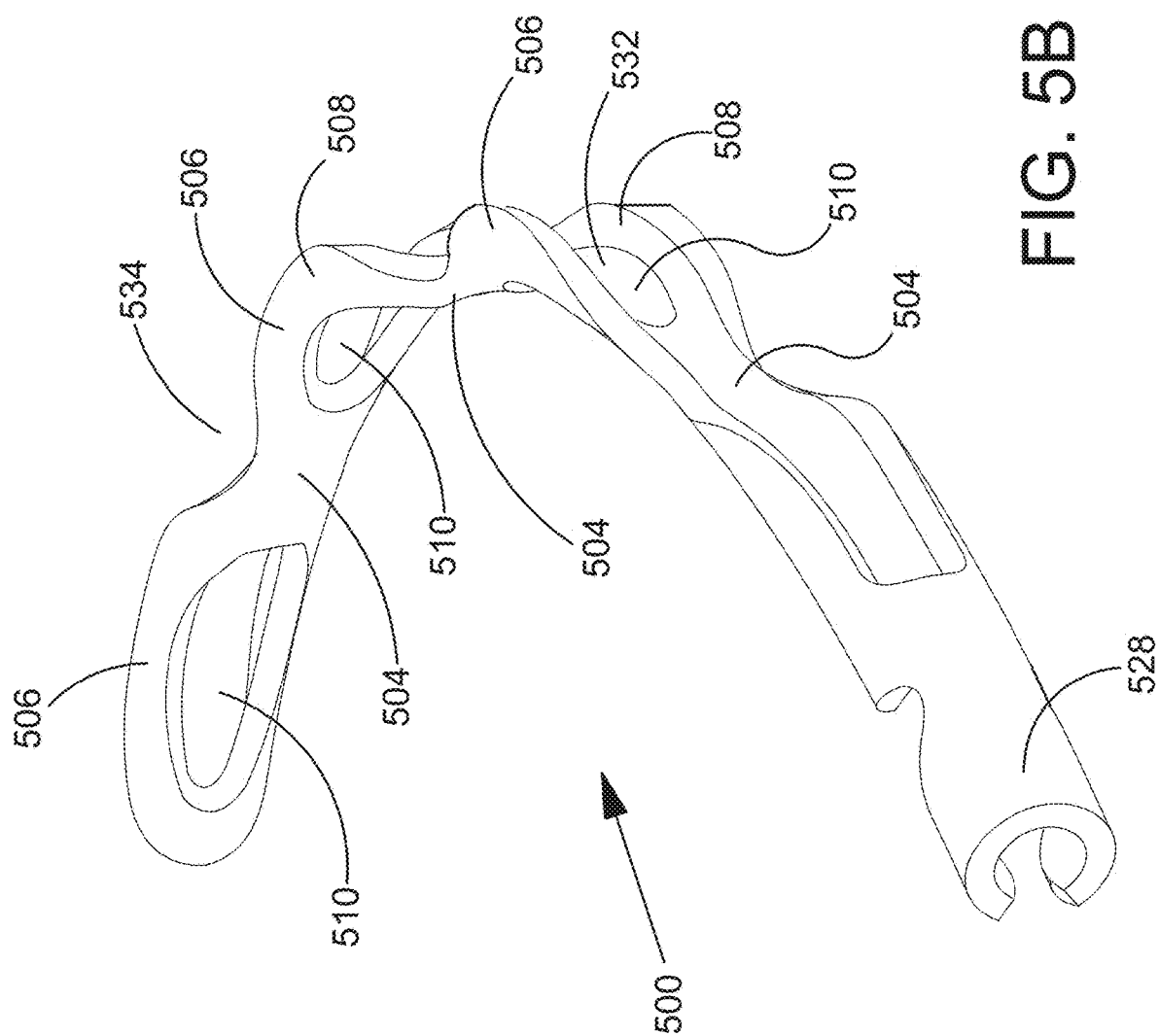

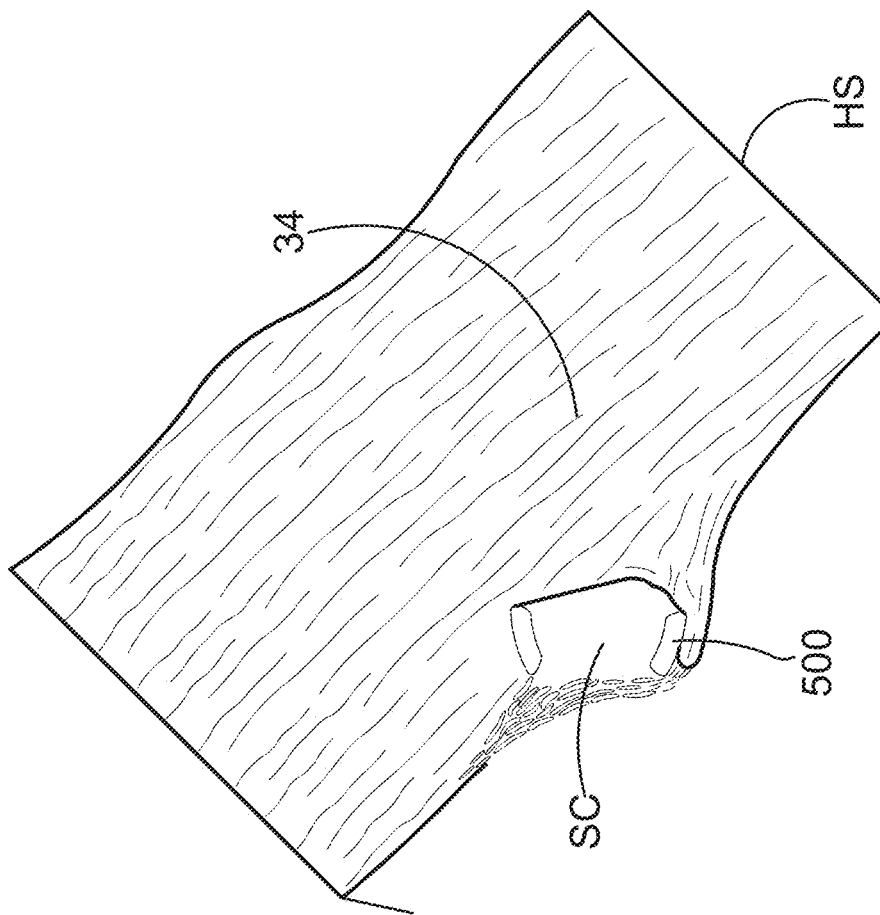
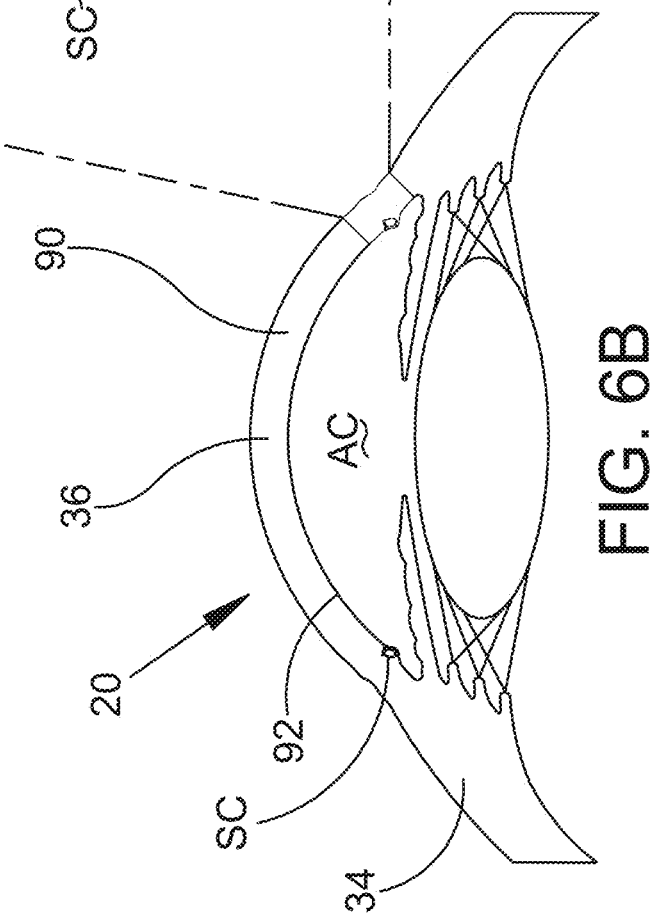
FIG. 6A
FIG. 6B

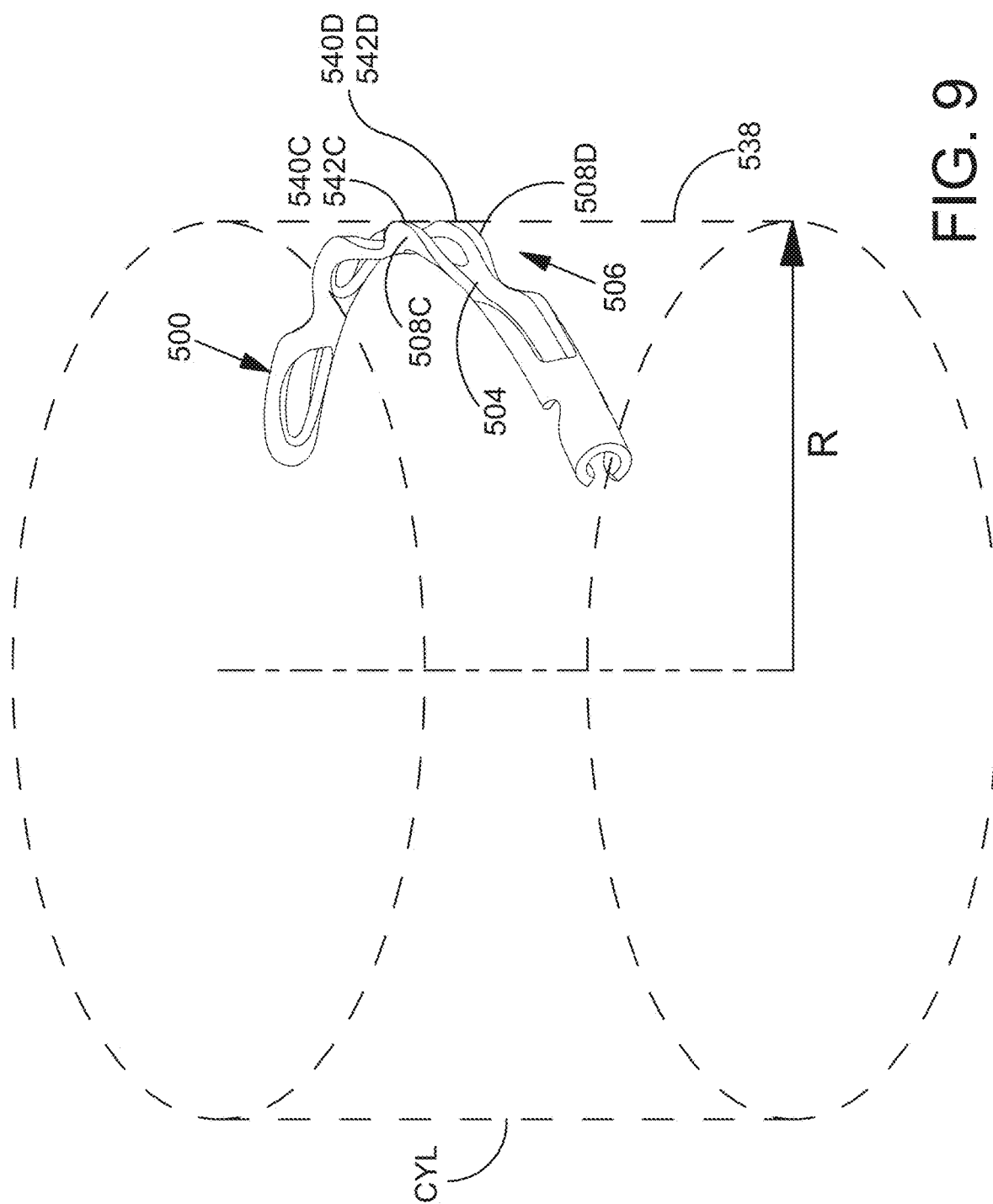

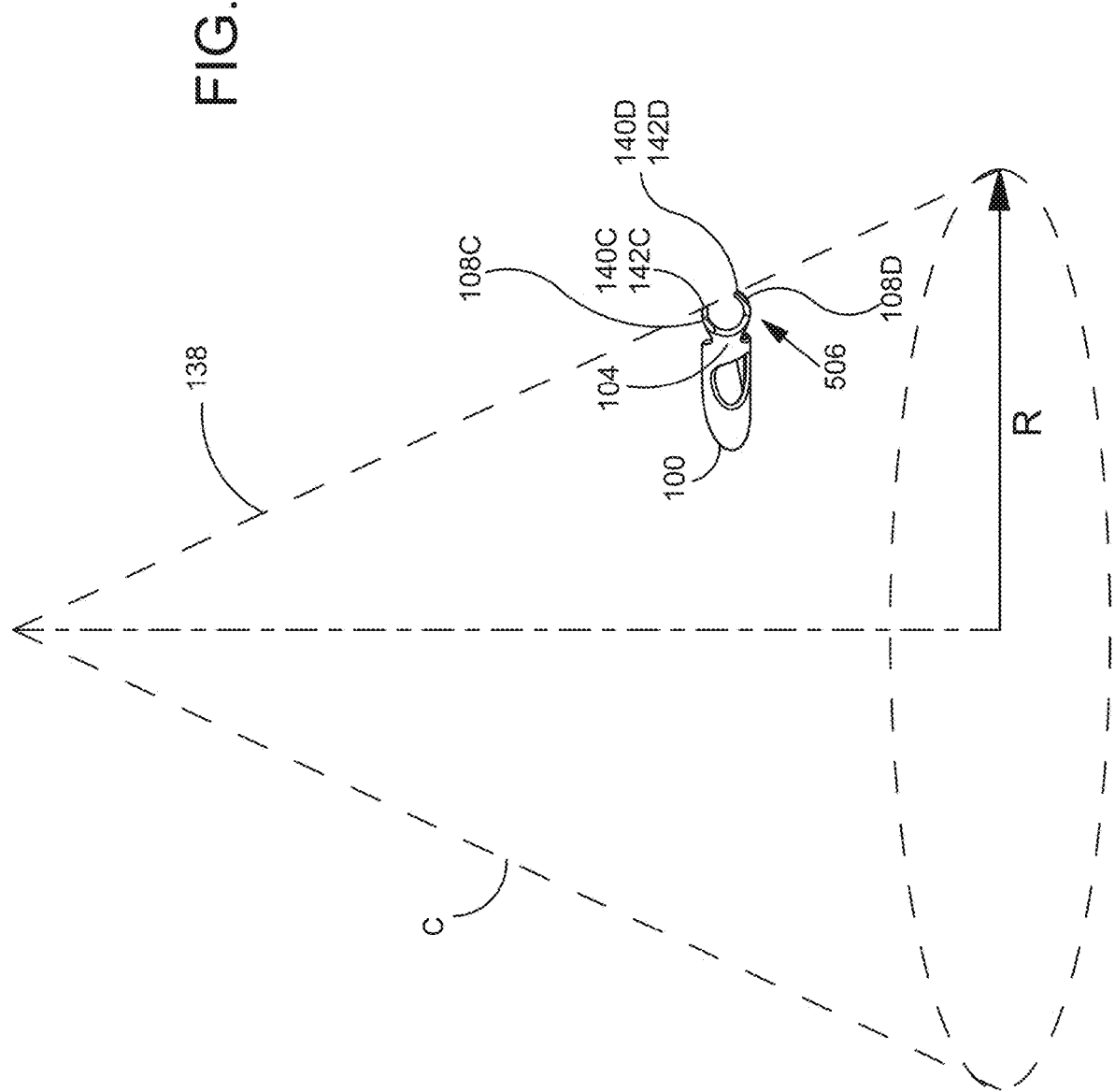

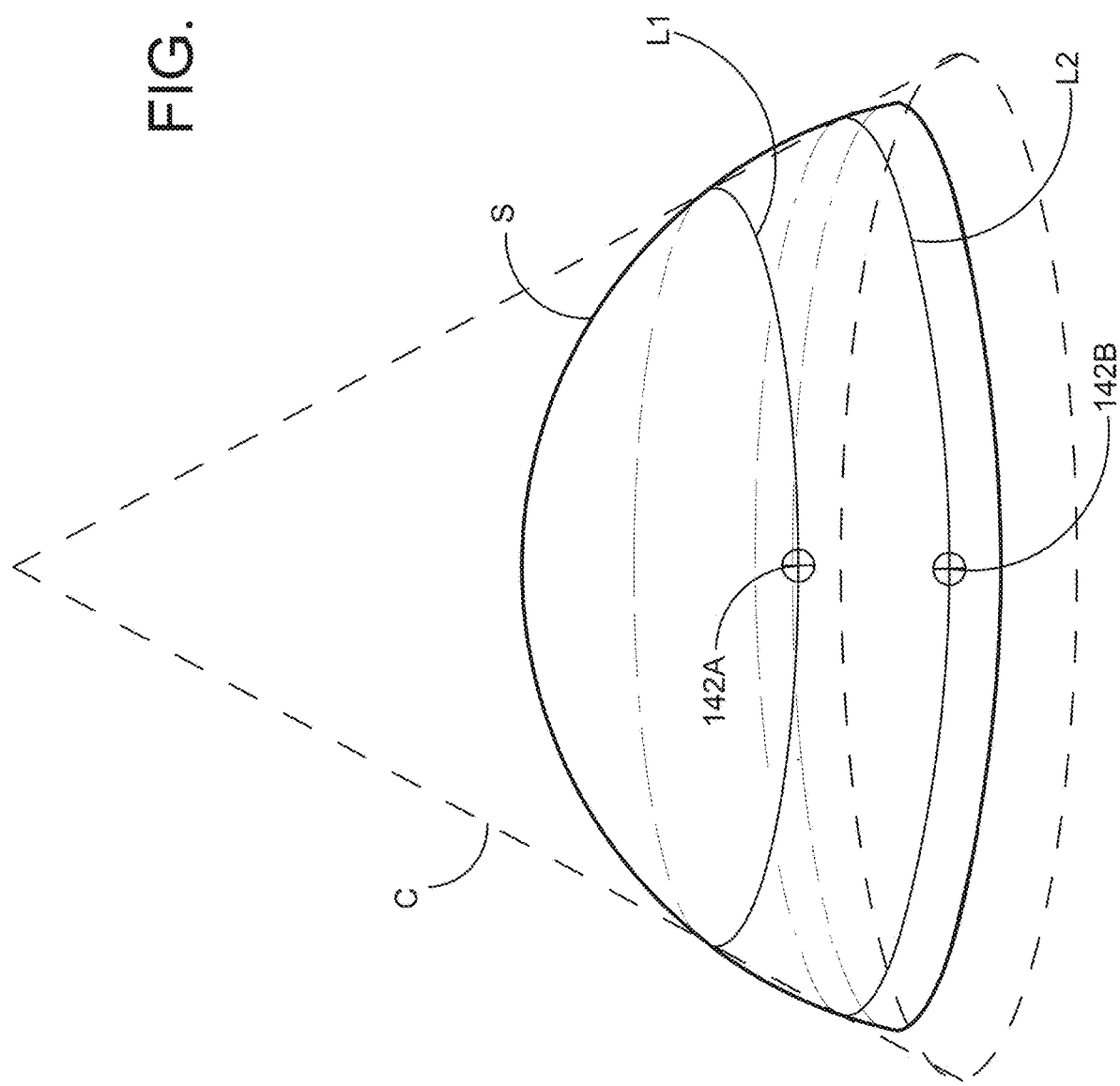

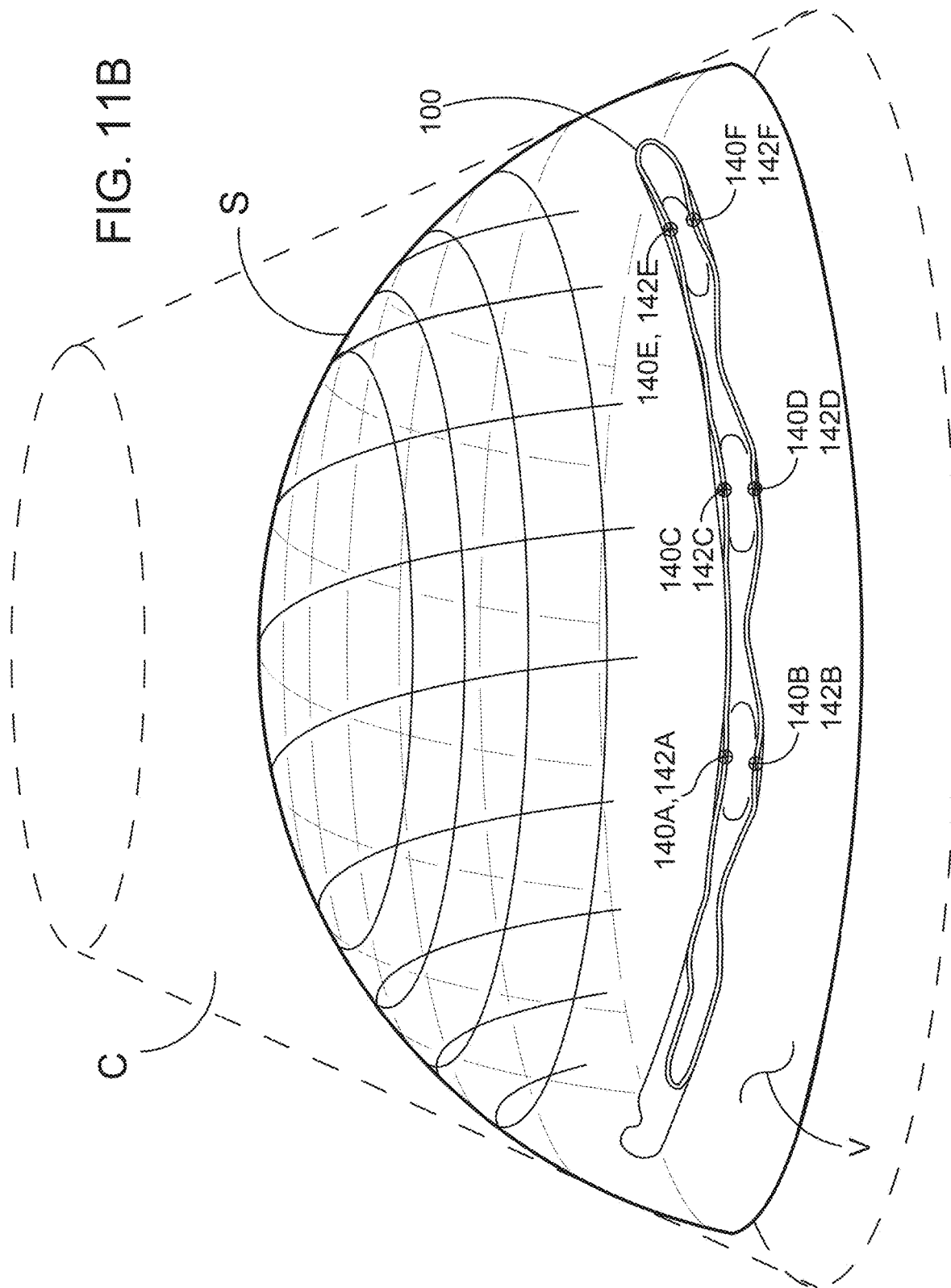

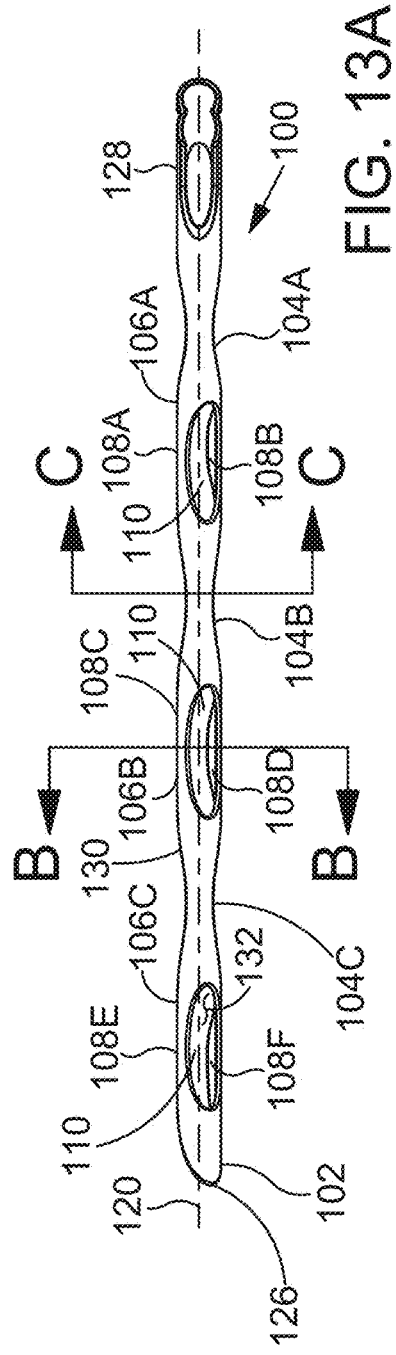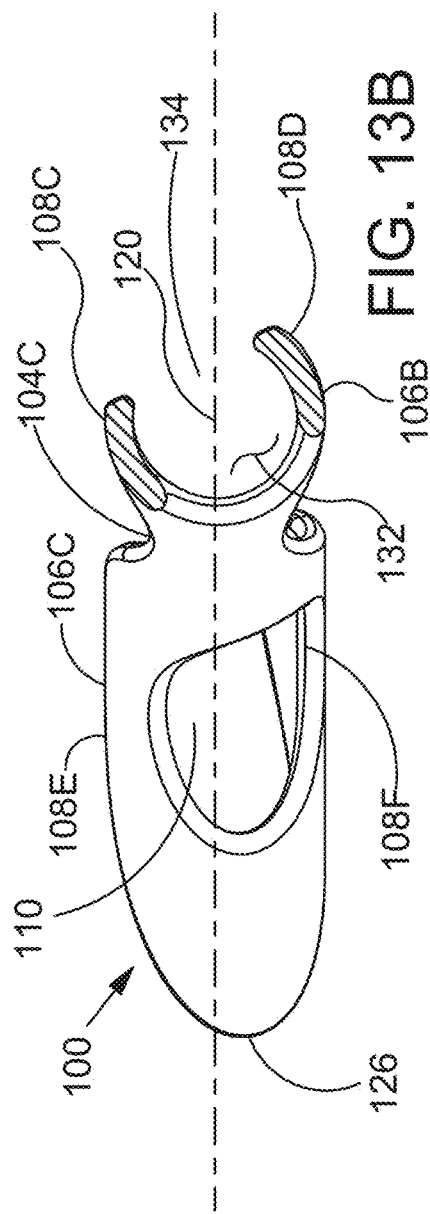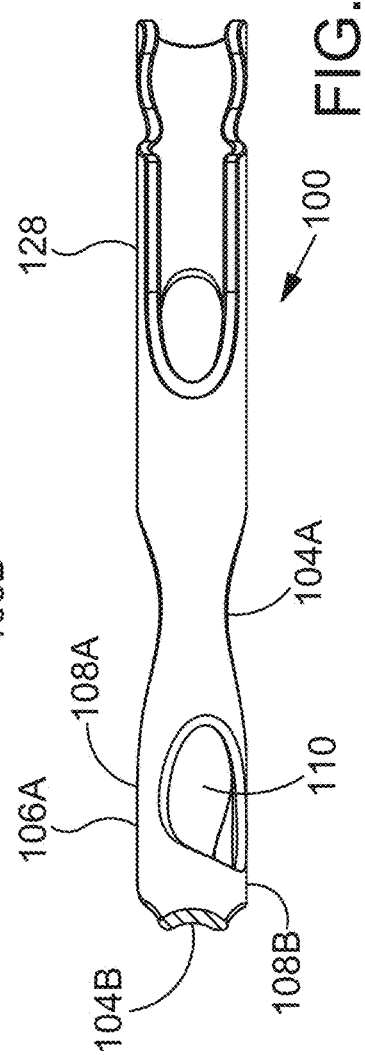

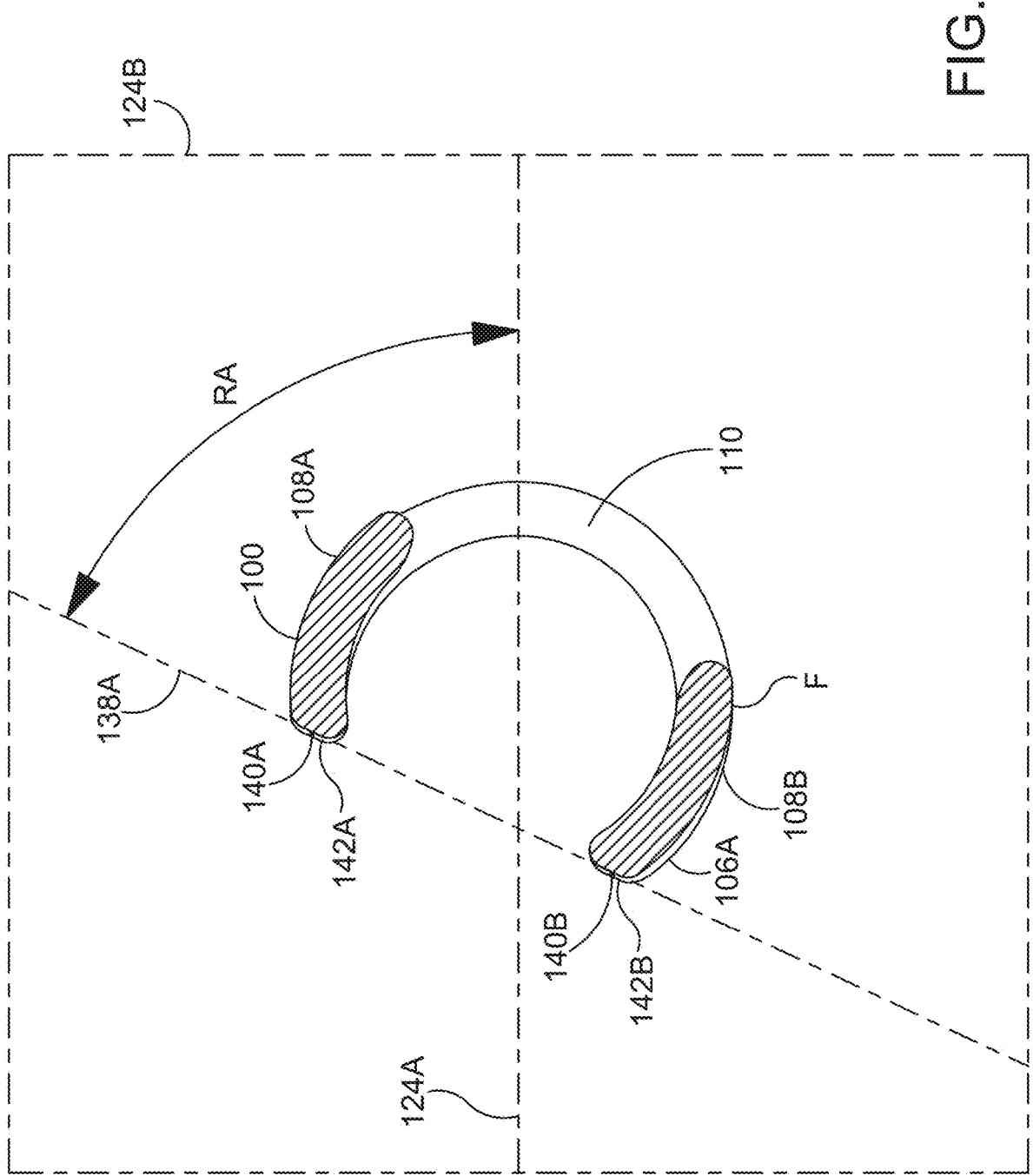

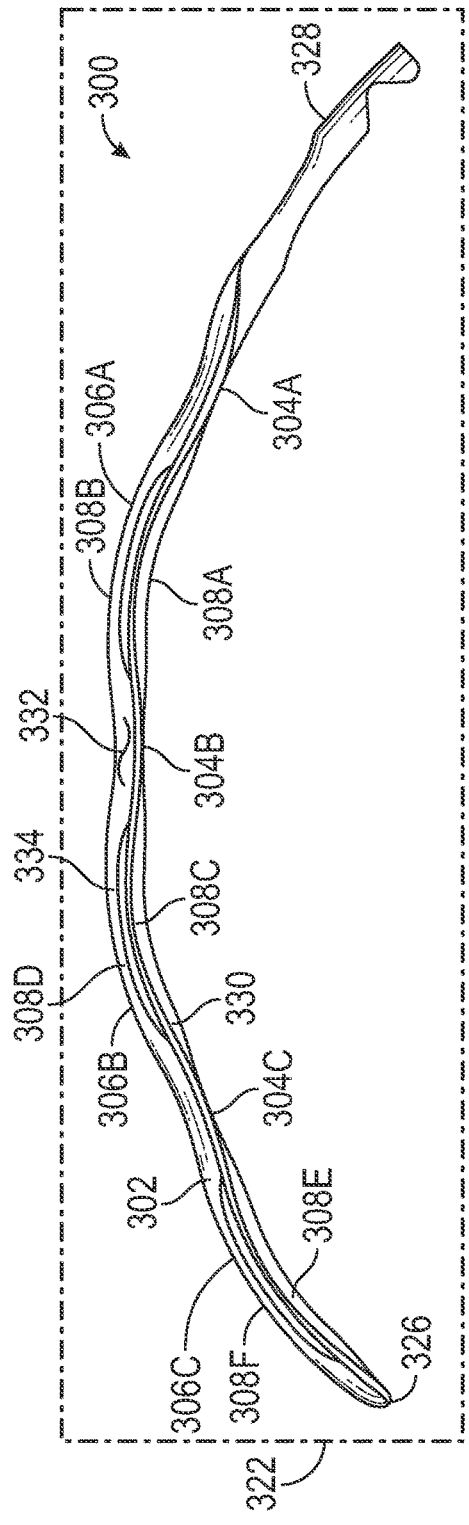
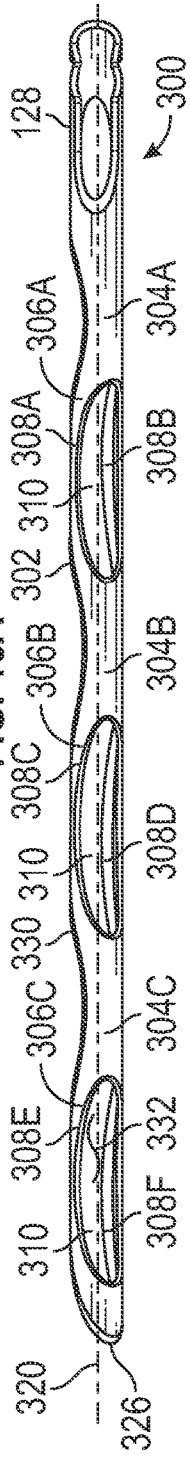
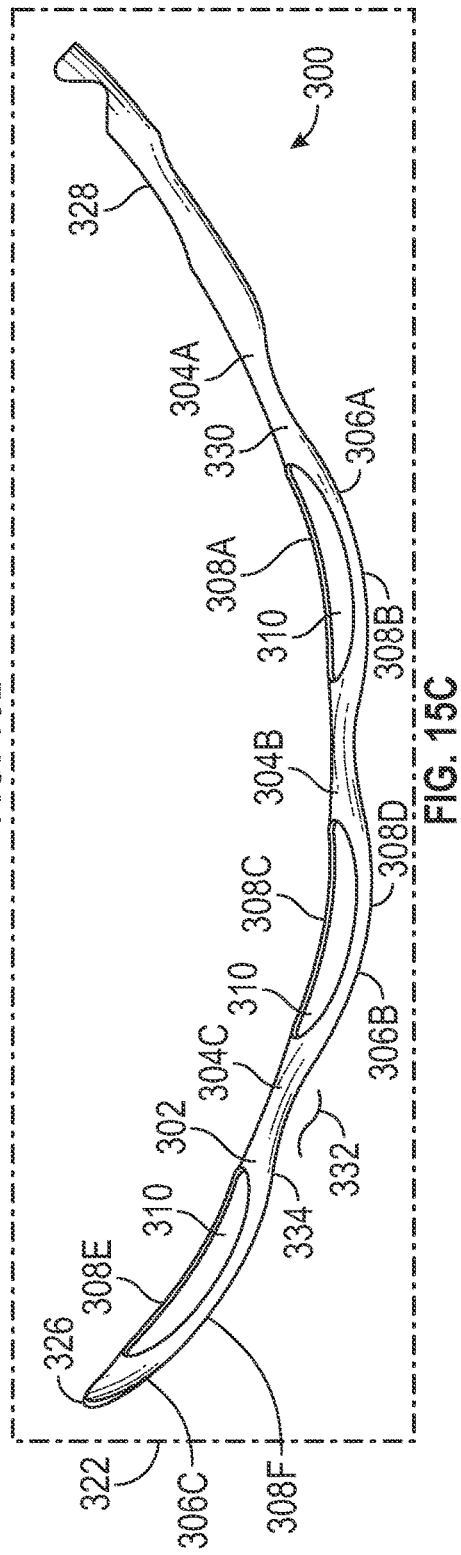
FIG. 15A
FIG. 15B
FIG. 15C

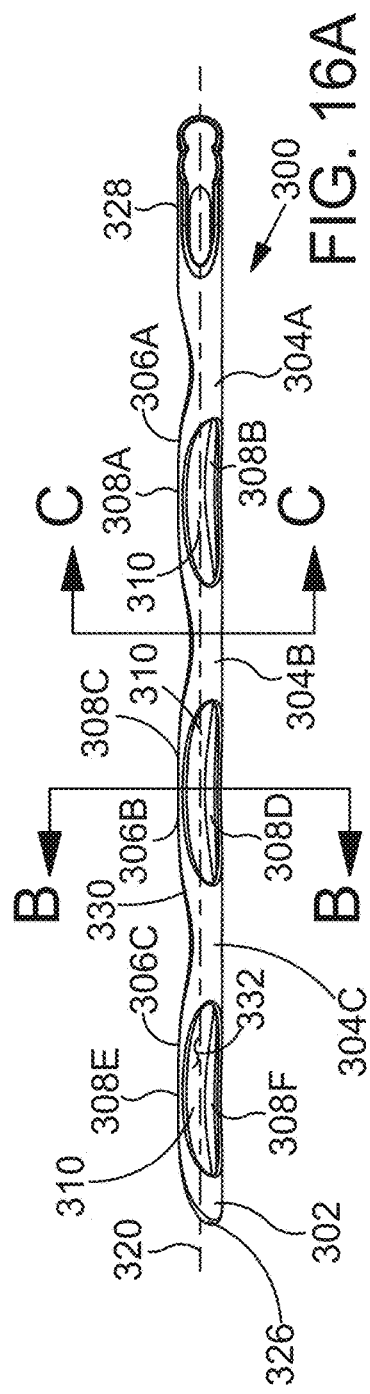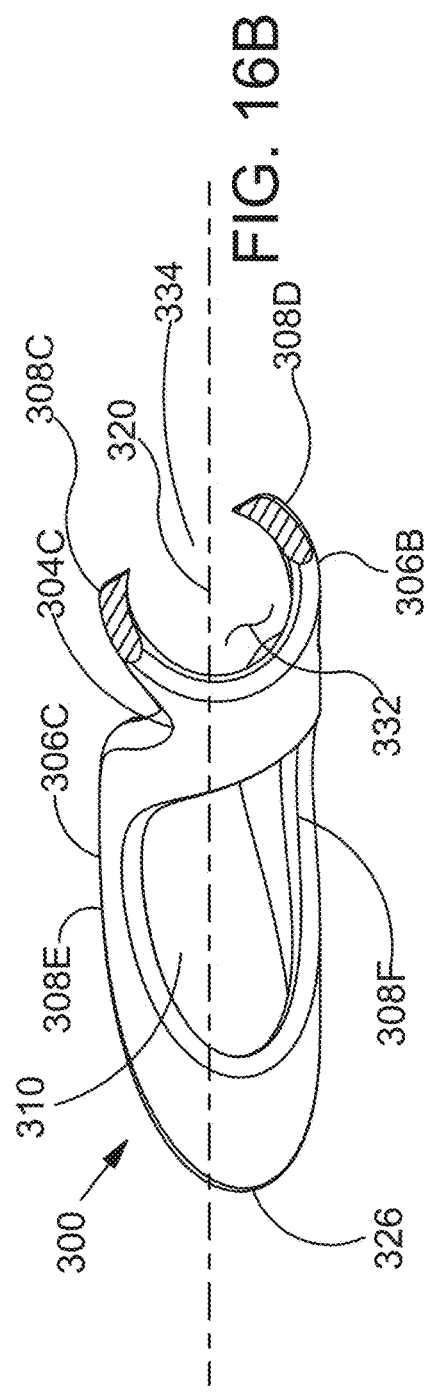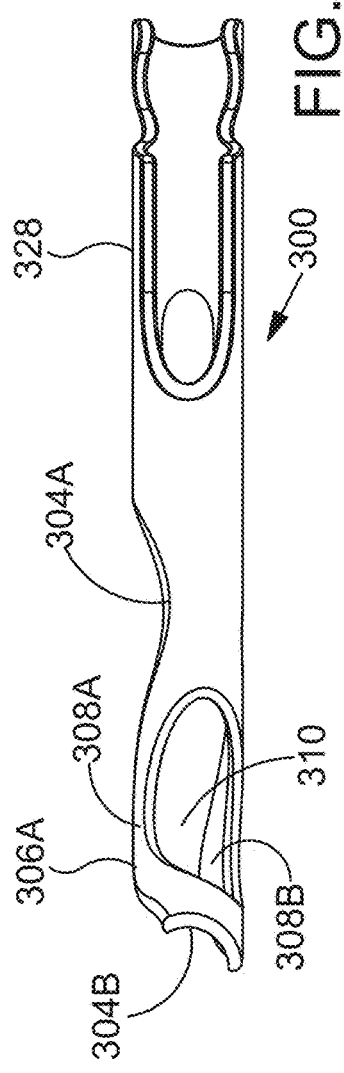

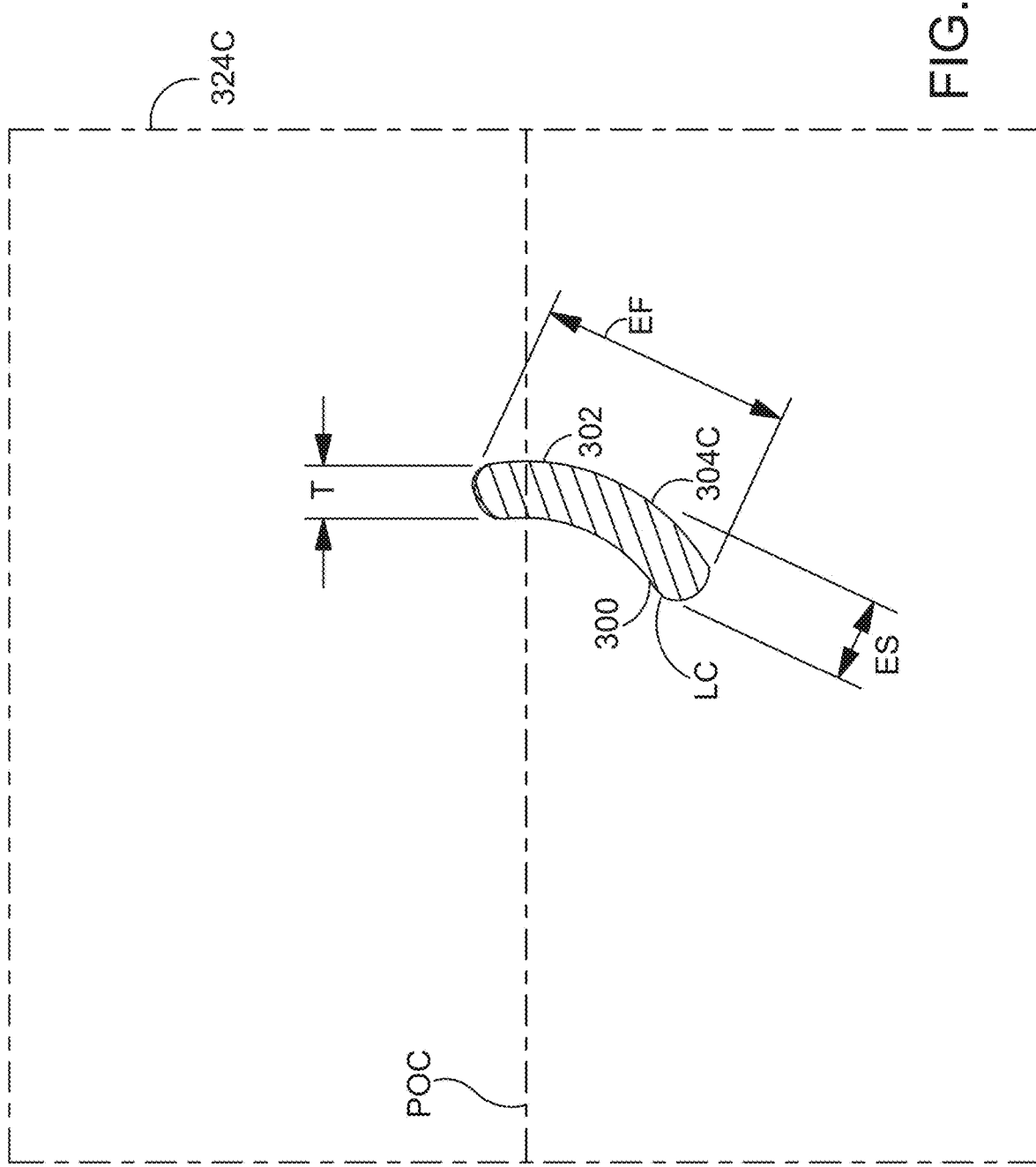

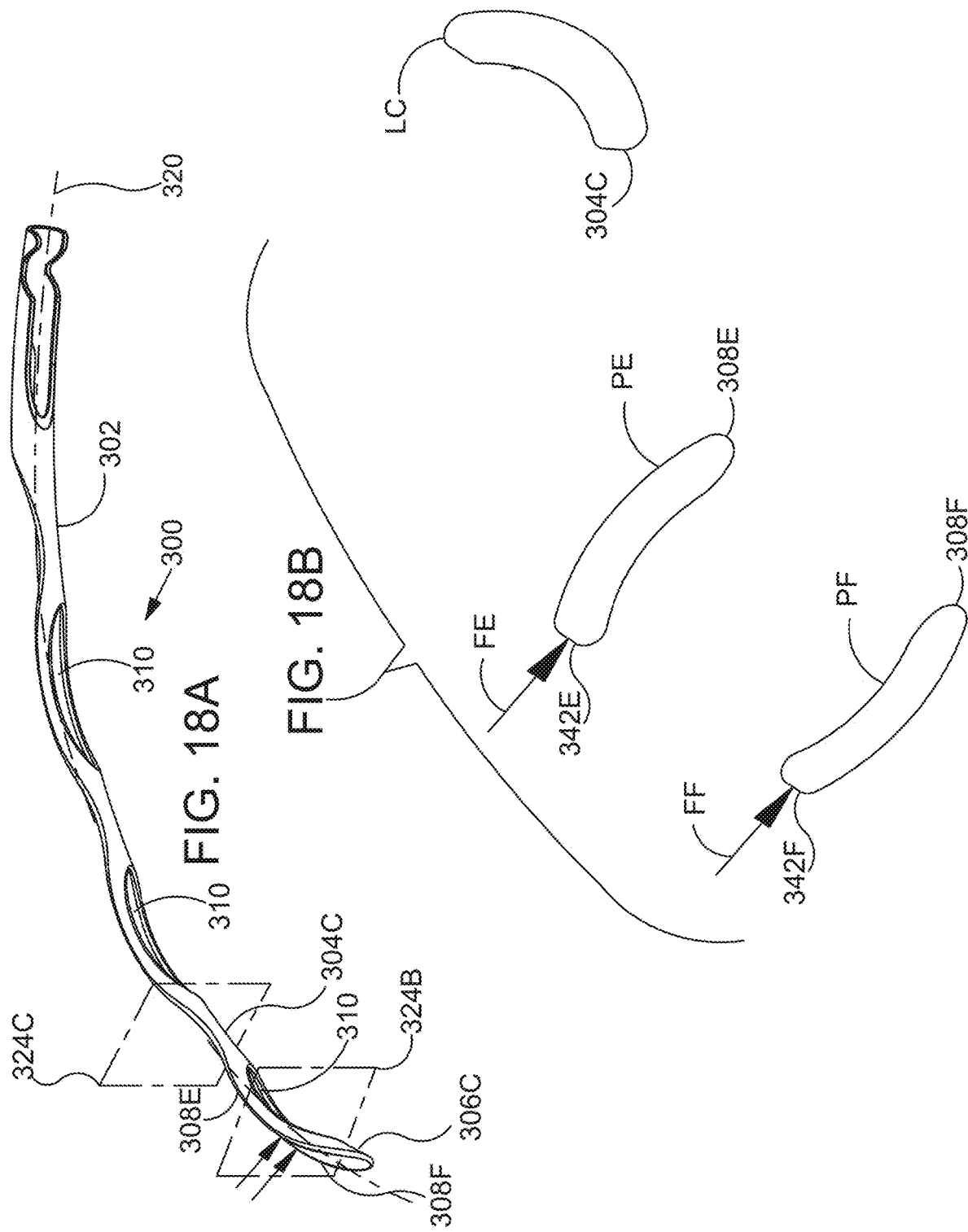

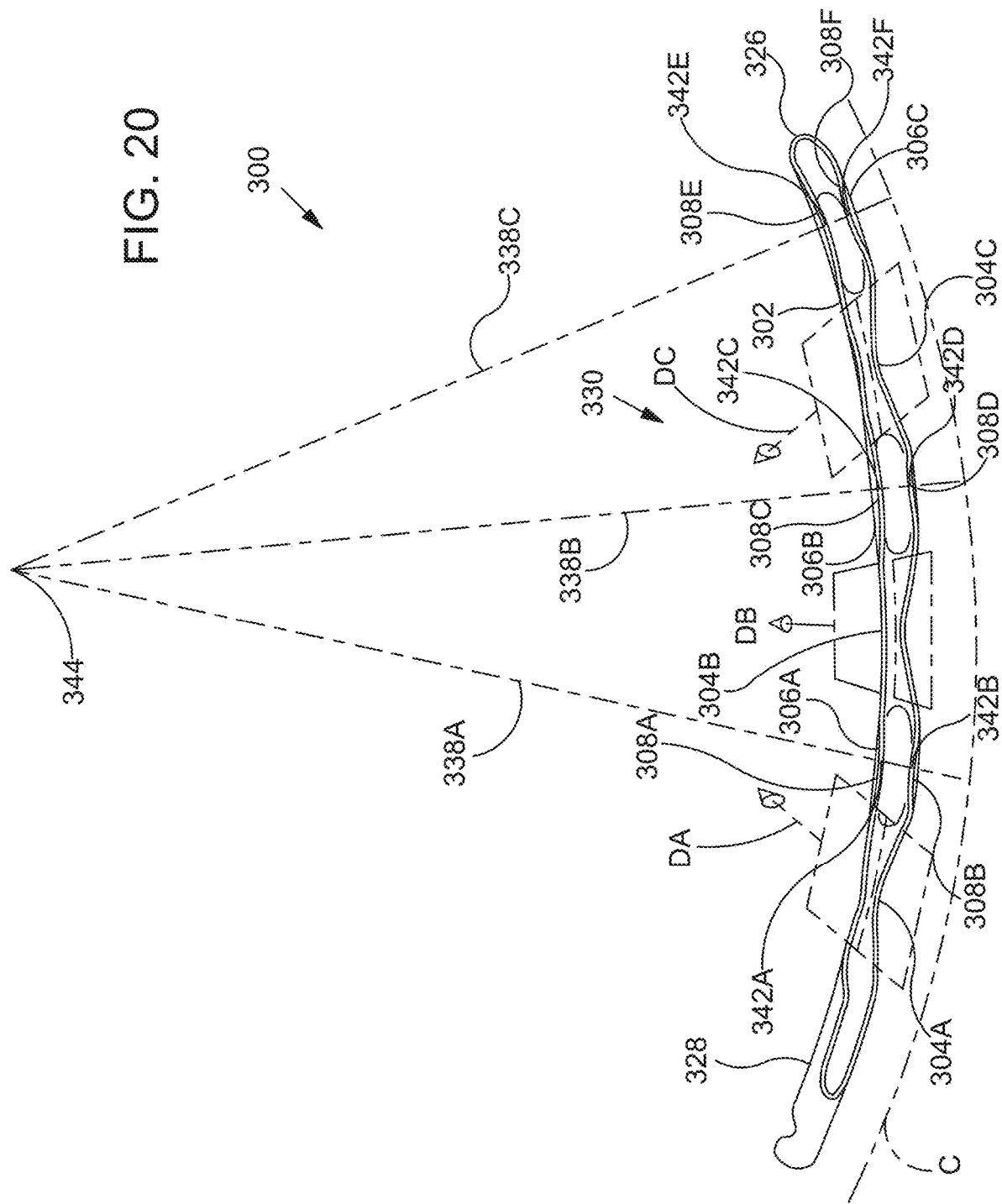

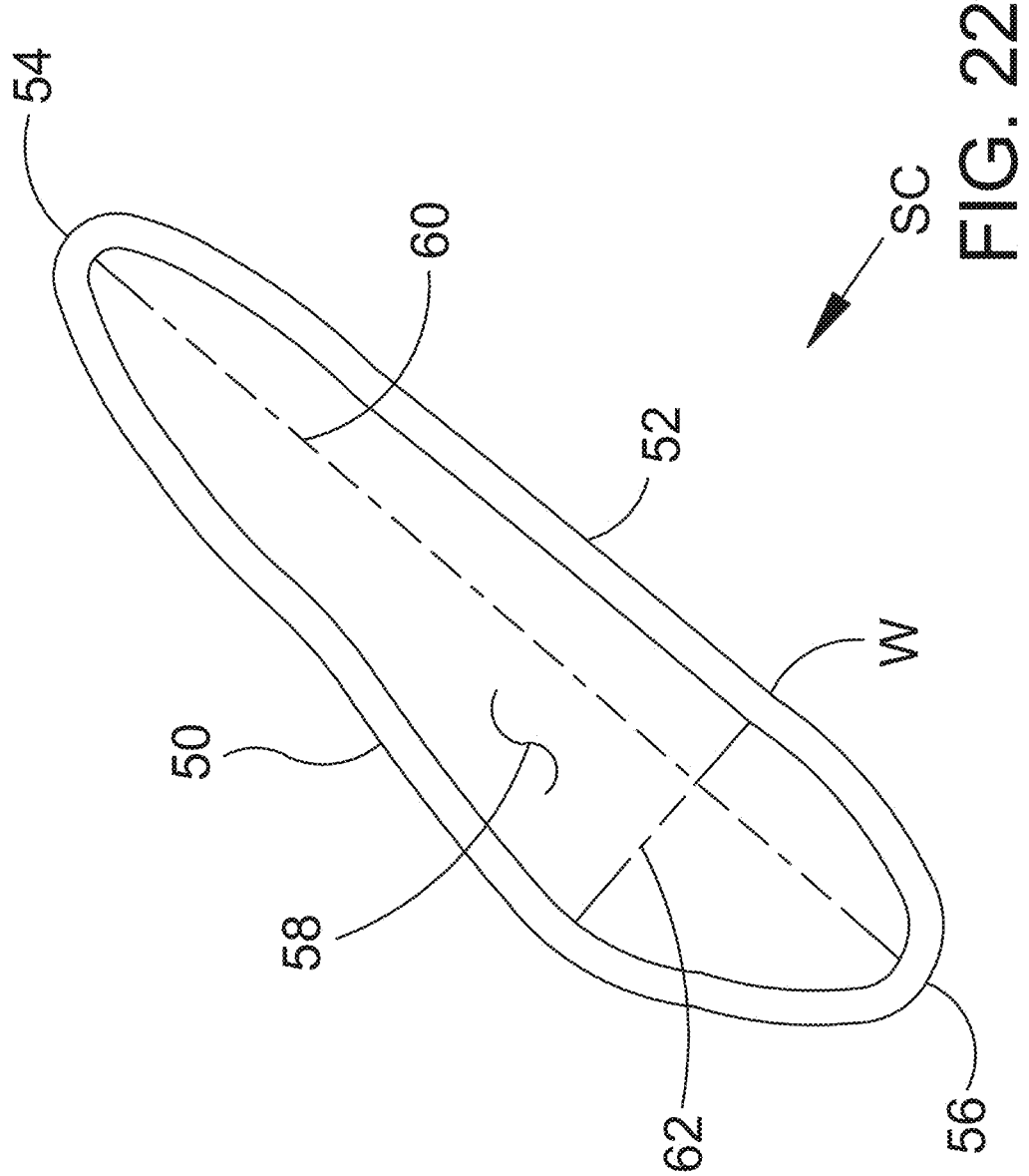

OCULAR IMPLANTS FOR DELIVERY INTO AN ANTERIOR CHAMBER OF THE EYE

CROSS REFERENCE TO RELATED APPLICATIONS

This application is a continuation of U.S. application Ser. No. 15/150,175, filed May 9, 2016, which is a division of U.S. application Ser. No. 13/793,638, filed Mar. 11, 2013, now U.S. Pat. No. 9,358,156, which application claims the benefit under 35 U.S.C. § 119 of U.S. Provisional Application No. 61/635,104, filed Apr. 18, 2012, the disclosures of which are incorporated by reference.

INCORPORATION BY REFERENCE

All publications and patent applications mentioned in this specification are herein incorporated by reference to the same extent as if each individual publication or patent application was specifically and individually indicated to be incorporated by reference.

FIELD

The present invention relates generally to devices that are implanted within the eye. More particularly, the present invention relates to systems, devices and methods for delivering ocular implants into the eye.

BACKGROUND

According to a draft report by The National Eye Institute (NEI) at The United States National Institutes of Health (NIH), glaucoma is now the leading cause of irreversible blindness worldwide and the second leading cause of blindness, behind cataract, in the world. Thus, the NEI draft report concludes, "it is critical that significant emphasis and resources continue to be devoted to determining the pathophysiology and management of this disease." Glaucoma researchers have found a strong correlation between high intraocular pressure and glaucoma. For this reason, eye care professionals routinely screen patients for glaucoma by measuring intraocular pressure using a device known as a tonometer. Many modern tonometers make this measurement by blowing a sudden puff of air against the outer surface of the eye.

The eye can be conceptualized as a ball filled with fluid. There are two types of fluid inside the eye. The cavity behind the lens is filled with a viscous fluid known as vitreous humor. The cavities in front of the lens are filled with a fluid know as aqueous humor. Whenever a person views an object, he or she is viewing that object through both the vitreous humor and the aqueous humor.

Whenever a person views an object, he or she is also viewing that object through the cornea and the lens of the eye. In order to be transparent, the cornea and the lens can include no blood vessels. Accordingly, no blood flows through the cornea and the lens to provide nutrition to these tissues and to remove wastes from these tissues. Instead, these functions are performed by the aqueous humor. A continuous flow of aqueous humor through the eye provides nutrition to portions of the eye (e.g., the cornea and the lens) that have no blood vessels. This flow of aqueous humor also removes waste from these tissues.

Aqueous humor is produced by an organ known as the ciliary body. The ciliary body includes epithelial cells that continuously secrete aqueous humor. In a healthy eye, a stream of aqueous humor flows out of the anterior chamber of the eye through the trabecular meshwork and into Schlemm's canal as new aqueous humor is secreted by the epithelial cells of the ciliary body. This excess aqueous humor enters the venous blood stream from Schlemm's canal and is carried along with the venous blood leaving the eye.

When the natural drainage mechanisms of the eye stop functioning properly, the pressure inside the eye begins to rise. Researchers have theorized prolonged exposure to high intraocular pressure causes damage to the optic nerve that transmits sensory information from the eye to the brain. This damage to the optic nerve results in loss of peripheral vision. As glaucoma progresses, more and more of the visual field is lost until the patient is completely blind.

In addition to drug treatments, a variety of surgical treatments for glaucoma have been performed. For example, shunts were implanted to direct aqueous humor from the anterior chamber to the extraocular vein (Lee and Scheppens, "Aqueous-venous shunt and intraocular pressure," Investigative Ophthalmology (February 1966)). Other early glaucoma treatment implants led from the anterior chamber to a sub-conjunctival bleb (e.g., U.S. Pat. Nos. 4,968,296 and 5,180,362). Still others were shunts leading from the anterior chamber to a point just inside Schlemm's canal (Spiegel et al., "Schlemm's canal implant: a new method to lower intraocular pressure in patients with POAG?" Ophthalmic Surgery and Lasers (June 1999); U.S. Pat. Nos. 6,450,984; 6,450,984). More recent glaucoma treatment implants are designed to be advanced into and placed in Schlemm's canal. (See, e.g., U.S. Pat. No. 7,740,604; US 2011/0009958.)

SUMMARY OF THE DISCLOSURE

The present invention relates to methods and devices for treating glaucoma. In particular, the invention relates to an implant designed to extend from the anterior chamber of a human eye into Schlemm's canal and to support the tissue of Schlemm's canal to support flow of aqueous humor from the anterior chamber into Schlemm's canal to the outflow channels communicating with Schlemm's canal.

In one aspect, the invention provides an ocular implant adapted to be disposed within Schlemm's canal of a human eye and configured to support Schlemm's canal in an open state. The ocular implant has a body extending along a curved longitudinal central axis in a curvature plane, the body having a central channel bordered by an opening, first and second frames and a spine interposed between the first and second frames, the spine having a circumferential extent, the body having dimensions adapted to be fit within Schlemm's canal; each frame comprising a first strut on one side of the implant and a second strut on an opposite side of the implant, the first strut extending circumferentially beyond the circumferential extent of the spine on the one side of the implant and the second strut extending circumferentially beyond the circumferential extent of the spine on the other side of the implant, the circumferential extent of the first strut with respect to the plane of curvature being greater than the circumferential extent of the second strut with respect to the plane of curvature. In some embodiments, the body has a curved resting shape.

The implant may be adapted to bend preferentially in a preferential bending direction. In some embodiments, the preferential bending direction is in the curvature plane, and in some embodiments the preferential bending direction is not in the curvature plane.

In some embodiments, the circumferential extent of the first strut beyond the circumferential extent of the spine on the one side of the implant is greater than the circumferential extent of the second strut beyond the circumferential extent of the spine on the other side of the implant.

In embodiments in which the implant also has a third frame and a second spine interposed between the second and third frames, the second spine having a circumferential extent, the third frame having a first strut on one side of the implant and a second strut on an opposite side of the implant, the first strut and second strut of the third frame each having a circumferential extent greater than the circumferential extent of the second spine, the circumferential extent of the first strut with respect to the plane of curvature may be greater than the circumferential extent of the second strut with respect to the plane of curvature. The first, second and third frames may be substantially identical, and the first and second spines may be substantially identical. In some embodiments, the first spine is adapted to bend preferentially in a first bending direction, and the second spine is adapted to bend preferentially in a second bending direction different from the first bending direction.

In some embodiments, the plane of curvature intersects the spine. The spine may extend circumferentially in substantially equal amounts from the plane of curvature.

In some embodiments, the opening is an elongated opening extending longitudinally along the frames and the spine. The implant may also have a second opening bordered by the first and second struts of the first frame and a third opening bordered by the first and second struts of the second frame.

Another aspect of the invention provides a method of treating glaucoma in a human eye. The method may include the following steps: inserting a cannula through a cornea of the eye into an anterior chamber of the eye; placing a distal opening of the cannula in communication with Schlemm's canal of the eye; moving an ocular implant out of the cannula through the opening and into Schlemm's canal, the ocular implant having a central channel and first and second landing surfaces, the first and second landing surfaces being disposed on opposite sides of the central channel; and engaging a scleral wall of Schlemm's canal with the first and second landing surfaces such that reaction forces on the first and second landing surfaces from engagement with the scleral wall are substantially equal.

In some embodiments, the engaging step includes the step of engaging the scleral wall of Schlemm's canal with the first and second landing surfaces without substantially twisting the ocular implant.

In some embodiments, the implant has a resting shape forming a curve, and the method includes the step of orienting the implant curve with a curve of Schlemm's canal.

In some embodiments, the cannula is curved at a distal end, and the method includes the step of orienting the cannula for tangential delivery of the implant from the cannula into Schlemm's canal.

BRIEF DESCRIPTION OF THE DRAWINGS

FIG. 5B is a perspective view of the ocular implant used to generate the slide image shown in FIG. 5A.

FIG. 6A is a stylized line drawing illustrating histology slide HS shown in the previous figure. FIG. 6B is a simplified cross-sectional view illustrating the eye from which the histology sample was taken. FIG. 6A and FIG. 6B are presented on a single page to illustrate the location of the histology sample relative to other portions of the eye.

FIG. 9 is a perspective view showing the ocular implant of FIG. 7.

FIG. 10 is an additional perspective view showing the ocular implant of FIG. 8.

FIG. 11A is a stylized perspective view showing a conical surface that is sized and positioned so as to intersect a hemispherical surface in two places. FIG. 11B is a stylized perspective view showing an ocular implant disposed inside a chamber defined by a hemispherical surface.

FIG. 13A is a plan view showing the ocular implant of FIG. 8. FIG. 13B is an enlarged section view taken along section line B-B shown in FIG. 13A. FIG. 13C is an additional enlarged section view taken along section line C-C shown in FIG. 13A.

FIG. 14B is a plan view further illustrating the second plane shown in FIG. 14A.

FIG. 15A, FIG. 15B and FIG. 15C are multi-plan views of a yet another ocular implant in accordance with the detailed description.

FIG. 16A is a plan view showing the ocular implant of FIG. 15. FIG. 16B is an enlarged section view taken along section line B-B shown in FIG. 16A. FIG. 16C is an additional enlarged section view taken along section line C-C shown in FIG. 16A.

FIG. 17C is a plan view further illustrating the third plane shown in FIG. 17A.

FIG. 18A is an additional perspective view of the ocular implant shown in the previous figure. The ocular implant 300 of FIG. 18A includes a distal-most spine and a distal-most frame. In the exemplary embodiment of FIG. 18A, the distal-most frame comprises a first strut and a second strut. FIG. 18B is a stylized isometric view showing the profiles of the distal-most spine, the first strut and the second strut shown in FIG. 18A.

FIG. 20 is a perspective view showing yet another exemplary ocular implant in accordance with the detailed description.

FIG. 22 is an enlarged cross-sectional view further illustrating Schlemm's canal SC shown in FIG. 21.

DETAILED DESCRIPTION

The following detailed description should be read with reference to the drawings in which similar elements in different drawings are numbered the same. The drawings, which are not necessarily to scale, depict illustrative embodiments and are not intended to limit the scope of the invention.

Figure 1:
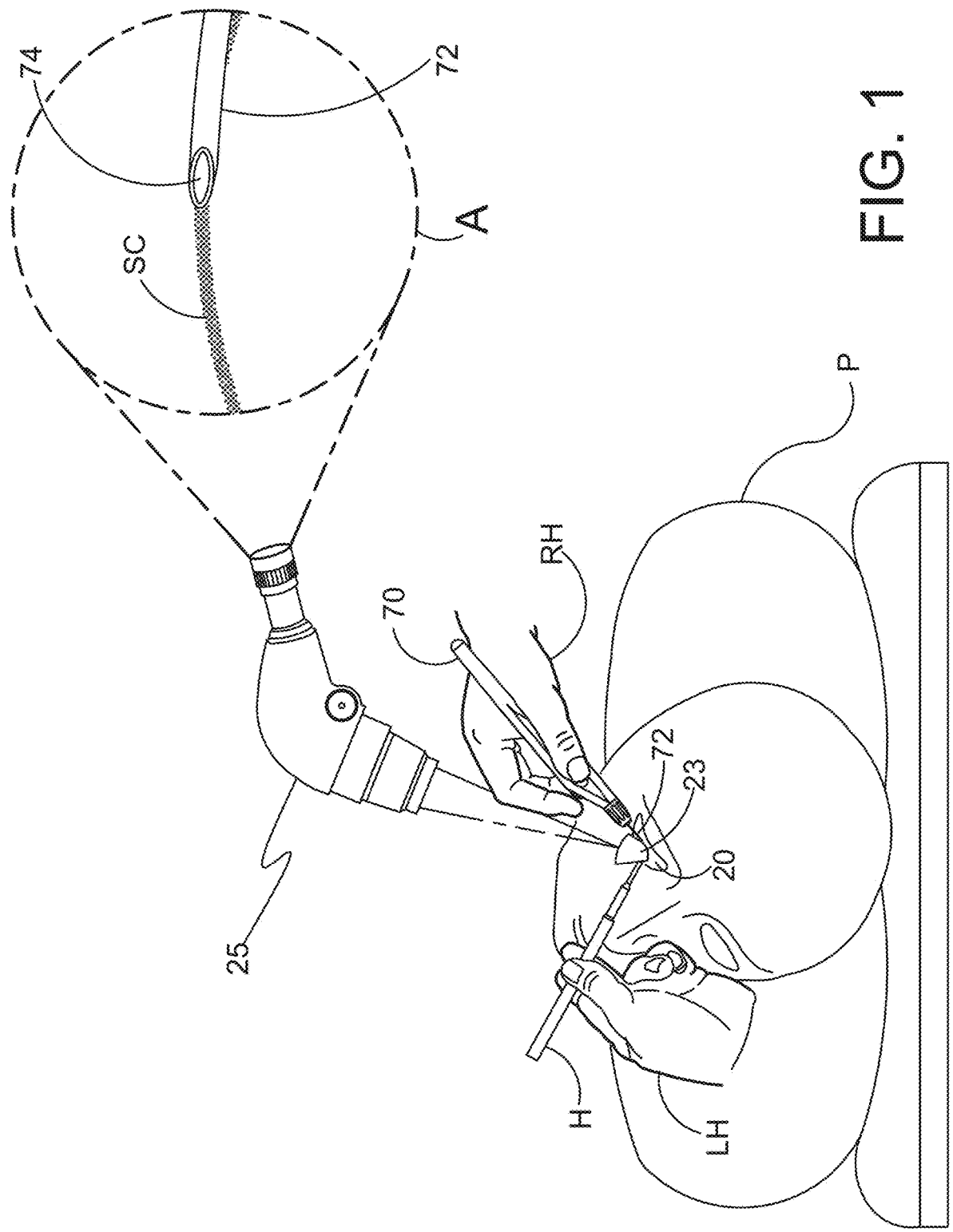
FIG. 1 is a stylized representation of an exemplary medical procedure in accordance with this detailed description.

FIG. 1 is a stylized representation of an exemplary medical procedure in accordance with this detailed description. In the exemplary procedure of FIG. 1, a physician is treating an eye 20 of a patient P. In the exemplary procedure of FIG. 1, the physician is holding a hand piece of a delivery system 70 in his or her right hand RH. The physician's left hand LH is holding the handle H of a gonio lens 23 in the exemplary procedure of FIG. 1. It will be appreciated that some physicians may prefer holding the delivery system hand piece in the right hand and the gonio lens handle in the left hand.

During the exemplary procedure illustrated in FIG. 1, the physician may view the interior of the anterior chamber using gonio lens 23 and a microscope 25. Detail A of FIG. 1 is a stylized simulation of the image viewed by the physician. A distal portion of a cannula 72 is visible in Detail A. A shadow-like line indicates the location of Schlemm's canal SC which is lying under various tissue (e.g., the trabecular meshwork) that surround the anterior chamber. A distal opening of cannula 72 is positioned near Schlemm's canal SC of eye 20.

Methods in accordance with this detailed description may include the step of advancing the distal end of cannula 72 through the cornea of eye 20 so that a distal portion of cannula 72 is disposed in the anterior chamber of the eye. Cannula 72 may then be used to access Schlemm's canal of the eye, for example, by piercing the wall of Schlemm's canal with the distal end of cannula 72. A distal opening of cannula 72 may be placed in fluid communication with a lumen defined by Schlemm's canal. The ocular implant may be advanced out of the cannula and into Schlemm's canal. Insertion of the ocular implant into Schlemm's canal may facilitate the flow of aqueous humor out of the anterior chamber of the eye.

Figure 2:
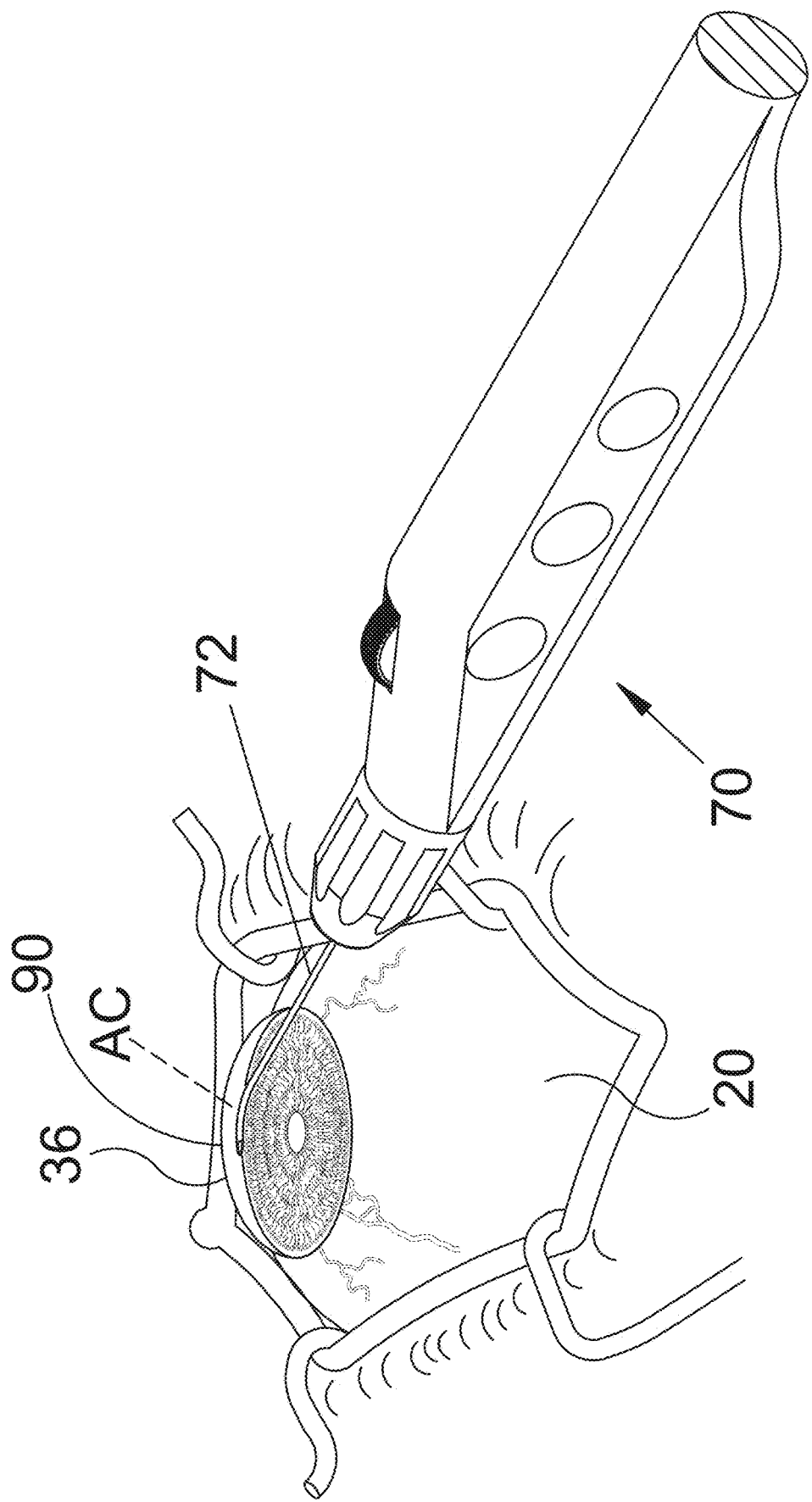
FIG. 2 is an enlarged perspective view further illustrating delivery system 70 and eye 20 shown in the previous figure.

FIG. 2 is an enlarged perspective view further illustrating delivery system 70 and eye 20 shown in the previous figure.

In FIG. 2, cannula 72 of delivery system 70 is shown extending through a dome-shaped wall 90 of eye 20. The dome shaped wall includes the cornea 36 of eye 20 and scleral tissue that meets the cornea at a limbus of the eye. A distal portion of cannula 72 is disposed inside the anterior chamber AC defined by the dome-shaped wall 90. In the embodiment of FIG. 2, cannula 72 is configured so that a distal opening of cannula 72 can be placed in fluid communication with Schlemm's canal. In the embodiment of FIG. 2, the distal end of cannula 72 is curved so that the distal opening of the cannula can be inserted at least partially into Schlemm's canal along a tangential approach.

In the embodiment of FIG. 2, an ocular implant is disposed in a passageway defined by cannula 72. Delivery system 70 includes a mechanism that is capable of advancing and retracting the ocular implant along the length of cannula 72. The ocular implant may be placed in Schlemm's canal of eye 20 by advancing the ocular implant through the distal opening of cannula 72 while the distal opening is in fluid communication with Schlemm's canal.

Figure 3A:
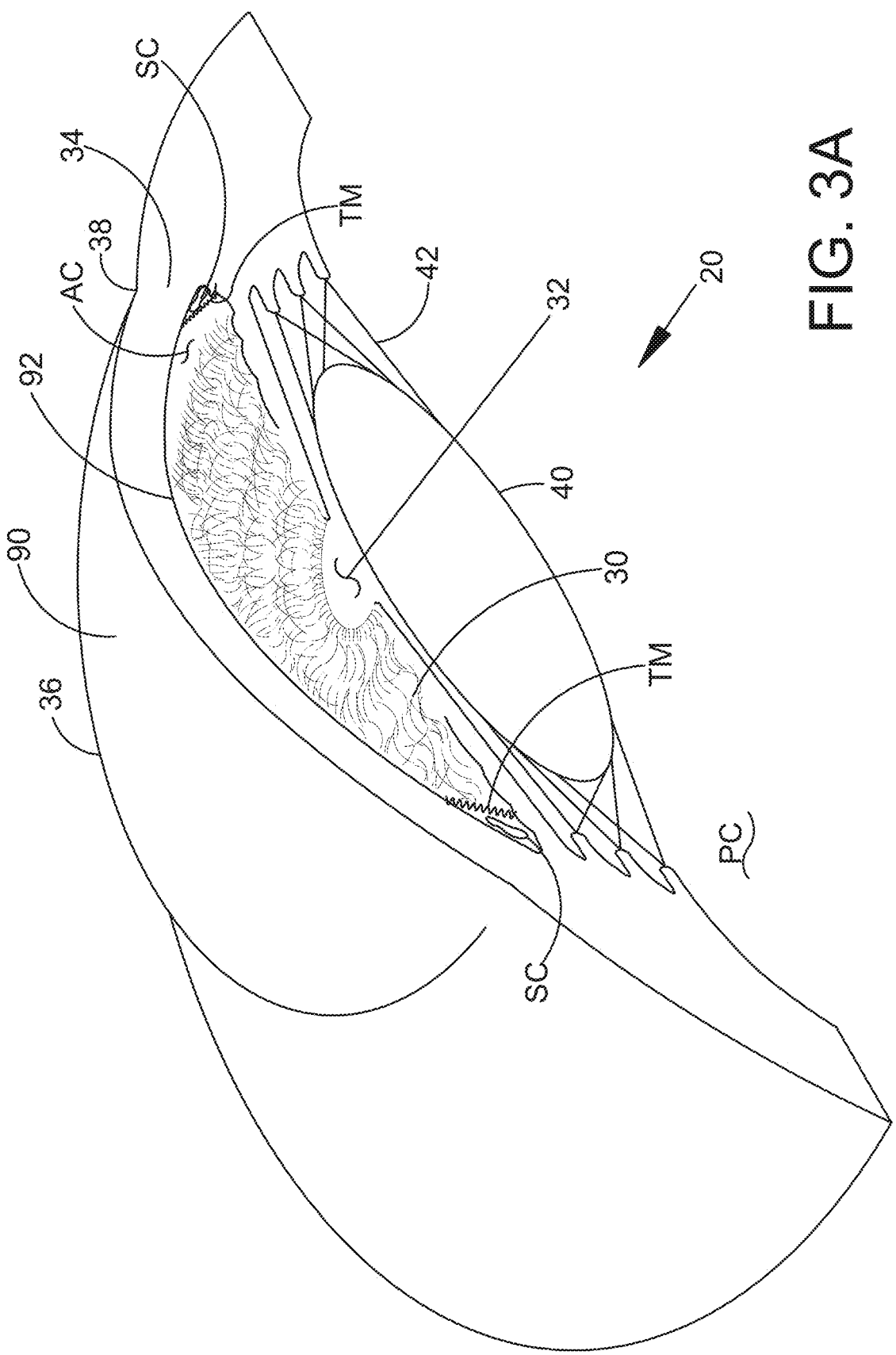
FIG. 3A is a stylized perspective view illustrating the anatomy of an eye.

FIG. 3A is a stylized perspective view illustrating a portion of eye 20 discussed above. Eye 20 includes an iris 30 defining a pupil 32. In FIG. 3A, eye 20 is illustrated in a cross-sectional view created by a cutting plane passing through the center of pupil 32. Eye 20 includes a dome-shaped wall 90 having a surface 92 defining an anterior chamber AC. In FIG. 3A, surface 92 is shown having a generally hemispherical shape. Dome-shaped wall 90 of eye 20 comprises a cornea 36 and scleral tissue 34. The scleral tissue 34 meets the cornea 36 at a limbus 38 of eye 20. Additional scleral tissue 34 of eye 20 surrounds a posterior chamber PC filled with a viscous fluid known as vitreous humor. A lens 40 of eye 20 is located between anterior chamber AC and posterior chamber PC. Lens 40 is held in place by a number of ciliary zonules 42.

Whenever a person views an object, he or she is viewing that object through the cornea, the aqueous humor, and the lens of the eye. In order to be transparent, the cornea and the lens can include no blood vessels. Accordingly, no blood flows through the cornea and the lens to provide nutrition to these tissues and to remove wastes from these tissues. Instead, these functions are performed by the aqueous humor. A continuous flow of aqueous humor through the eye provides nutrition to portions of the eye (e.g., the cornea and the lens) that have no blood vessels. This flow of aqueous humor also removes waste from these tissues.

Aqueous humor is produced by an organ known as the ciliary body. The ciliary body includes epithelial cells that continuously secrete aqueous humor. In a healthy eye, a stream of aqueous humor flows out of the eye as new aqueous humor is secreted by the epithelial cells of the ciliary body. This excess aqueous humor enters the blood stream and is carried away by venous blood leaving the eye.

With reference to FIG. 3A, it will be appreciated that Schlemm's canal SC is disposed inside anterior chamber AC. Schlemm's canal SC is a tube-like structure that encircles iris 30. In the illustration of FIG. 3A, the cutting plane passing through the center of pupil 32 has also passed through Schlemm's canal. Accordingly, two laterally cut ends of Schlemm's canal SC are visible in the cross-sectional view of FIG. 3A. In a healthy eye, aqueous humor flows out of anterior chamber AC and into Schlemm's canal SC. Aqueous humor exits Schlemm's canal SC and flows into a number of collector channels. After leaving Schlemm's canal SC, aqueous humor is absorbed into the venous blood stream and carried out of the eye.

Because of the position of Schlemm's canal SC within the anterior chamber AC, a Schlemm's canal access cannula inserted through the cornea 36 and anterior chamber AC is likely to approach the plane of Schlemm's canal at an approach angle that is greater than zero. Thus, for example, when using a curved cannula (such as the one shown in FIG. 2) to deliver an implant into Schlemm's canal, the plane of curvature of the cannula will form a non-zero angle with the plane of Schlemm's canal.

Figure 3B:
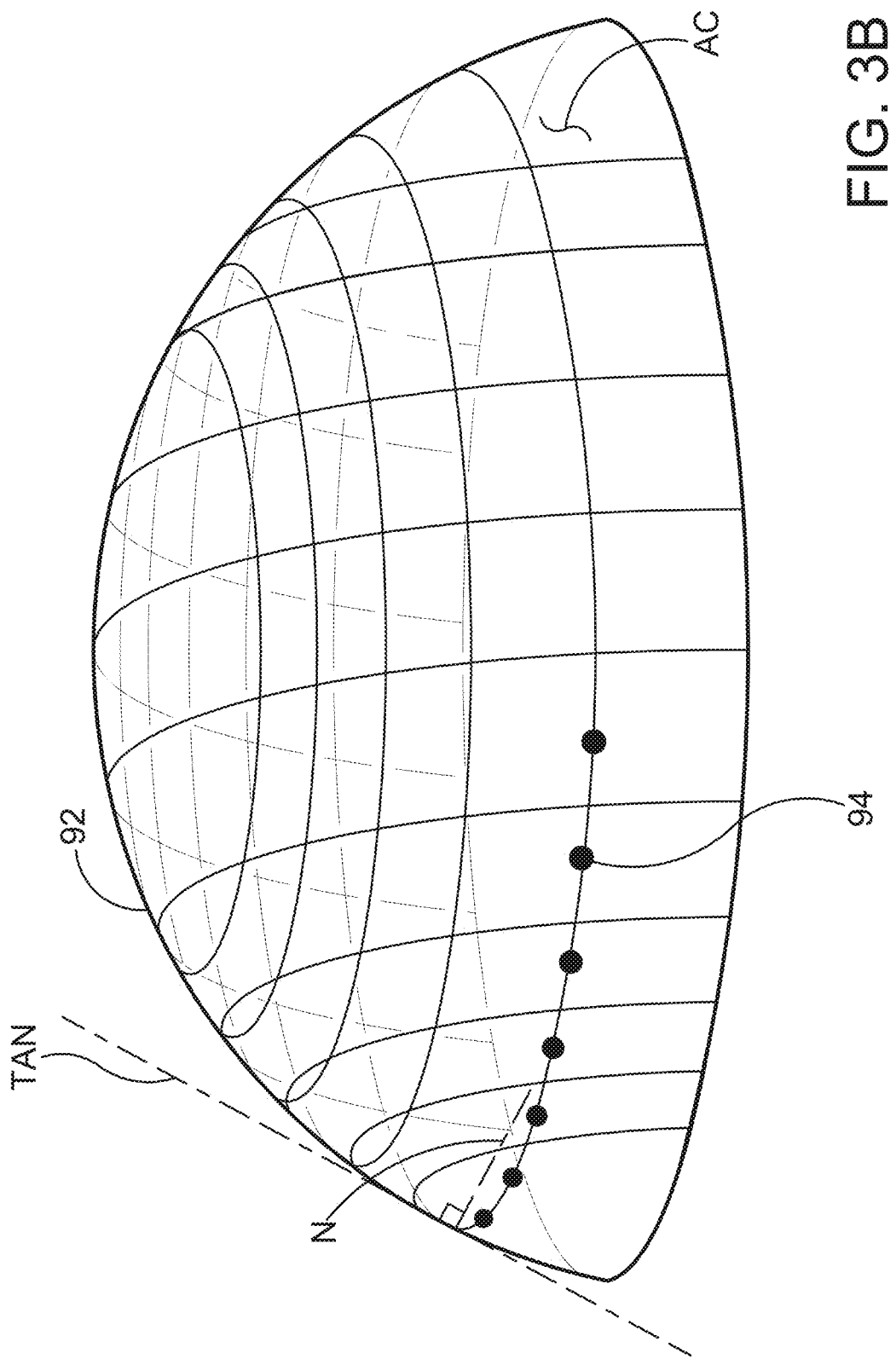
FIG. 3B is a stylized perspective view depicting the surface that defines the anterior chamber of the eye shown in FIG. 3A.

FIG. 3B is a stylized perspective view depicting the surface 92 that defines anterior chamber AC of the eye shown in FIG. 3A. In FIG. 3B, surface 92 is shown having a generally hemispherical shape. FIG. 3B may be used to illustrate some fundamental geometric concepts that will be used below to describe the various ocular implant structures. Geometry is a branch of mathematics concerned with the properties of space and the shape, size, and relative position of objects within that space. In geometry, a sphere is a round object in three-dimensional space. All points on the surface of a sphere are located the same distance r from a center point so that the sphere is completely symmetrical about the center point. In geometry, a point represents an exact location. A point is a zero-dimensional entity (i.e., it has no length, area, or volume). Geometrically speaking, at any point on a spherical surface, one can find a normal direction which is at right angles to the surface. For a spherical surface all normal directions intersect the center point of the sphere. Each normal direction will also be perpendicular to a line that is tangent to the spherical surface. In FIG. 3B, a normal line N is illustrated using dashed lines. Normal line N is at right angles to spherical surface 92. Normal line N is also perpendicular to a reference line TAN. Reference line TAN is tangent to spherical surface 92 in FIG. 3B.

As shown in the previous figure, Schlemm's canal is disposed inside anterior chamber AC. An exemplary method in accordance with this detailed description may include the step of advancing a distal portion of a cannula into the anterior chamber of the eye. The cannula may then be used to access Schlemm's canal, for example, by piercing the wall of Schlemm's canal with the distal end of the cannula. An ocular implant may be advanced out of the distal opening of the cannula and into Schlemm's canal. An exemplary path 94 taken by an ocular implant as it follows Schlemm's canal along surface 92 is illustrated using a row of dots in FIG. 3B.

As the ocular implant advances into Schlemm's canal, the ocular implant may press against the outer major wall of Schlemm's canal and the dome-shaped wall that defines the anterior chamber of the eye. As the body of the ocular implant presses against the dome-shaped wall of the eye, the dome-shaped wall provides support for Schlemm's canal and the ocular implant. The support provided by the dome-shaped wall may be represented by force vectors. The direction of these force vectors may be at right angles to points on the spherical surface that defines the anterior chamber. The dome shaped wall comprises scleral tissue that is firmer than the tissue of Schlemm's canal wall. Accordingly, the outer major wall of Schlemm's canal may be supported by the dome shaped wall as the ocular implant advances into Schlemm's canal.

During delivery, it is desirable that the ocular implant follow the lumen of Schlemm's canal as it is advanced out the distal opening of the cannula. The ability of the ocular implant to be advanced into and follow the lumen of Schlemm's canal may be referred to as trackability. Characteristics of an ocular implant that affect trackability include axial pushability, lateral flexibility, and overall shape with respect to the shape of Schlemm's canal (e.g., radius of curvature and cross-section profile). Axial pushability generally concerns the ability of an ocular implant to transmit to the distal end of the ocular implant an axial force applied to the proximal end of the ocular implant. Lateral flexibility concerns the ease with which the ocular implant body can bend to conform to the shape of the lumen. Trackability may be adversely effected when twisting forces are applied to a curved body. For example, twisting the body of a curved ocular implant about its longitudinal axis may cause the curved body to steer away from a desired path.

Figure 4:
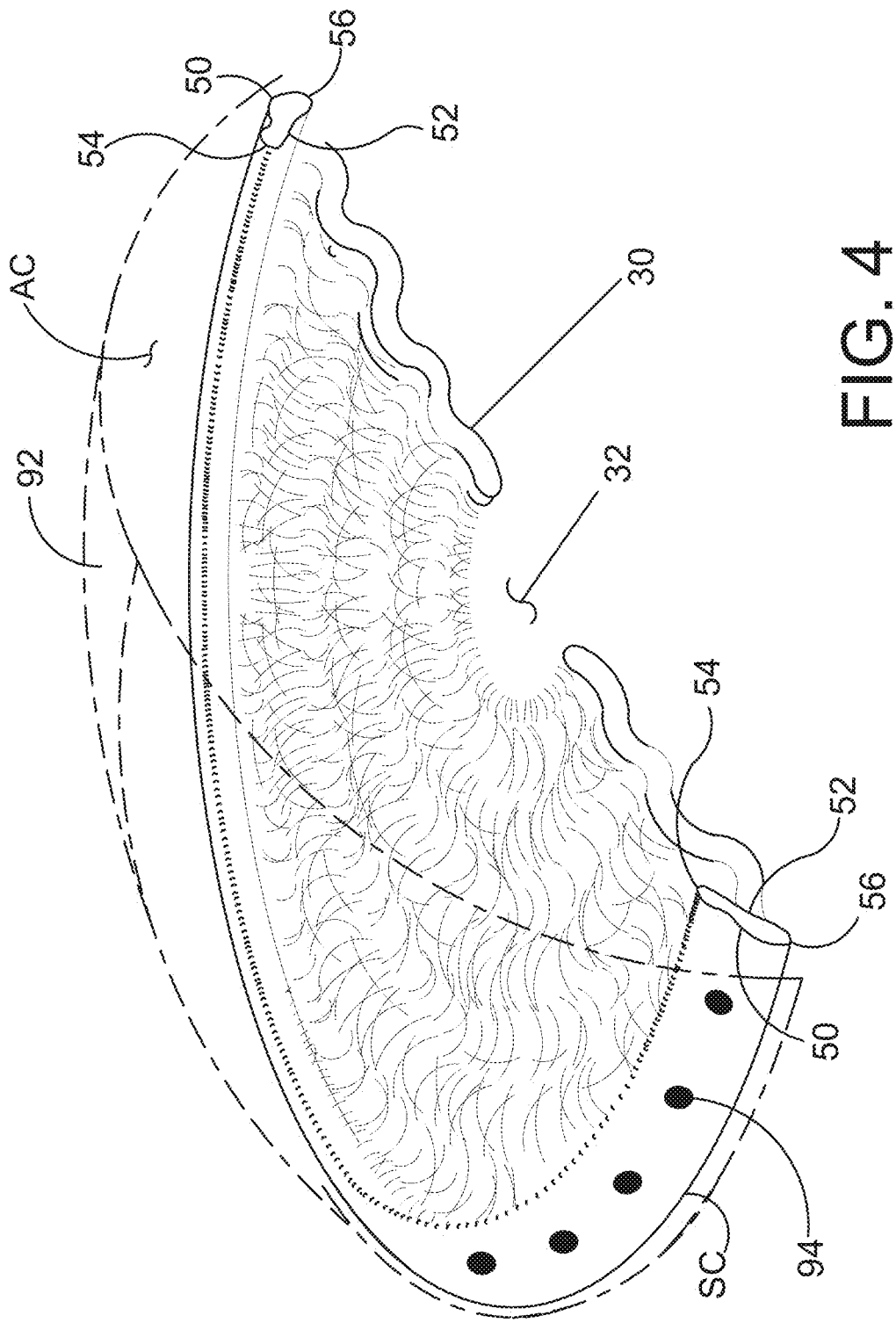
FIG. 4 is a stylized perspective view showing Schlemm's canal and an iris of the eye shown in the previous figure.

FIG. 4 is a stylized perspective view further illustrating Schlemm's canal SC and iris 30 shown in FIG. 3A. Schlemm's canal SC and iris 30 are disposed inside the anterior chamber AC of the eye. The surface 92 that defines the anterior chamber AC of eye 20 is depicted using dashed lines in FIG. 4. In the exemplary embodiment of FIG. 4, Schlemm's canal SC and iris 30 are shown in cross-section, with a cutting plane passing through the center of a pupil 32 defined by iris 30. Schlemm's canal SC comprises a first major side 50, a second major side 52, a first minor side 54, and a second minor side 56. Schlemm's canal SC forms a ring around iris 30 with pupil 32 disposed in the center of that ring. With reference to FIG. 4, it will be appreciated that first major side 50 is on the outside of the ring formed by Schlemm's canal SC and second major side 52 is on the inside of the ring formed by Schlemm's canal SC. Accordingly, first major side 50 may be referred to as an outer major side of Schlemm's canal SC and second major side 52 may be referred to as an inner major side of Schlemm's canal SC. With reference to FIG. 4, it will be appreciated that first major side 50 is further from pupil 32 than second major side 52.

FIG. 22 is an enlarged cross-sectional view further illustrating Schlemm's canal SC. Schlemm's canal SC includes a wall W defining a lumen 58. The shape of Schlemm's canal SC is somewhat irregular, and can vary from patient to patient. The shape of Schlemm's canal SC may be conceptualized as a cylindrical-tube that has been partially flattened. The cross-sectional shape of lumen 58 may be compared to the shape of an ellipse. A major axis 60 and a minor axis 62 of lumen 58 are illustrated with dashed lines in FIG. 22.

The length of major axis 60 and minor axis 62 can vary from patient to patient. The length of minor axis 62 is between one and thirty micrometers in most patients. The length of major axis 60 is between one hundred and fifty micrometers and three hundred and fifty micrometers in most patients.

With reference to FIG. 22, Schlemm's canal SC has a first major side 50, a second major side 52, a first minor side 54, and a second minor side 56. In the exemplary embodiment of FIG. 22, first major side 50 is longer than both first minor side 54 and second minor side 56. Also in the exemplary embodiment of FIG. 22, second major side 52 is longer than both first minor side 54 and second minor side 56.

An exemplary path 94 taken by an ocular implant as it follows Schlemm's canal along surface 92 is illustrated using a row of dots in FIG. 4. As the ocular implant advances into Schlemm's canal, the ocular implant may press against the outer major wall of Schlemm's canal and the dome-shaped wall that defines the anterior chamber. More particularly, one or more surfaces (e.g., on the struts) of the ocular implant may press against surface 92, i.e., scleral tissue forming part of the dome-shaped wall of the eye, as the implant moves into and along Schlemm's canal. The scleral tissue provides support for Schlemm's canal and the ocular implant as it is advanced into and along Schlemm's canal.

The support provided by the scleral tissue may be represented by one or more force vectors with each force vector being at right angles to a point on the spherical surface that defines the anterior chamber of the eye; these force vectors act on the implant to balance the forces generated by the implant as the implant is inserted into and advanced along Schlemm's canal.

The interaction between the implant's structure and the tissue forming Schlemm's canal can affect how the implant behaves as it is inserted into and advanced along Schlemm's canal. For example, the implant may have surfaces (hereinafter, "landing surfaces") that engage scleral tissue within Schlemm's canal as the implant is inserted into and advanced along Schlemm's canal. If the force vector on a landing surface on one side of the implant exceeds the force vector on an opposite side of the implant, the implant may bend or twist as it is advanced. In addition, if the implant has a preset curve, any bending or twisting of the implant may direct the curve away from, instead of along, the curve of Schlemm's canal. Also, the implant may have a preferential bending plane that will affect the orientation of the implant within a curved insertion cannula and with the curve of Schlemm's canal as well as the implant's response to force vectors on its landing surfaces.

For example, an ocular implant in accordance with the present detailed description may include a plurality of spines and a plurality of landing surfaces that seat against the inner surface of the dome shaped wall that encloses the anterior chamber so that the dome shaped wall provides supporting normal forces to the landing surfaces. The ocular implant may be configured such that a net twisting moment applied to each spine by the normal forces supporting the landing surfaces during implantation is reduced or is substantially zero. The ocular implant may also be configured such that the normal forces supporting the landing surfaces primarily or exclusively act to guide each spine along the preferential bending plane thereof.

Figure 5A:
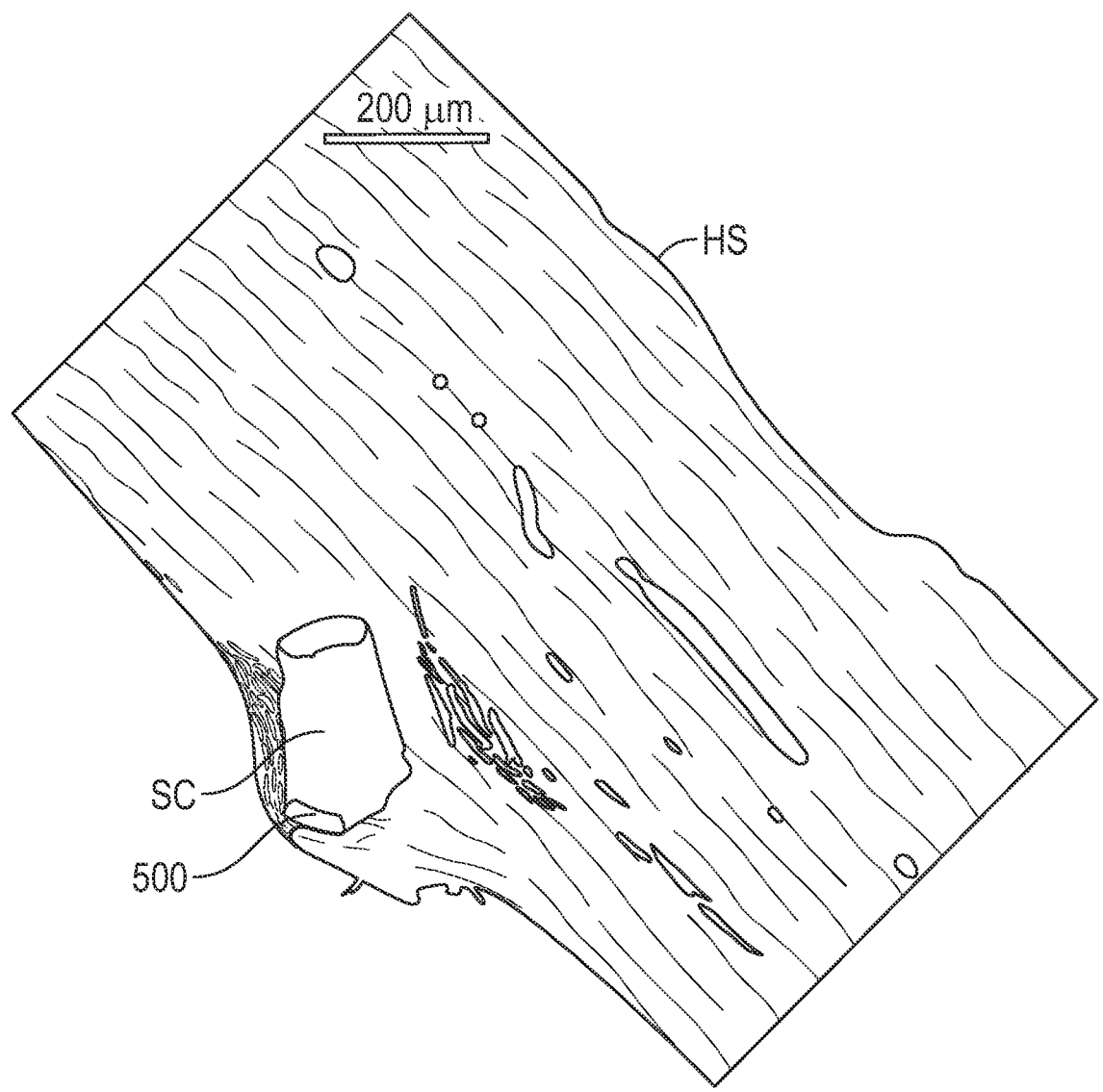
FIG. 5A is a photographic image showing a histology slide HS. Histology slide HS of FIG. 5A was created by sectioning and staining tissue from a cadaveric eye. An ocular implant was implanted in Schlemm's canal of the cadaveric eye prior to sectioning.

FIG. 5A is a photographic image showing a histology slide HS. Histology slide HS of FIG. 5 was created by sectioning and staining tissue sampled from a cadaveric eye. An ocular implant 500 was implanted in Schlemm's canal SC of the cadaveric eye prior to sectioning. The photograph of FIG. 5A was created while examining the section of tissue using a light microscope. FIG. 5B is a drawing of the ocular implant 500 used in FIG. 5A. Similar to the ocular implants described in, e.g., U.S. Pat. No. 7,740,604, US Publ. No. 2009/0082860, U.S. Pat. No. 8,372,026 and US Publ. No. 2011/0009958, implant 500 in FIG. 5B has spines 504 alternating with frames 506. The spines and frames have curved cross-sections, and the circumferential extent of the spine cross-section is less than the circumferential extent of the frame cross-section. Implant 500 extends along a curved longitudinal axis, and its curvature plane bisects spines 504. Each frame 506 has two struts 508 extending equally from the curvature plane and, therefore, equally from the spines on either side of that frame. Optional openings 510 are formed in each frame. Openings 510 communicate with a channel 532 extending along implant 500. Channel 532 has an opening 534 along one side and extending through the spines and frames. An inlet portion 528 of implant 500 is configured to be disposed in the anterior chamber of the eye when rest of the implant is disposed in Schlemm's canal.

FIG. 6A is a stylized line drawing illustrating histology slide HS shown in the previous figure. FIG. 6B is a simplified cross-sectional view illustrating the eye from which the histology sample was taken. FIG. 6A and FIG. 6B are presented on a single page to illustrate the location of the histology sample relative to other portions of the eye 20. As discussed earlier, eye 20 includes a dome-shaped wall 90 having a surface 92 defining an anterior chamber AC. Dome-shaped wall 90 of eye 20 comprises a cornea 36 and scleral tissue 34. The scleral tissue 34 meets the cornea 36 at a limbus of eye 20. In FIG. 6B, surface 92 is shown having a generally hemispherical shape. In FIG. 6A, ocular implant 500 is shown residing in Schlemm's canal SC.

In some embodiments, as shown in FIG. 2, the implant is inserted from the anterior chamber through the trabecular meshwork into Schlemm's canal. Suitable delivery systems for this ab interno implantation procedure are described in US Publ. No. 2009/0132040, now U.S. Pat. Nos. 8,512,404; 8,337,509; US Publ. No. 2011/0098809; and U.S. application Ser. No. 13/330,592, filed Dec. 19, 2011, now U.S. Pat. No. 8,663,150. As the implant passes through the relatively soft tissue of the trabecular meshwork, landing surfaces of the implant will engage the relatively stiffer scleral tissue bounding Schlemm's canal. The relative position of the landing surfaces with respect to other structure of the implant (and with respect to the structure of Schlemm's canal) will govern how reaction forces on the landing surfaces from this engagement will affect the implant as it is advanced into Schlemm's canal.

Figures 7A, 7B:
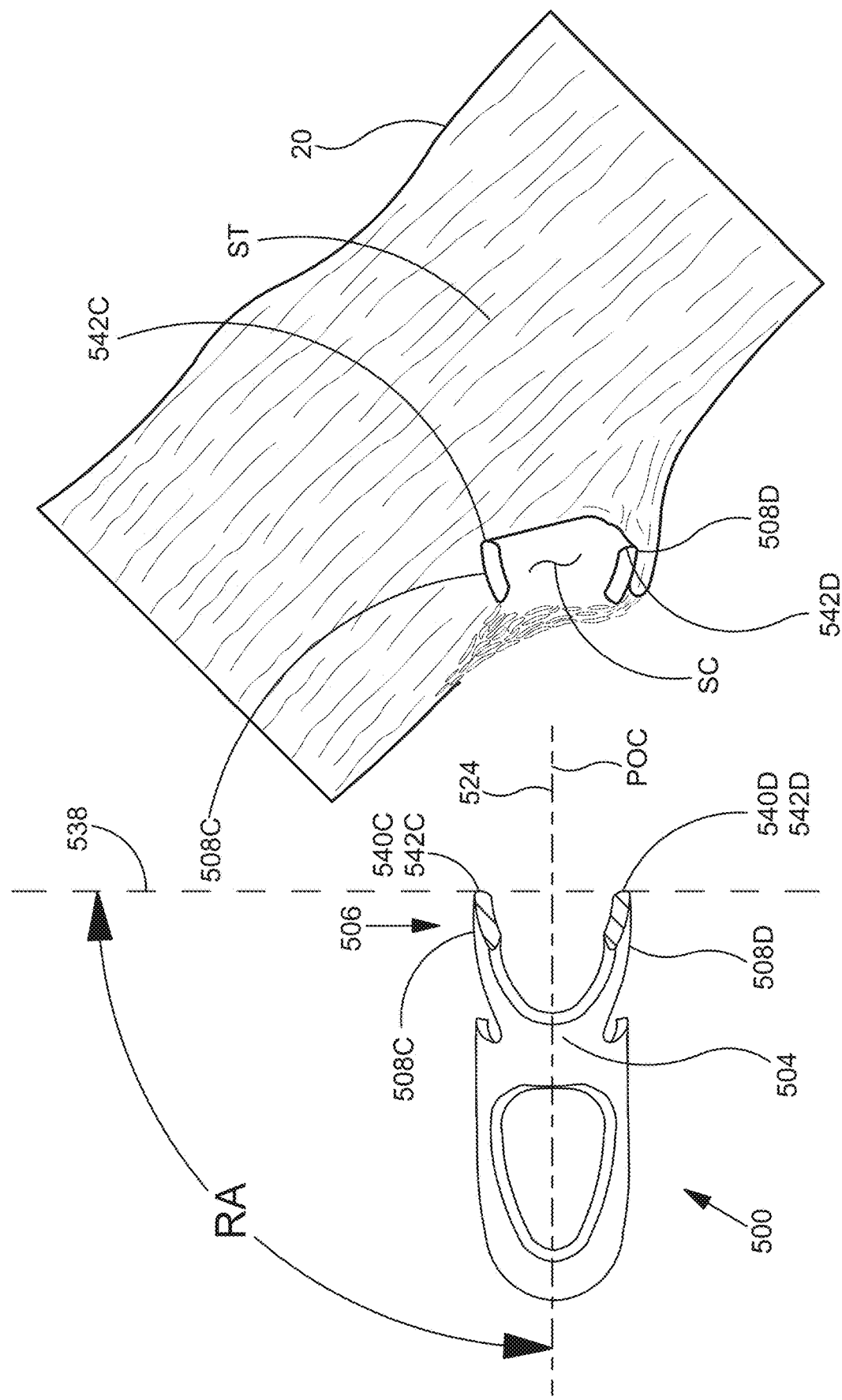
FIG. 7A is a stylized line drawing showing an ocular implant residing in a section of an eye including Schlemm's canal.
FIG. 7B is a section view showing the ocular implant prior to insertion into Schlemm's canal of the eye.
Figure 7C:
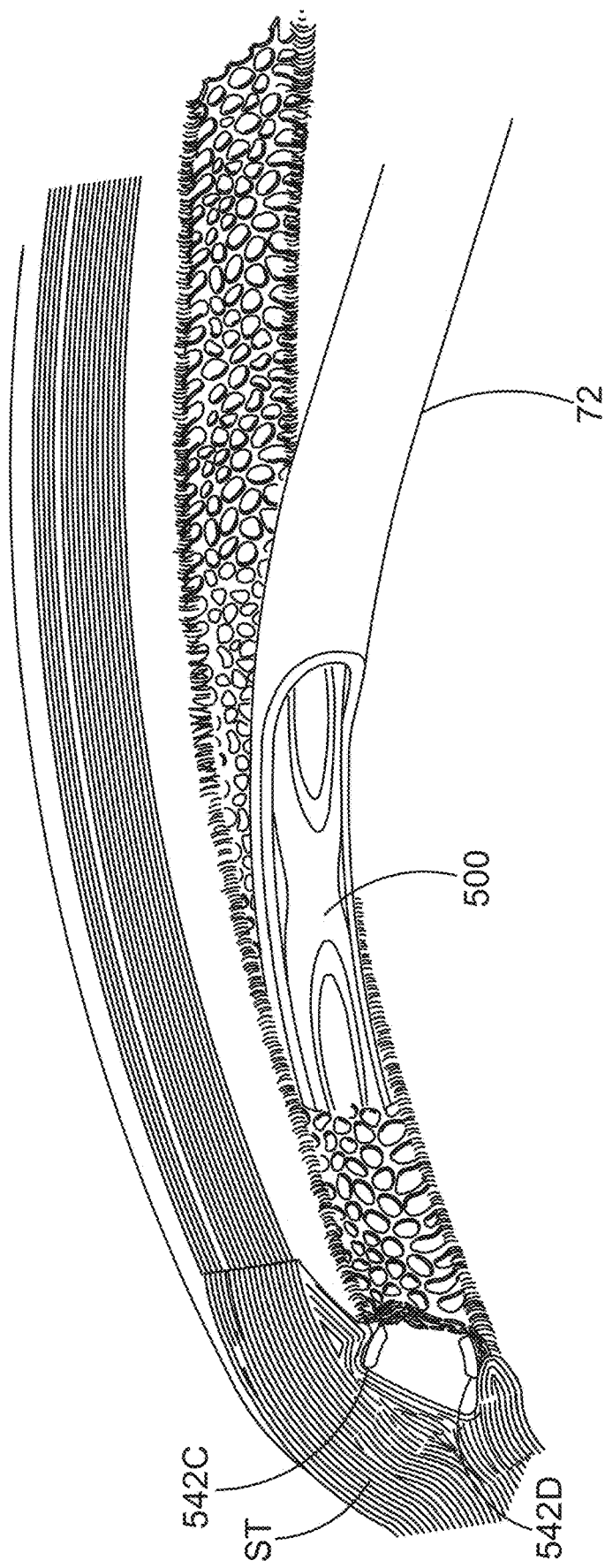
FIG. 7C is a perspective view showing the ocular implant being inserted into Schlemm's canal.

FIG. 7A is a stylized line drawing showing a cross section of an ocular implant 500 residing in a section of an eye 20 including Schlemm's canal SC. FIG. 7B is a section view showing same cross-sectional portion of ocular implant 500 prior to insertion into Schlemm's canal of eye 20. Implant 500 may be, e.g., one of the implants described in U.S. Pat. Nos. 7,740,604; 8,372,026; US 2009/0082860, now U.S. Pat. No. 8,734,377; or US 2011/0009958, now U.S. Pat. No. 8,425,449. In the view shown in FIG. 7B, no external forces are acting on ocular implant 500 so that it is free to assume an undeformed curved shape free of stress and/or strain. FIG. 7C is a perspective view showing the ocular implant 500 being inserted into Schlemm's canal through a cannula 72. FIG. 7A, FIG. 7B and FIG. 7C may be collectively referred to as FIG. 7.

Placing FIG. 7A adjacent to FIG. 7B allows comparisons to be drawn therebetween. By comparing FIG. 7A to FIG. 7B, it will be appreciated that ocular implant 500 is assuming substantially the same orientation in both figures. It is believed that the tissues of the trabecular meshwork are quite soft and compliant, and they do not have sufficient stiffness to hold ocular implant 500 in a twisted orientation different from the orientation that the ocular implant takes when no external forces are acting on it. A twisted implant might therefore not remain in the desired position within Schlemm's canal.

Ocular implant 500 of FIG. 7B includes a spine 504 and a frame 506. In the exemplary embodiment of FIG. 7B, frame 506 comprises a first strut 508C and a second strut 508D. As shown, struts 508C and 508D both extend circumferentially beyond the circumferential extent of spine 504. First strut 508C and second strut 508D comprise a first landing surface 542C and a second landing surface 542D, respectively.

As shown in FIG. 7C, the implant will engage Schlemm's canal tissue as it is inserted into and advanced along Schlemm's canal. The force vectors from engagement of the implant with scleral tissue partially bordering Schlemm's canal depend on the relative orientation of landing surfaces and scleral tissue with respect to the direction of insertion, which in turn depends on the orientation of the implant within the cannula and the relative positions of the landing surfaces on the implant. As shown in FIG. 7C, during insertion of implant 500 into Schlemm's canal, landing surface 542C is engaging the scleral tissue ST bordering Schlemm's canal more directly than its corresponding landing surface 542D. This mismatch in engagement may result in the generation of different reaction forces on landing surfaces 542C and 542D and may apply bending or twisting moments to the implant that will twist implant 500 to move landing surface 542D toward (and perhaps against) scleral tissue ST. The invention described below reduces this bending or twisting moment.

With reference to FIG. 7, it will be appreciated that first landing surface 542C of first strut 508C and second landing surface 542D of second strut 508D define a footprint line 538. Footprint line 538 contacts ocular implant 500 at a first point 540C and a second point 540D. First point 540C is disposed on first landing surface 542C of first strut 508C. Second point 540D is disposed on second landing surface 542D of second strut 508D.

A plane 524 is shown intersecting ocular implant 500 in FIG. 7B. In the embodiment of FIG. 7B, the longitudinal axis of ocular implant 500 follows a curved path so that the longitudinal axis defines a plane of curvature POC that bisects spines 504 and frames 506 and is co-planar with plane 524 shown in FIG. 7B. A roll angle RA of frame 506 is illustrated using angular dimension lines in FIG. 7B. Roll angle RA extends between plane 524 and footprint line 538. In the embodiment of FIG. 7B, because corresponding struts 508C and 508D extend equal distances from the plane of curvature, roll angle RA has a magnitude of about ninety degrees. Also in the embodiment of FIG. 7B, footprint line 538 is generally orthogonal to the plane of curvature POC of ocular implant 500.

As an ocular implant advances into Schlemm's canal during a delivery procedure, the ocular implant may press against the dome-shaped wall that defines the anterior chamber. More particularly, one or more struts of the ocular implant may press against scleral tissue forming part of the dome-shaped wall of the eye. Landing surfaces of the ocular implant may be seated against the outer wall of Schlemm's canal and the scleral tissue as it is advanced into Schlemm's canal. The scleral tissue may provide support for the outer wall of Schlemm's canal as the ocular implant is advanced therein. These supporting reaction forces will act against the ocular implant as the implant engages the wall of Schlemm's canal.

For example, as discussed above with respect to FIGS. 7A and 7C, as the ocular implant moves out of delivery cannula 72 into Schlemm's canal, first landing surface 542C of first strut 508C engages scleral tissue ST. Because of the slope of the inside back wall of Schlemm's canal, and the equal heights of the implant struts within the implant's plane of curvature, the impact force vector normal to the insertion path of the first landing surface 542C against scleral tissue is greater than the impact force vector normal to the insertion path of the second landing surface 542D against scleral tissue. The reaction forces from the scleral tissue against implant 500 may therefore cause a twisting or bending of implant 500 as it is advanced into Schlemm's canal that move landing surface 542 D toward, and perhaps against, scleral tissue ST.

Changing the angle of the insertion cannula with respect to the plane of Schlemm's canal would change the way the implant's landing surfaces interact with scleral tissue during insertion and, therefore, any bending or twisting moments applied to the implant. Visualization requirements and anterior chamber access limitations may require the cannula to form an angle greater than zero with the plane of Schlemm's canal. It therefore may be desirable to change the position of the implant landing surfaces in an effort to reduce the difference in the magnitude of the reaction forces on landing surfaces on opposite sides of the implant, such as by changing the relative heights of the struts with respect to the implant's plane of curvature.

Figures 8A, 8B:
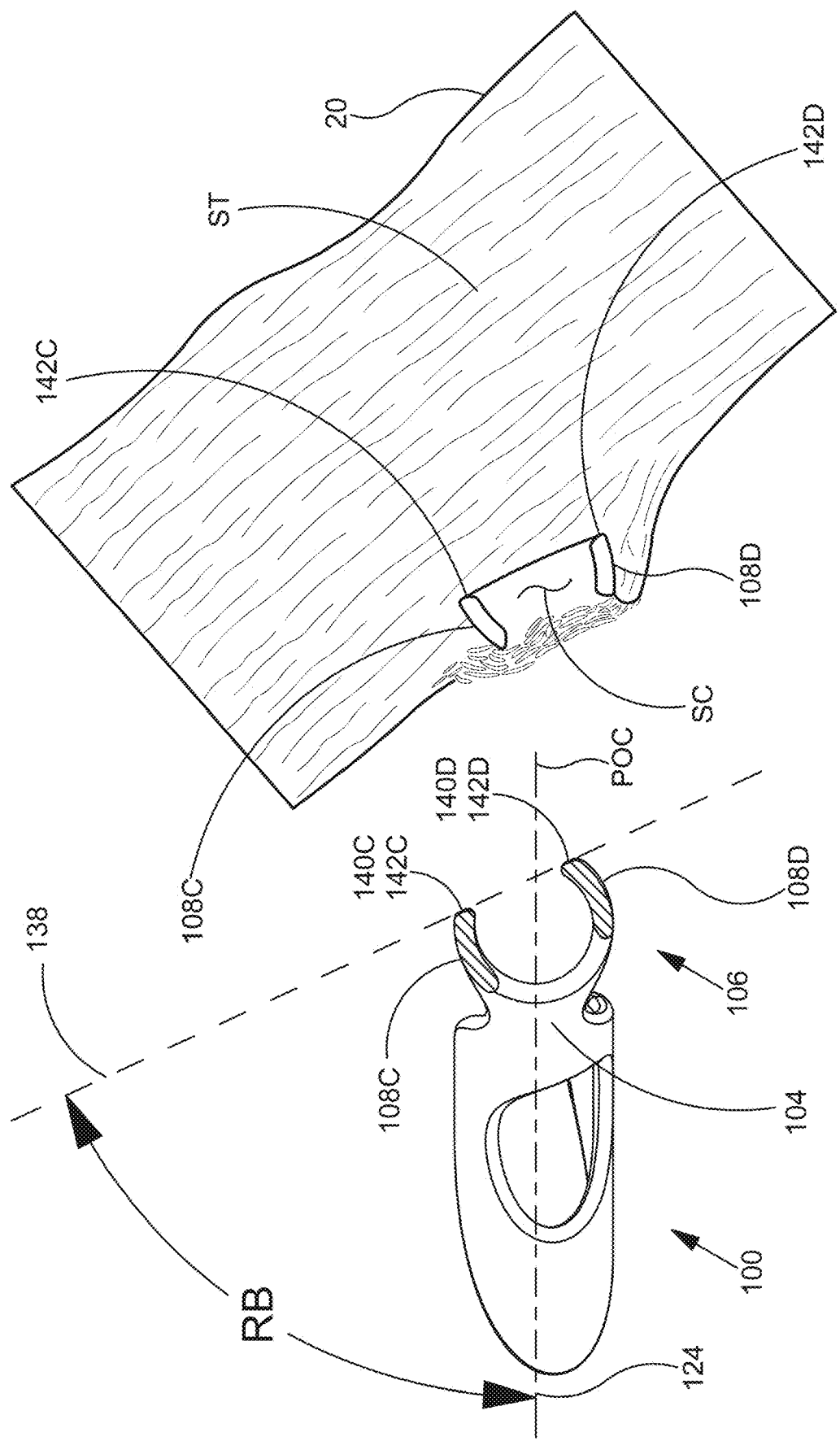
FIG. 8A is a stylized line drawing showing an ocular implant according to the detailed description residing in a section of an eye including Schlemm's canal.
FIG. 8B is a section view showing the ocular implant of Figure A prior to insertion into Schlemm's canal of the eye.
Figure 8C:
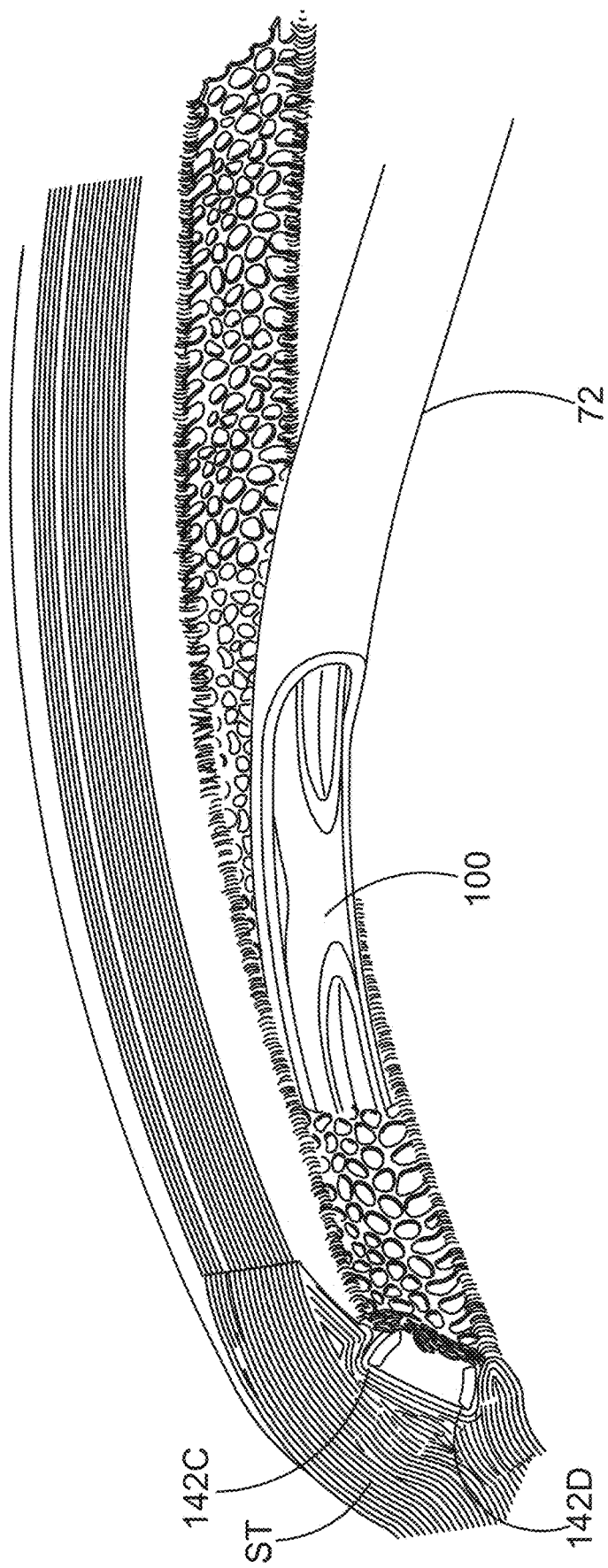
FIG. 8C is a perspective view showing the ocular implant of FIGS. 8A and 8B being inserted into Schlemm's canal.

FIG. 8A is a stylized line drawing showing an ocular implant 100 residing in a section of an eye 20 including Schlemm's canal SC. FIG. 8B is a section view showing a portion of ocular implant 100 prior to insertion into Schlemm's canal of eye 20. FIG. 8C is a perspective view showing the ocular implant 100 being inserted into Schlemm's canal through a cannula 72. In the view shown in FIG. 8B, no external forces are acting on ocular implant 100 so that it is free to assume an undeformed shape free of stress and/or strain. By comparing FIG. 8A to FIG. 8B, it will be appreciated that ocular implant 100 is assuming substantially the same orientation in both figures. As mentioned above, the tissues of the trabecular meshwork are quite soft and compliant, and they and do not have sufficient stiffness to hold ocular implant 100 in a twisted orientation different from the orientation that the ocular implant takes when no external forces are acting on it.

Ocular implant 100 of FIG. 8B includes a spine 104 and a frame 106. In the exemplary embodiment of FIG. 8B, frame 106 comprises a first strut 108C and a second strut 108D. As shown, struts 108C and 108D both extend circumferentially beyond the circumferential extent of spine 104. First strut 108C and second strut 108D comprise a first landing surface 142C and a second landing surface 142D, respectively. With reference to FIG. 8, it will be appreciated that first landing surface 142C of first strut 108C and second landing surface 142D of second strut 108D define a footprint line 138. Footprint line 138 contacts ocular implant 100 at a first point 140C and a second point 140D. First point 140C is disposed on first landing surface 142C of first strut 108C. Second point 140D is disposed on second landing surface 142D of second strut 108D.

A plane 124 is shown intersecting ocular implant 100 in FIG. 8B. In the embodiment of FIG. 8B, the longitudinal axis of ocular implant 100 follows a curved path so that the longitudinal axis defines a plane of curvature POC that is co-planar with plane 124 shown in FIG. 8B. As shown in FIG. 8B, the plane of curvature POC bisects spine 104 so that the cross-sectional circumferential extent of spine 104 on one side of the plane of curvature is substantially equal to the cross-sectional circumferential extent of spine 104 on the other side of the plane of curvature.

During implantation, the implant 100 will be oriented with the curved insertion cannula 72, as suggested by FIG. 8C, such that the implant's plane of curvature is coplanar with the cannula's plane of curvature. Thus, adjusting the height of the struts with respect to the implant's plane of curvature and curved longitudinal axis will affect the way that the implant's landing surfaces engage scleral tissue as the implant is advanced into and along Schlemm's canal.

A roll angle RB of frame 106 is illustrated using angular dimension lines in FIG. 8B. Roll angle RB extends between plane 124 and footprint line 138. By comparing FIG. 8B with FIG. 7B described above, it will be appreciated that because strut 108D extends further out of the plane of curvature than its opposing strut 108C, the roll angle RB shown in FIG. 8B has a magnitude different from the magnitude of roll angle RA shown in FIG. 7B. In the embodiment of FIG. 8B, angle RB has a magnitude other than ninety degrees. Also in the embodiment of FIG. 8B, footprint line 138 is generally skewed relative to the plane of curvature POC of ocular implant 100.

Differences in the responses of implant 100 and implant 500 can be seen by comparing FIG. 8 to FIG. 7. As shown in FIGS. 8A and 8C, as the ocular implant 100 moves out of delivery cannula 72 into Schlemm's canal, landing surfaces 142C and 142D engage scleral tissue ST. Because of the slope of the inside back wall of Schlemm's canal and the unequal heights of the implant struts with respect to the implant's plane of curvature, the impact force vector normal to the insertion path of the first landing surface 142C against scleral tissue is closer to (and possibly equal to) the impact force vector normal to the insertion path of the second landing surface 142D against scleral tissue. The decrease in the difference between the reaction forces on opposite sides of the implant will decrease any bending or twisting moments applied to implant 100 during insertion and advancement within Schlemm's canal.

FIG. 9 is a perspective view showing ocular implant 500 of FIG. 7. With reference to FIG. 9, it will be appreciated that ocular implant 500 defines a cylindrical surface CYL enclosing a three dimensional volume having a shape similar to a cylinder. Ocular implant 500 of FIG. 9 includes a spine 504 and a frame 506. In the exemplary embodiment of FIG. 9, frame 506 comprises a first strut 508C and a second strut 508D. First strut 508C and second strut 508D comprise a first landing surface 542C and a second landing surface 542D, respectively. With reference to FIG. 7, it will be appreciated that first landing surface 542C of first strut 508C and second landing surface 542D of second strut 508D define a footprint line 538. Footprint line 538 contacts ocular implant 500 at a first point 540C and a second point 540D. First point 540C is disposed on first landing surface 542C of first strut 508C. Second point 540D is disposed on second landing surface 542D of second strut 508D. With reference to FIG. 9, it will be appreciated that footprint line 538 lies on the cylindrical surface CYL defined by ocular implant 500.

FIG. 10 is an additional perspective view showing ocular implant 100 of FIG. 8. With reference to FIG. 10, it will be appreciated that ocular implant 100 defines a conical surface C enclosing a three dimensional volume having a shape similar to a cone. Ocular implant 100 of FIG. 10 includes a spine 104 and a frame 106. In the exemplary embodiment of FIG. 10, frame 106 comprises a first strut 108C and a second strut 108D. First strut 108C and second strut 108D comprise a first landing surface 142C and a second landing surface 142D, respectively. With reference to FIG. 7, it will be appreciated that first landing surface 142C of first strut 108C and second landing surface 142D of second strut 108D define a footprint line 138. Footprint line 138 contacts ocular implant 100 at a first point 140C and a second point 140D. First point 140C is disposed on first landing surface 142C of first strut 108C. Second point 140D is disposed on second landing surface 142D of second strut 108D. With reference to FIG. 10, it will be appreciated that footprint line 138 lies on the conical surface C defined by ocular implant 100.

FIG. 11A is a stylized perspective view showing a conical surface C that is sized and positioned so as to intersect a hemispherical surface S in two places. A first line L1 is formed where the two surfaces intersect a first time. A second line L2 is formed where conical surface C and hemispherical surface S intersect a second time. A first point 142A is positioned on first line L1 and a second point 142B is disposed on second line L2.

FIG. 11B is a stylized perspective view showing the ocular implant 100 of FIG. 8 disposed inside a chamber V defined by a hemispherical surface S. Ocular implant 100 contacts hemispherical surface S at a first point 140A, a second point 140B, a third point 140C, a fourth point 140D, a fifth point 140E, and a sixth point 140F. First point 140A is disposed on a first landing surface 142A of ocular implant 100. Second point 140B is disposed on a second landing surface 142B of ocular implant 100. Third point 140C and fourth point 140D are disposed on a third landing surface 142C and a fourth landing surface 142D, respectively. Fifth point 140E and sixth point 140F are disposed on a fifth landing surface 142E and a sixth landing surface 142F, respectively.

Applicant has created ocular implants designed to work in harmony with the dome shaped wall that defines the anterior chamber of the human eye. In some useful embodiments, the ocular implants are configured such that reaction forces applied to the ocular implant by scleral tissue while the ocular implant is being advanced into Schlemm's canal subject the ocular implant to pure bending with little or no twisting. The ocular implant may be configured such that a net twisting moment applied to each spine by the normal forces supporting the landing surfaces is substantially zero. The ocular implant may also be configured such that the normal forces supporting the landing surfaces primarily or exclusively act to bend each spine along the preferential bending plane thereof.

The implant will bend preferentially about the region having the smallest circumferential extent, i.e., the spine. In the embodiment shown FIGS. 8, 10 and 11B, because the spines extend equally on both sides of the plane of curvature POC, the plane of curvature and the preferential bending plane are coplanar. If the roll angle of the implant is set so that the normal forces on the strut landing surfaces are substantially equal (i.e., the angle of the footprint equals the angle of the back wall of Schlemm's canal), the net forces on the implant during insertion and advancement will cause the implant to bend along its preferential bending plane with no net twisting about the plane. In some other useful embodiments (discussed below with respect to FIGS. 15-18 and 19B), the preferential bending plane of each spine extends in a direction that is at right angles to a conical surface defined by the ocular implant.

In the embodiment of FIG. 11B, ocular implant 100 defines a conical surface C. Ocular implant 100 contacts conical surface C at a first point 140A, a second point 140B, a third point 140C, a fourth point 140D, a fifth point 140E, and a sixth point 140F. Due to page size constraints, conical surface C is truncated in FIG. 21. Conical surface C intersects hemispherical surface S in two places. First point 140A, third point 140C, and fifth point 140E are disposed on a first line formed where conical surface C and hemispherical surface S intersect a first time. Second point 140B, fourth point 140D, and sixth point 140F are disposed on a second line formed where the two surfaces intersect a second time.

Figure 12A:
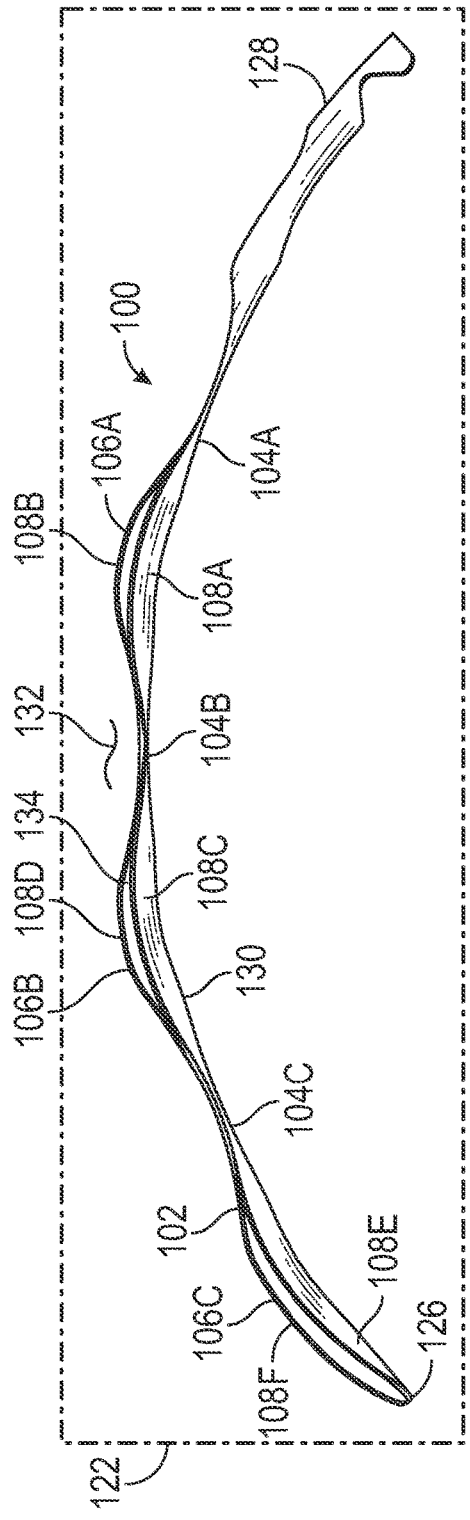
FIG. 12A, FIG. 12B and FIG. 12C are plan views of the ocular implant of FIG. 8 created using multiview projection.
Figure 12B:
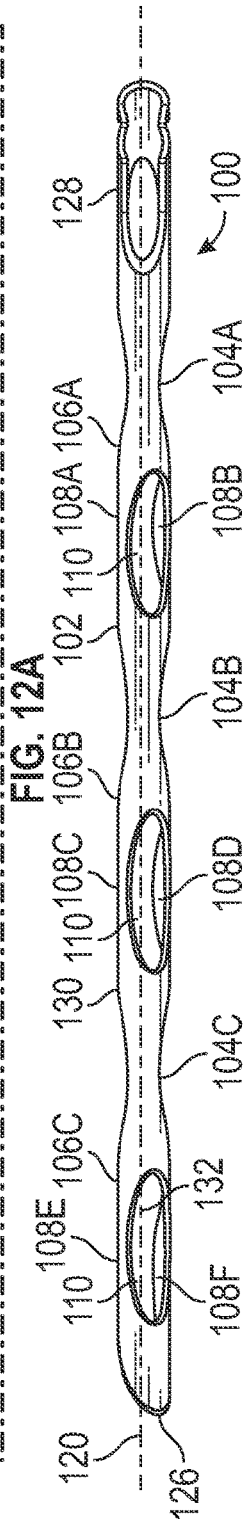
Figure 12C:
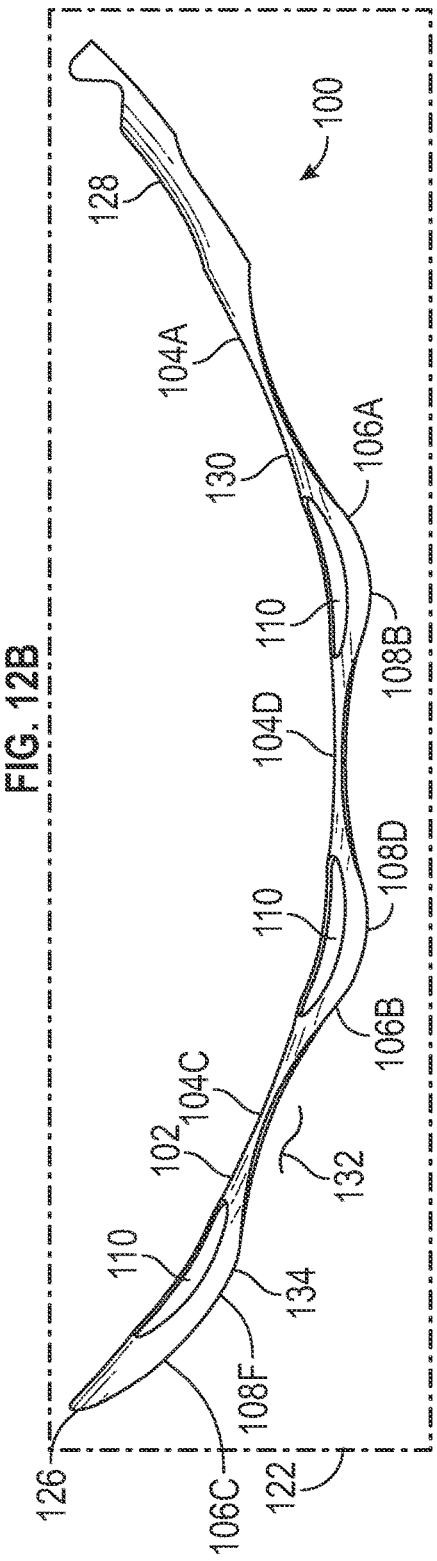

FIG. 12A, FIG. 12B and FIG. 12C are plan views of the ocular implant 100 of FIG. 8 created using multiview projection. FIG. 12A, FIG. 12B and FIG. 12C may be referred to collectively as FIG. 12. It is customary to refer to multiview projections using terms such as front view, top view, and side view. In accordance with this convention, FIG. 12A may be referred to as a top view of ocular implant 100, FIG. 12B may be referred to as a side view of ocular implant 100, and FIG. 12C may be referred to as a bottom view of ocular implant 100. The terms top view, side view, and bottom view are used herein as a convenient method for differentiating between the views shown in FIG. 12. It will be appreciated that the implant shown in FIG. 12 may assume various orientations without deviating from the spirit and scope of this detailed description. Accordingly, the terms top view, side view, and bottom view should not be interpreted to limit the scope of the invention recited in the attached claims.

Ocular implant 100 of FIG. 12 comprises a body 102 that extends along a longitudinal central axis 120. In the exemplary embodiment of FIG. 12, longitudinal central axis 120 follows a curved path such that longitudinal central axis 120 defines a curvature plane 122. In some useful embodiments, the radius of curvature of the ocular implant is substantially equal to the radius of curvature of Schlemm's canal. Body 102 of ocular implant 100 has a distal end 126, a proximal inlet portion 128 and an intermediate portion 130 extending between the proximal inlet portion 128 and the distal end 126. Intermediate portion 130 comprises a plurality of spines 104 and a plurality of frames 106. The spines 104 of intermediate portion 130 include a first spine 104A, a second spine 104B and a third spine 104C. The frames 106 of intermediate portion 130 include a first frame 106A, a second frame 106B and a third frame 106C. Ocular implant 100 is sized and configured so that the spines and frames are disposed in and supporting Schlemm's canal and the inlet 128 is disposed in the anterior chamber to provide for flow of aqueous humor from the anterior chamber through Schlemm's canal to outflow channels communicating with Schlemm's canal.

In FIG. 12, first spine 104A can be seen extending distally beyond proximal inlet portion 128. First frame 106A comprises a first strut 108A and a second strut 108B that extend between first spine 104A and second spine 104B. With reference to FIG. 12, it will be appreciated that second frame 106B abuts a distal end of second spine 104B. In the embodiment of FIG. 12, second frame 106B comprises a first strut 108C and a second strut 108D that extend between second spine 104B and third spine 104C. Third frame 106C can be seen extending between third spine 104C and distal end 126 of ocular implant 100 in FIG. 12. Third frame 106C comprises a first strut 108E and a second strut 108F.

Body 102 of ocular implant 100 defines a channel 132 that opens into a channel opening 134. With reference to FIG. 12, it will be appreciated that channel 132 and channel opening 134 extending together through body 102 across first spine 104A, second spine 104B, third spine 104C, first frame 106A, second frame 106B, and third frame 106C. Optional additional openings 110 communicating with channel 132 are disposed between the spines and are surrounded by the struts.

With particular reference to FIG. 12B, it will be appreciated that curvature plane 122 intersects first spine 104A, second spine 104B, and third spine 104C. In the embodiment of FIG. 12A, curvature plane 122 bisects each spine into two halves. The two halves of each spine are symmetrically shaped about curvature plane 122 in the embodiment of FIG. 12A. With reference to FIG. 12B and FIG. 12C, it will be appreciated that the frames of ocular implant 100 are not symmetric about curvature plane 122.

FIG. 13A is a plan view showing ocular implant 100 of FIG. 8. FIG. 13B is an enlarged section view taken along section line B-B shown in FIG. 13A. FIG. 13C is an additional enlarged section view taken along section line C-C shown in FIG. 13A. FIG. 13A, FIG. 13B and FIG. 13C may be collectively referred to as FIG. 13.

Ocular implant 100 of FIG. 13 comprises a body 102 that extends along a longitudinal central axis 120. Body 102 of ocular implant 100 has a distal end 126, a proximal inlet portion 128 and an intermediate portion 130 extending between the proximal inlet portion 128 and the distal end 126. Intermediate portion 130 comprises a plurality of spines 104 and a plurality of frames 106. The spines 104 of intermediate portion 130 include a first spine 104A, a second spine 104B and a third spine 104C. The frames 106 of intermediate portion 130 include a first frame 106A, a second frame 106B and a third frame 106C.

In FIG. 13, first spine 104A can be seen extending distally beyond proximal inlet portion 128. First frame 106A comprises a first strut 108A and a second strut 108B that extend between first spine 104A and second spine 104B. With reference to FIG. 13, it will be appreciated that second frame 106B abuts a distal end of second spine 104B. In the embodiment of FIG. 13, second frame 106B comprises a first strut 108C and a second strut 108D that extend between second spine 104B and third spine 104C. Third frame 106C can be seen extending between third spine 104C and distal end 126 of ocular implant 100 in FIG. 13. Third frame 106C comprises a first strut 108E and a second strut 108F.

Body 102 of ocular implant 100 defines a channel 132 that opens into a channel opening 134. With particular reference to FIG. 13A, it will be appreciated that channel 132 and channel opening 134 extending together through body 102 across first spine 104A, second spine 104B, third spine 104C, first frame 106A, second frame 106B, and third frame 106C. In this embodiment, the struts on one side of the implant extend further out of the plane of curvature that their corresponding struts on the opposite side of the implant. Thus, as shown in FIG. 13B, strut 108F extends further out of the plane of curvature (corresponding with longitudinal central axis 120) than its opposing strut 108E.

Figure 14A:
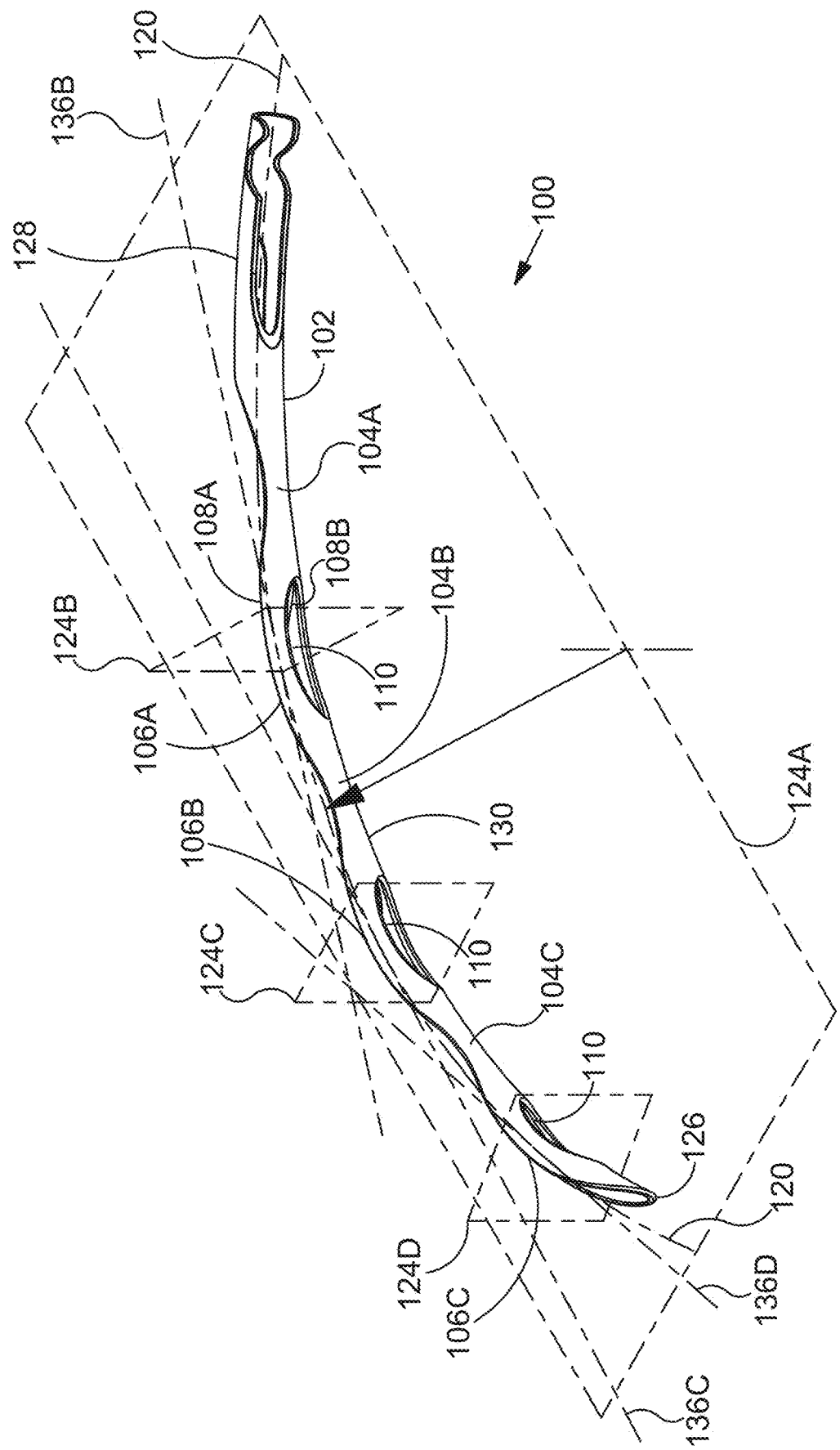
FIG. 14A is a perspective view showing the ocular implant of FIG. 8. A first plane and a second plane are shown intersecting the ocular implant in FIG. 14A.

FIG. 14A is a perspective view showing ocular implant 100 of FIG. 8. Ocular implant 100 comprises a body 102 extending along a longitudinal central axis 120. A first plane 124A is shown intersecting ocular implant 100 in FIG. 14A. In the embodiment of FIG. 14A, longitudinal central axis 120 follows a path that is generally curved such that longitudinal central axis 120 defines a plane of curvature that is co-planar with first plane 124A shown in FIG. 14A. A second plane 124B, a third plane 124C, and a fourth plane 124D are also shown intersecting ocular implant 100 in FIG. 14A. Second plane 124B, third plane 124C, and fourth plane 124D are all transverse to ocular implant 100 and longitudinal central axis 120 in the embodiment of FIG. 14A. More particularly, in the exemplary embodiment of FIG. 14A, second plane 124B is orthogonal to a reference line 136B that lies in first plane 124A and is tangent to longitudinal central axis 120. Third plane 124C is orthogonal to a reference line 136C that lies in first plane 124A and is tangent to longitudinal central axis 120. Third plane 124D is orthogonal to a reference line 136D that lies in first plane 124A and is tangent to longitudinal central axis 120.

Body 102 of ocular implant 100 has a distal end 126, a proximal inlet portion 128 and an intermediate portion 130 extending between the proximal inlet portion 128 and the distal end 126. Intermediate portion 130 comprises a plurality of spines 104 and a plurality of frames 106. The frames 106 of intermediate portion 130 include a first frame 106A, a second frame 106B and a third frame 106C. In FIG. 14A, second plane 124B is shown extending through first frame 106A. Third plane 124C and fourth plane 124D are shown extending through second frame 106B and third frame 106C, respectively, in FIG. 14A.

The spines 104 of intermediate portion 130 include a first spine 104A, a second spine 104B and a third spine 104C. In FIG. 14, first spine 104A can be seen extending distally beyond proximal inlet portion 128. First frame 106A comprises a first strut 108A and a second strut 108B that extend between first spine 104A and second spine 104B. With reference to FIG. 14, it will be appreciated that second frame 106B abuts a distal end of second spine 104B. In the embodiment of FIG. 14, second frame 106B comprises a third strut and a fourth strut that extend between second spine 104B and third spine 104C. Third frame 106C can be seen extending between third spine 104C and distal end 126 of ocular implant 100 in FIG. 14. Third frame 106C comprises a fifth strut and a sixth strut.

With reference to FIG. 14A, it will be appreciated that first plane 124A intersects the spines of ocular implant 100. In the embodiment of FIG. 14A, first plane 124A bisects each spine into two halves. The two halves of each spine are symmetrically shaped about first plane 124A in the embodiment of FIG. 14A.

In the exemplary embodiment of FIG. 14A, each frame 106 comprises two struts. In some useful embodiments, each strut includes a landing surface and each frame is configured to support the spines in a location offset from an outer major side of Schlemm's canal while the ocular implant is in Schlemm's canal and the landing surfaces are engaging the outer major side of Schlemm's canal. In the embodiment of FIG. 14A, first frame 106A, second frame 106B and third frame 106C are each oriented at a roll angle.

First frame 106A of FIG. 14A comprises a first strut 108A and a second strut 108B. The roll angle of first frame 106A may be defined by a footprint line defined by a first landing surface of first strut 108A and a second landing surface of second strut 108B. In the embodiment of FIG. 14A, the footprint line will lie in second plane 124B and be skewed relative to first plane 124A. The angle between the footprint line and first plane 124A may be referred to as the roll angle of the frame. In the exemplary embodiment of FIG. 14A, second frame 106B and third frame 106C have roll angles similar to the roll angle of first frame 106A.

FIG. 14B is a plan view further illustrating first frame 106A and second plane 124B shown in FIG. 14A. With reference to FIG. 14B, it will be appreciated that first frame 106A has a lateral cross-sectional shape F that lies in second plane 124B. First frame 106A comprises a first strut 108A and a second strut 108B. First plane 124A is shown intersecting first frame 106A in FIG. 14B.

A roll angle RA of first frame 106A is illustrated using angular dimension lines in FIG. 14B. Roll angle RA extends between first plane 124A and a first footprint line 138A. In the exemplary embodiment of FIG. 14, first footprint line 138A is defined by a first point 140A and a second point 140B. First point 140A is disposed on a first landing surface 142A of first strut 108A. Second point 140B is disposed on a second landing surface 142B of second strut 108B. As discussed above, in this embodiment the struts on one side of the implant extend further out of the plane of curvature than their corresponding struts on the opposite side of the implant. Thus, as shown in FIG. 14B, strut 108B extends further out of the plane of curvature 124A than its opposing strut 108A.

FIG. 15A, FIG. 15B and FIG. 15C are multi-plan views of yet another exemplary ocular implant 300 in accordance with the present detailed description. FIG. 15A, FIG. 15B and FIG. 15C may be referred to collectively as FIG. 15. It is customary to refer to multi-view projections using terms such as front view, top view, and side view. In accordance with this convention, FIG. 15A may be referred to as a top view of ocular implant 300, FIG. 15B may be referred to as a side view of ocular implant 300, and FIG. 15C may be referred to as a bottom view of ocular implant 300. The terms top view, side view, and bottom view are used herein as a convenient method for differentiating between the views shown in FIG. 15. It will be appreciated that the implant shown in FIG. 15 may assume various orientations without deviating from the spirit and scope of this detailed description. Accordingly, the terms top view, side view, and bottom view should not be interpreted to limit the scope of the invention recited in the attached claims.

Ocular implant 300 of FIG. 15 comprises a body 302 that extends along a longitudinal central axis 320. In the exemplary embodiment of FIG. 15, longitudinal central axis 320 follows a curved path such that longitudinal central axis 320 defines a curvature plane 322. Body 302 of ocular implant 300 has a distal end 326, a proximal inlet portion 328 and an intermediate portion 330 extending between the proximal inlet portion 328 and the distal end 326. Intermediate portion 330 comprises a plurality of spines 304 and a plurality of frames 306. The spines 304 of intermediate portion 330 include a proximal-most spine 304A, an intermediate spine 304B and a distal-most spine 304C. The frames 306 of intermediate portion 330 include a proximal-most frame 306A, an intermediate frame 306B and a distal-most frame 306C. Ocular implant 300 is sized and configured so that the spines and frames are disposed in and supporting Schlemm's canal and the inlet 328 is disposed in the anterior chamber to provide for flow of aqueous humor from the anterior chamber through Schlemm's canal to outflow channels communicating with Schlemm's canal.

In FIG. 15, proximal-most spine 304A can be seen extending distally beyond proximal inlet portion 328. Proximal-most frame 306A comprises a first strut 308A and a second strut 308B that extend between proximal-most spine 304A and intermediate spine 304B. With reference to FIG. 15, it will be appreciated that intermediate frame 306B abuts a distal end of intermediate spine 304B. In the embodiment of FIG. 15, intermediate frame 306B comprises a third strut 308C and a fourth strut 308D that extend between intermediate spine 304B and distal-most spine 304C. Distal-most frame 306C can be seen extending between distal-most spine 304C and distal end 326 of ocular implant 300 in FIG. 15. Distal-most frame 306C comprises a fifth strut 308E and a sixth strut 308F.

Body 302 of ocular implant 300 defines a channel 332 that opens into a channel opening 334. With reference to FIG. 15, it will be appreciated that channel 332 and channel opening 334 extending together through body 302 across proximal-most spine 304A, intermediate spine 304B, distal-most spine 304C, proximal-most frame 306A, intermediate frame 306B, and distal-most frame 306C. Optional additional openings 310 communicating with channel 332 are disposed between the spines and are surrounded by the struts.

FIG. 16A is a plan view showing ocular implant 300 of FIG. 15. FIG. 16B is an enlarged section view taken along section line B-B shown in FIG. 16A. FIG. 16C is an additional enlarged section view taken along section line C-C shown in FIG. 16A. FIG. 16A, FIG. 16B and FIG. 16C may be collectively referred to as FIG. 16.

Ocular implant 300 of FIG. 16 comprises a body 302 that extends along a longitudinal central axis 320 which, in this view, lies in the plane of curvature of implant 300. Body 302 of ocular implant 300 has a distal end 326, a proximal inlet portion 328 and an intermediate portion 330 extending between the proximal inlet portion 328 and the distal end 326. Intermediate portion 330 comprises a plurality of spines 304 and a plurality of frames 306. The spines 304 of intermediate portion 330 include a proximal-most spine 304A, an intermediate spine 304B and a distal-most spine 304C. The frames 306 of intermediate portion 330 include a proximal-most frame 306A, an intermediate frame 306B and a distal-most frame 306C. As shown, unlike the embodiment of FIG. 8, in this embodiment the plane of curvature does not bisect the spines.

In FIG. 16, proximal-most spine 304A can be seen extending distally beyond proximal inlet portion 328. Proximal-most frame 306A comprises a first strut 308A and a second strut 308B that extend between proximal-most spine 304A and intermediate spine 304B. With reference to FIG. 16, it will be appreciated that intermediate frame 306B abuts a distal end of intermediate spine 304B. In the embodiment of FIG. 16, intermediate frame 306B comprises a third strut 308C and a fourth strut 308D that extend between intermediate spine 304B and distal-most spine 304C. Distal-most frame 306C can be seen extending between distal-most spine 304C and distal end 326 of ocular implant 300 in FIG. 16. Distal-most frame 306C comprises a fifth strut 308E and a sixth strut 308F.

Body 302 of ocular implant 300 defines a channel 332 that opens into a channel opening 334. With reference to FIG. 16, it will be appreciated that channel 332 and channel opening 334 extending together through body 302 across proximal-most spine 304A, intermediate spine 304B, distal-most spine 304C, proximal-most frame 306A, intermediate frame 306B, and distal-most frame 306C. In this embodiment, the struts on one side of the implant extend further out of the plane of curvature (shown as a dotted line in FIG. 16B) than their corresponding struts on the opposite side of the implant. Thus, as shown in FIG. 16B, strut 308F extends further out of the plane of curvature than its opposing strut 308E. It can also be seen from FIG. 16B that spine 304C extends further out of the plane of curvature on one side than on the other and that the struts 308E and 308F both extend circumferentially equally beyond the circumferential extend of spine 304C. Thus, implant 300 does not bend preferentially in the implant's plane of curvature.

Figure 17A:
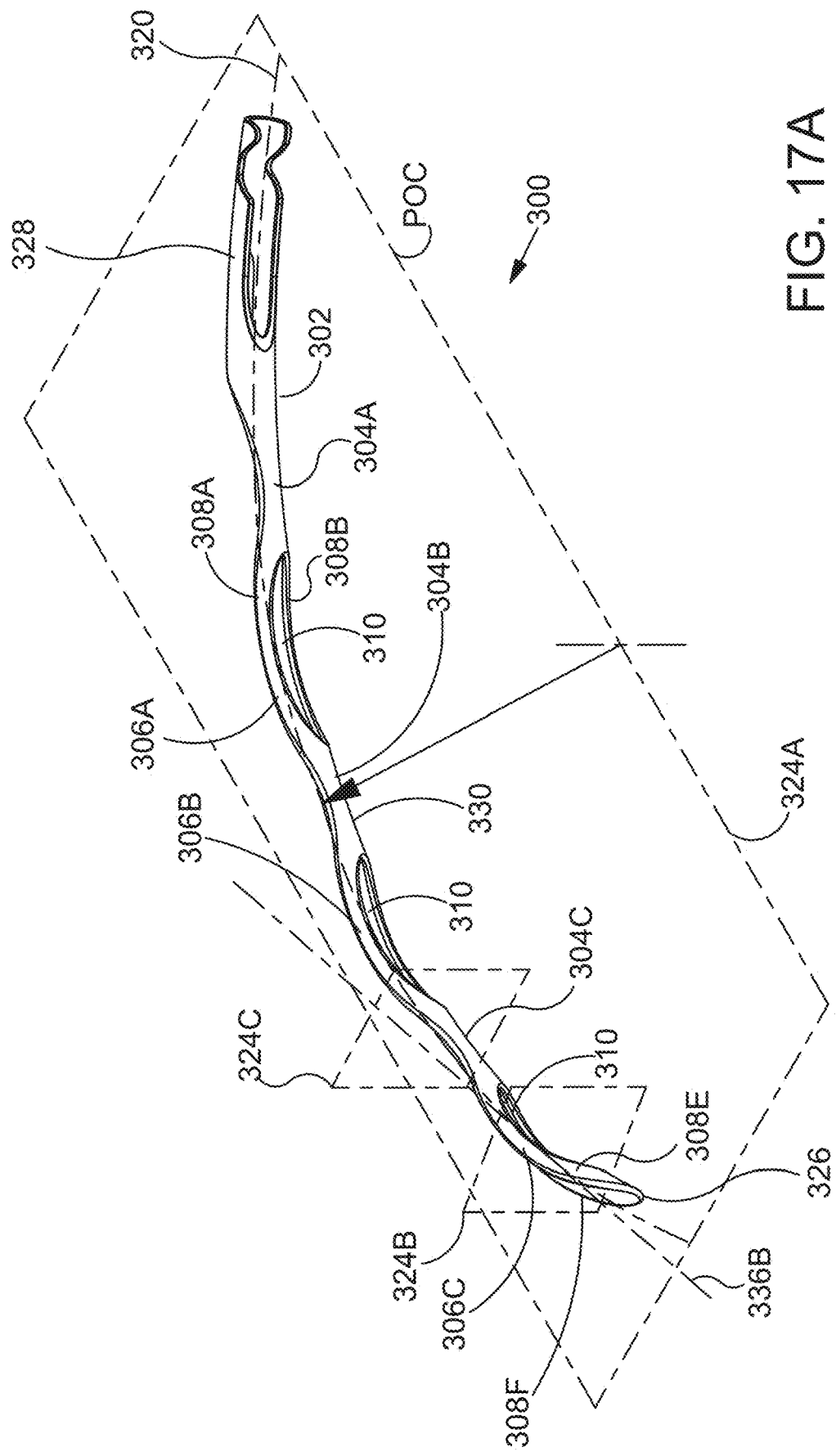
FIG. 17A is a perspective view showing the ocular implant of FIG. 15. A first, second and third planes are shown intersecting the ocular implant in FIG. 17A.

FIG. 17A is a perspective view showing ocular implant 300 of FIGS. 15 and 16. A first plane 324A is shown intersecting ocular implant 300 in FIG. 17A. Ocular implant 300 of FIG. 17A comprises a body 302 extending along a longitudinal central axis 320. In the embodiment of FIG. 17A, longitudinal central axis 320 follows a path that is generally curved such that longitudinal central axis 320 defines a plane of curvature POC.

In the embodiment of FIG. 17A, plane of curvature POC is co-planar with first plane 324A shown in FIG. 17A. With reference to FIG. 17A, it will be appreciated that plane of curvature POC would no longer be coplanar with first plane 324A if ocular implant 300 was rotated. In some methods in accordance with this detailed description, ocular implant 300 may be advanced into Schlemm's canal while the plane of curvature of the ocular implant is co-planar with a plane of curvature of Schlemm's canal.

A second plane 324B and a third plane 324C are shown extending transversely across body 302 of ocular implant 300 in FIG. 17A. With reference to FIG. 17A, it will be appreciated that third plane 324C extends through a distal-most spine 304C of ocular implant 300. Second plane 324B is shown extending through a distal-most frame 306C of ocular implant 300 in FIG. 17A. In the exemplary embodiment of FIG. 17A, second plane 324B is orthogonal to a reference line 336B. Reference line 336B is tangent to longitudinal central axis 320 and is shown lying on first plane 324A in FIG. 17A.

Body 302 of ocular implant 300 has a distal end 326, a proximal inlet portion 328 and an intermediate portion 330 extending between the proximal inlet portion 328 and the distal end 326. Intermediate portion 330 comprises a plurality of spines 304 and a plurality of frames 306. The frames 306 of intermediate portion 330 include a proximal-most frame 306A, an intermediate frame 306B and a distal-most frame 306C. Second plane 324B is shown extending through distal-most frame 306C in FIG. 17A. In the exemplary embodiment of FIG. 17A, body 302 includes a single intermediate frame 306B. It will be appreciated, however, that body 302 include any number of intermediate frames without deviating from the spirit and scope of the present detailed description.

The spines 304 of intermediate portion 330 include a proximal-most spine 304A, an intermediate spine 304B and a distal-most spine 304C. In FIG. 17A, third plane 324C is shown extending through distal-most spine 304C. In the exemplary embodiment of FIG. 17A, body 302 includes a single intermediate spine 304B. It will be appreciated, however, that body 302 include any number of intermediate spines without deviating from the spirit and scope of the present detailed description.

In FIG. 17A, proximal-most spine 304A can be seen extending distally beyond proximal inlet portion 328. Proximal-most frame 306A comprises a first strut 308A and a second strut 308B that extend between proximal-most spine 304A and intermediate spine 304B. With reference to FIG. 17, it will be appreciated that intermediate frame 306B abuts a distal end of intermediate spine 304B. In the embodiment of FIG. 17, intermediate frame 306B comprises a first strut and a second strut that extend between intermediate spine 304B and distal-most spine 304C. Distal-most frame 306C can be seen extending between distal-most spine 304C and distal end 326 of ocular implant 300 in FIG. 17. Distal-most frame 306C comprises a first strut 308E and a second strut 308F. Second plane 324B is shown extending through distal-most frame 306C in FIG. 17A.

Figure 17B:
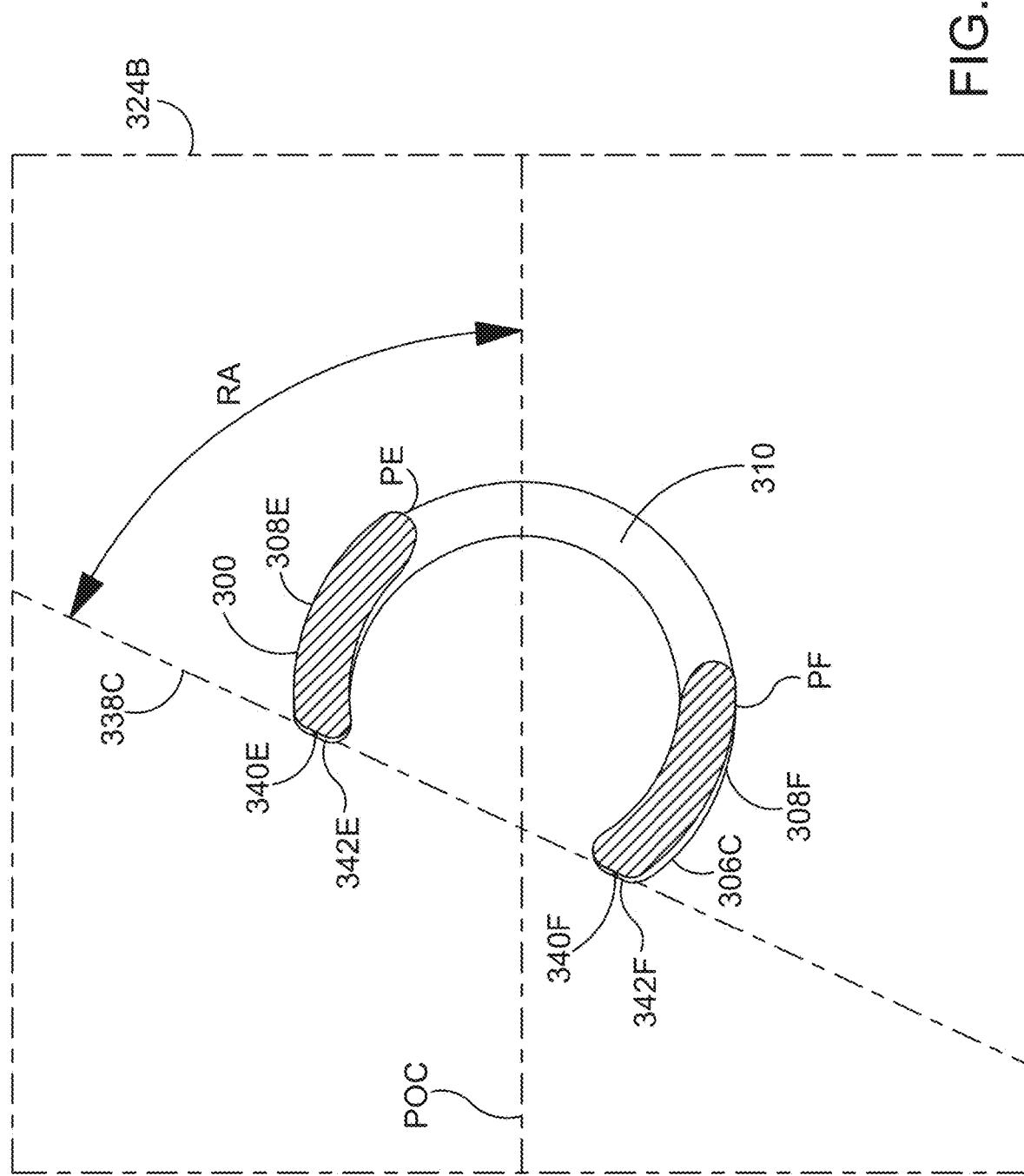
FIG. 17B is a plan view further illustrating the second plane shown in FIG. 17A.

FIG. 17B is an enlarged plan view of second plane 324B shown in FIG. 17A. With reference to FIG. 17A, it will be appreciated that second plane 324B intersects a first strut 308E and a second strut 308F of distal-most frame 306C. In FIG. 17B, a profile PE of first strut 308E is shown lying on second plane 324B. A profile PF of second strut 308F is also shown lying on second plane 324B in FIG. 17B. The profile of each strut is filled with a cross-hatch pattern in FIG. 17B.

In the embodiment of FIG. 17, the body of ocular implant 300 extends along a longitudinal central axis that is generally curved such that the longitudinal central axis defines a plane of curvature POC that is represented by a dashed line in FIG. 17B. A roll angle RA of distal-most frame 306C is illustrated using angular dimension lines in FIG. 17B. Roll angle RA extends between plane of curvature POC and a first footprint line 338C. In the exemplary embodiment of FIG. 17, first footprint line 338C is defined by a first point 340E and a second point 340F. First point 340E is disposed on a first landing surface 342E of first strut 308E. Second point 340F is disposed on a second landing surface 342F of second strut 308F.

Upon advancement of ocular implant 300 into Schlemm's canal, and depending on the angle of the delivery cannula with respect to the plane of Schlemm's canal during insertion, first landing surface 342E of first strut 308E and second landing surface 342F of second strut 308F may seat against the inner surface of the dome shaped wall that encloses the anterior chamber with the dome shaped wall providing normal forces supporting the landing surfaces. In some useful embodiments, roll angle RA is selected such that, when ocular implant 300 is advanced into Schlemm's canal landing surfaces of first strut 308E and second strut 308F are seated against the dome-shaped wall that defines the anterior chamber of the eye with substantially equal force. The decrease in the difference between the reaction forces on opposite sides of the implant will decrease any bending or twisting moments applied to implant 300 during insertion and advancement within Schlemm's canal.

FIG. 17C is an enlarged plan view of third plane 324C shown in FIG. 17A. As shown in FIG. 17A, third plane 324C intersects distal-most spine 304C. Accordingly, distal-most spine 304C is shown in cross-section in FIG. 17C. Distal-most spine 304C has a profile LC that is shown lying on third plane 324C in FIG. 17C.

In the embodiment of FIG. 17, the body of ocular implant 300 extends along a longitudinal central axis that is generally curved such that the longitudinal central axis defines a plane of curvature POC that is represented by a dashed line in FIG. 17C. Because the plane of curvature POC does not bisect spine 304C, spine 304C will not bend preferentially about POC.

Upon advancement of ocular implant 300 into Schlemm's canal, the landing surfaces may seat against the inner surface of the dome shaped wall that encloses the anterior chamber with the dome shaped wall providing normal forces supporting the landing surfaces. Each spine of ocular implant 300 may be configured to preferentially bend along a preferential bending plane. In some useful embodiments, each spine is rotationally offset relative to a first adjacent frame and a second adjacent frame by an angle selected such that the normal forces supporting the landing surfaces primarily or exclusively act to bend each spine along the preferential bending plane thereof. In some useful embodiments, each spine is rotationally offset relative to a first adjacent frame and a second adjacent frame by an angle selected such that a net twisting moment applied to each spine by the normal forces is substantially zero. The arrangement described above may minimize any twisting of the ocular implant body as the ocular implant is advanced into Schlemm's canal as part of a delivery procedure. This arrangement may also provide better trackability than devices that do not include these design features.

As shown in FIG. 17C, distal-most spine 304C of ocular implant 300 has a first lateral extent EF and a second lateral extent ES. In some useful embodiments, an aspect ratio of first lateral extent EF to second lateral extent ES is greater than about one. In some useful embodiments, the aspect ratio of first lateral extent EF to second lateral extent ES is greater than about three. The relationships described above may advantageously cause distal-most spine 304C to preferential bend more along one direction over another by, e.g., bending about the thinnest portion of the device.

With reference to FIG. 17C, it will be appreciated that distal-most spine 304C has a thickness T. In some useful embodiments, an aspect ratio of first lateral extent EF to thickness T may be selected such that distal-most spine 304C preferentially bends more along one direction over another. In some useful embodiments, an aspect ratio of first lateral extent EF to thickness T is greater than about one. In some useful embodiments, the aspect ratio of first lateral extent EF to thickness T is greater than about three.

FIG. 18A is an additional perspective view of ocular implant 300 shown in the previous figure. Ocular implant 300 of FIG. 18A includes a distal-most spine 304C and a distal-most frame 306C. In the exemplary embodiment of FIG. 18A, distal-most frame 306C comprises a first strut 308E and a second strut 308F. FIG. 18B is a stylized isometric view showing the profiles of distal-most spine 304C, first strut 308E and second strut 308F. The profile of distal-most spine 304C was created where a third plane 324C intersects ocular implant 300. Similarly, the profiles of first strut 308E and second strut 308F were created where a second plane 324B intersects ocular implant 300 in FIG. 18A.

The profiles of first strut 308E and second strut 308F are labeled PE and PF in FIG. 18B. The profile of distal-most spine 304C is labeled LC in FIG. 18B. With reference to those profiles, it will be appreciated that first strut 308E and second strut 308F comprise a first landing surface 342E and a second landing surface 342F, respectively. In FIG. 18B, a first normal force FE is represented by an arrow that is shown contacting first landing surface 342A. A second normal force FF is represented by an arrow that is shown contacting second landing surface 342A in FIG. 18.

Distal-most spine 304C of FIG. 18, is configured to preferentially bend in a preferential bending direction D shown in FIG. 18B. In some useful embodiments, ocular implant 300 is configured so that direction D extends at right angles to a point on a spherical surface that defines the anterior chamber when the landing surfaces of the ocular implant are seated against the dome-shaped wall that defines the anterior chamber. Also in some useful embodiments, ocular implant 300 is configured so that direction D extends at right angles to a point on a conical surface defined by ocular implant 300. With reference to FIG. 18, it will be appreciated that direction D is generally parallel to the directions of first normal force vector FE and second normal force vector FF.

In the embodiment of FIG. 18, first strut 308E, second strut 308F and distal-most spine 304C are configured such that, when ocular implant 300 is advanced along Schlemm's canal as part of a delivery procedure the landing surfaces of first strut 308E and second strut 308F will be seated against the dome-shaped wall defining the anterior chamber. When first landing surface 342A and second landing surface 342B contact the outer major wall of Schlemm's canal, the dome-shaped wall provides normal forces to support first strut 308E and second strut 308F. In the embodiment of FIG. 18, ocular implant 300 is configured such that normal forces applied to the landing surfaces of first strut 308E and second strut 308F primarily or exclusively act to bend first spine 304C along its preferential bending plane PBP. In some useful embodiments, each spine is rotationally offset relative to a first adjacent frame and a second adjacent frame by an angle selected such that the normal forces supporting the landing surfaces of the frames primarily or exclusively act to bend each spine along the preferential bending plane thereof. In some useful embodiments, each spine is rotationally offset relative to a first adjacent frame and a second adjacent frame by an angle selected such that a net twisting moment applied to each spine by the normal forces is substantially zero.

Figure 19A:
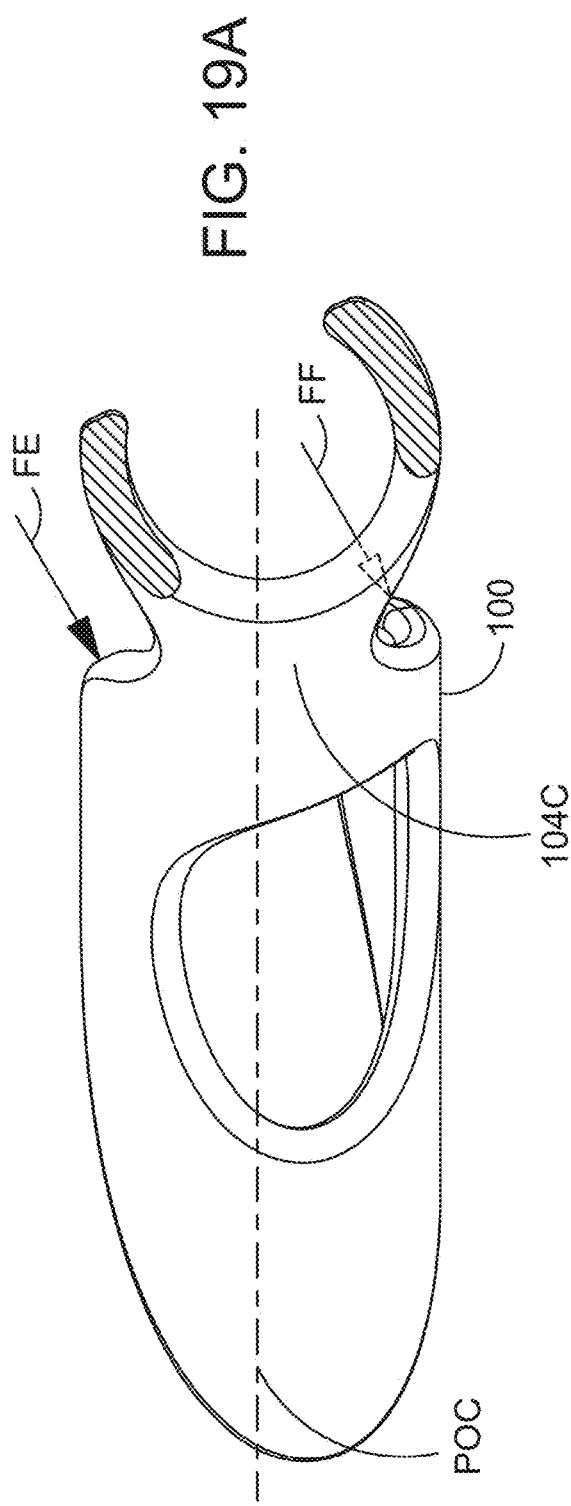
FIG. 19A and FIG. 19B are perspective views showing distal portions of the ocular implant of FIG. 8 and the ocular implant of FIG. 15, respectively.
Figure 19B:
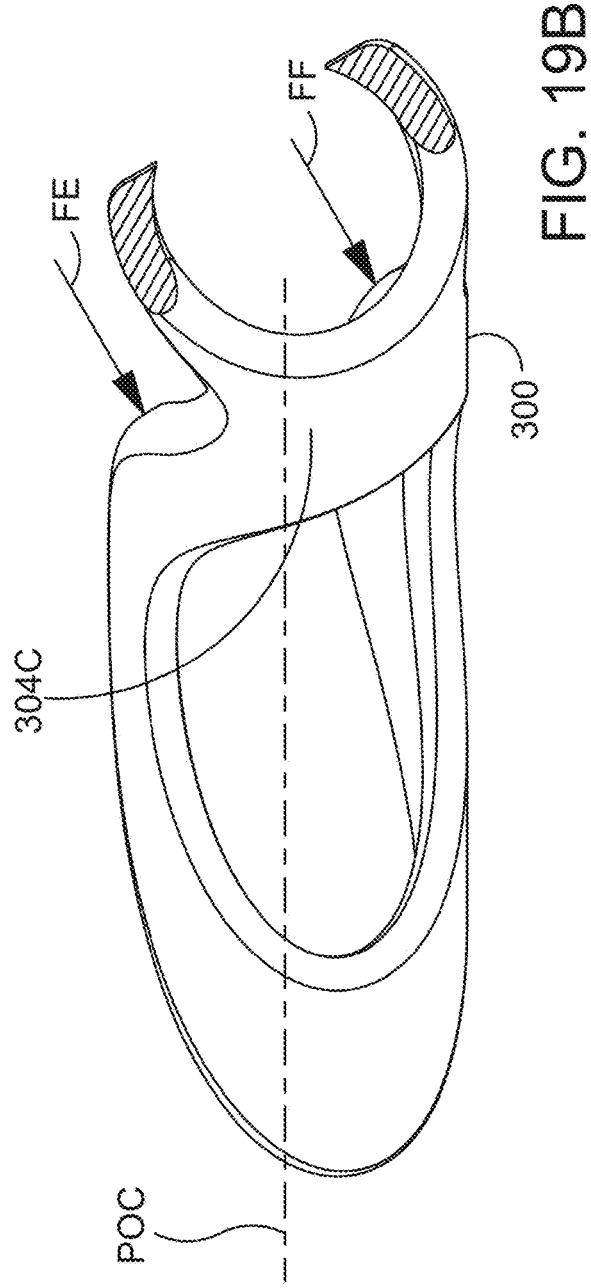

FIG. 19A and FIG. 19B are perspective views showing distal portions ocular implant 100 of FIG. 8 and ocular implant 300 of FIG. 15, respectively. FIG. 19A and FIG. 19B are presented on a single page so that second ocular implant 300 can be easily compared and contrasted to first ocular implant 100. FIG. 19A and FIG. 19B may be collectively referred to as FIG. 19. In FIG. 19, the body of each ocular implant extends along a longitudinal central axis that is generally curved such that the longitudinal central axis defines a plane of curvature POC. Each plane of curvature POC is represented by a dashed line in FIG. 19.

Ocular implant 100 includes a distal-most spine 104C, and ocular implant 300 includes a distal-most spine 304C.

As shown in FIG. 19A, plane of curvature POC bisects spine 104C. Spine 104C will bend preferentially about POC. In the embodiment of FIG. 19B, the plane of curvature POC does not bisect distal-most spine 304C of ocular implant 300. Spine 304C will not bend preferentially in plane POC.

In FIG. 19, two normal forces are shown acting on each ocular implant. A first normal force FE is represented by an arrow that is shown contacting a first landing surface of each ocular implant. A second normal force FF is represented by an arrow that is shown contacting second landing surface of each ocular implant. The arrows representing first normal force FE and second normal force FF are force vectors representing reaction forces provided by the dome-shaped wall of the eye. The dome-shaped wall of the eye provides support for the outer major wall of Schlemm's canal and the ocular implant during delivery. The support provided by the dome-shaped wall may be represented by the force vectors shown in FIG. 19. With reference to FIG. 19, it will be appreciated that direction D is generally parallel to the directions of first normal force vector FE and second normal force vector FF.

FIG. 20 is a perspective view showing an exemplary ocular implant 300 in accordance with this detailed description. Ocular implant 300 of FIG. 20 comprises a body 302 including a plurality of spines 304 and a plurality of frames 306. The frames 306 of body 302 include a first frame 306A, a second frame 306B and a third frame 306C.

First frame 306A comprises a first strut 308A and a second strut 308B. First strut 308A and second strut 308B comprise a first landing surface 342A and a second landing surface 342B, respectively. First landing surface 342A of first strut 308A and second landing surface 342B of second strut 308B define a first footprint line 338A. Second frame 306B comprises a first strut 308C and a second strut 308D. First strut 308C comprises a first landing surface 342C and second strut 308D comprises a second landing surface 342D. First landing surface 342C of first strut 308C and second landing surface 342D of fourth strut 308D define a second footprint line 338B. Third frame 306C includes a first strut 308E and a second strut 308F. First strut 308E and second strut 308F have a first landing surface 342E and a second landing surface 342F, respectively. First landing surface 342E of first strut 308E and second landing surface 342F of second strut 308F define a third footprint line 338C. In FIG. 20, first footprint line 338A, second footprint line 338B, and third footprint line 338C are shown intersecting at an apex 344 of a conical surface C.

Body 302 of ocular implant 300 has a distal end 326, a proximal inlet portion 328 and an intermediate portion 330 extending between proximal inlet portion 328 and distal end 326. Intermediate portion 330 of body 302 includes first frame 306A, second frame 306B, third frame 306C and a plurality of spines 304. The spines 304 of intermediate portion 330 include a first spine 304A, a second spine 304B and a third spine 304C. In FIG. 20, first frame 306A can be seen extending between first spine 304A and second spine 304B. With reference to FIG. 20, it will be appreciated that second frame 306B extends between second spine 304B and third spine 304C. In the embodiment of FIG. 20, third frame 306C extends between third spine 304C and distal end 326 of ocular implant 300 in FIG. 20.

In the embodiment of FIG. 20, each of first spine 304A, second spine 304B, and third spine 304C are configured to preferentially bend in a direction that is at right angles to conical surface C defined by first footprint line 338A, second footprint line 338B, and third footprint line 338C.

Figure 21:
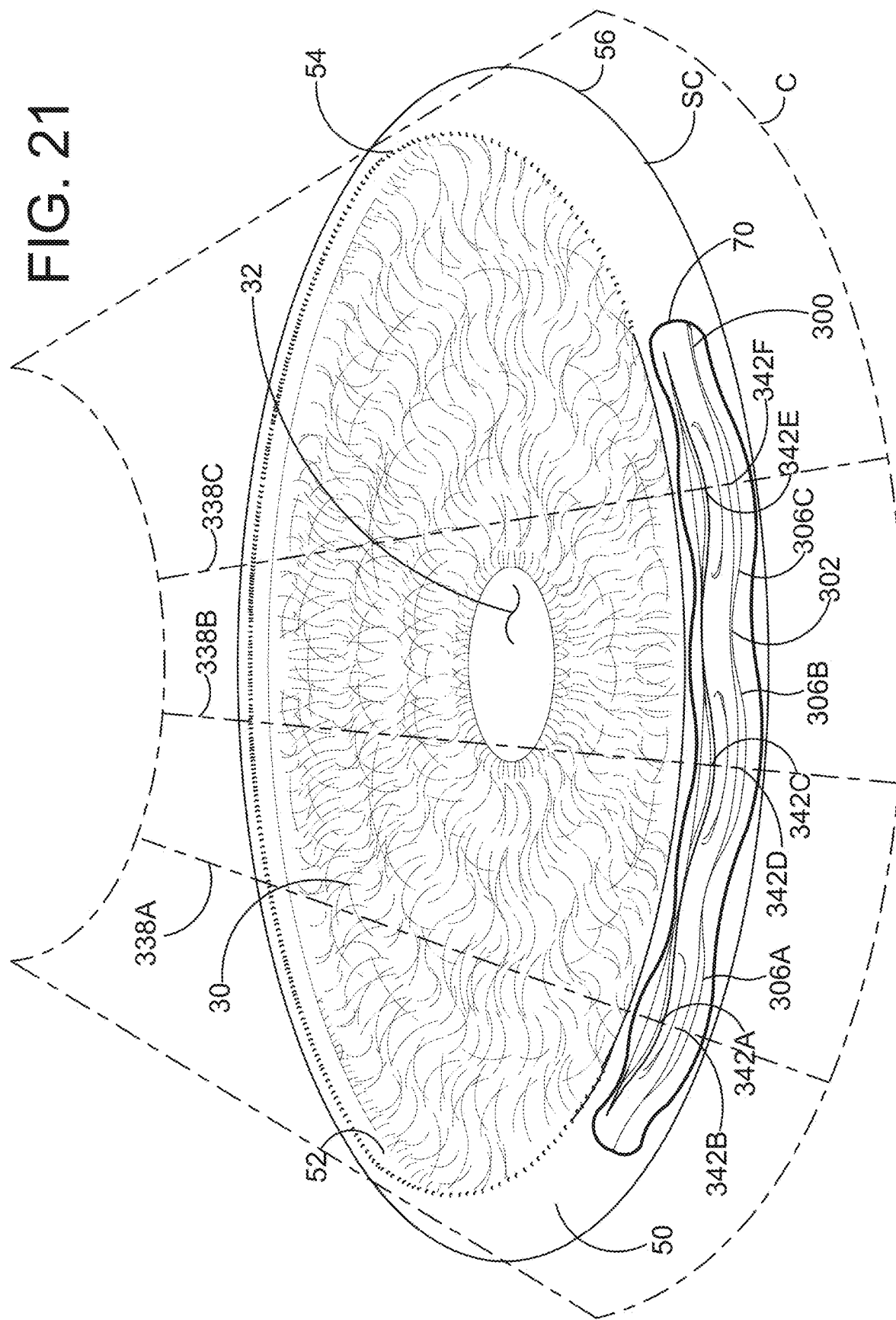
FIG. 21 is a stylized perspective view showing Schlemm's canal encircling an iris. For purposes of illustration, a window is cut through a first major side of Schlemm's canal in FIG. 21. Through the window, an ocular implant can be seen residing in a lumen defined by Schlemm's canal.

FIG. 21 is a stylized perspective view showing Schlemm's canal SC encircling an iris 30. With reference to FIG. 21, it will be appreciated that Schlemm's canal SC may overhang iris 30 slightly. Iris 30 defines a pupil 32. Schlemm's canal SC forms a ring around iris 30 with pupil 32 disposed in the center of that ring. With reference to FIG. 21, it will be appreciated that Schlemm's canal SC has a first major side 50, a second major side 52, a first minor side 54, and a second minor side 56. With reference to FIG. 21, it will be appreciated that first major side 50 is further from pupil 32 than second major side 52. In the exemplary embodiment of FIG. 21, first major side 50 is an outer major side of Schlemm's canal SC and second major side 52 is an inner major side of Schlemm's canal SC.

For purposes of illustration, a window 70 is cut through first major side 50 of Schlemm's canal SC in FIG. 21. Through window 70, an ocular implant can be seen residing in a lumen defined by Schlemm's canal. The ocular implant shown in FIG. 21 is ocular implant 300 shown in the previous figure. Ocular implant 300 comprises a body 302 including a plurality of spines and a plurality of frames 306. The frames 306 of body 302 include a first frame 306A, a second frame 306B and a third frame 306C. First frame 306A comprises a first landing surface 342A and a second landing surface 342B. First landing surface 342A and second landing surface 342B define a first footprint line 338A. Second frame 306B comprises a first landing surface 342C and a second landing surface 342D. First landing surface 342C and second landing surface 342D define a second footprint line 338B. Third frame 306C comprises a first landing surface 342E and a second landing surface 342F. First landing surface 342E and second landing surface 342F define a third footprint line 338C. In the embodiment of FIG. 21, first footprint line 338A, second footprint line 338B, and third footprint line 338C intersect at an apex of a conical surface C. Due to page size constraints, conical surface C is truncated in FIG. 21.

In the embodiment of FIG. 21, the landing surfaces of each frame are configured to seat against the outer major side 50 of Schlemm's canal SC. In the eye, the outer major side of Schlemm's canal is backed by scleral tissue. Accordingly, in the exemplary embodiment of FIG. 21, the landing surfaces of each frame will be seated against and supported by scleral tissue of the eye. Normal supporting forces will be applied to the landing surfaces of the struts by the scleral tissue. Applicant has created ocular implants designed to work in harmony with the dome shaped wall that defines the anterior chamber of the human eye. In some useful embodiments, the ocular implants are configured such that reaction forces applied to the ocular implant by scleral tissue while the ocular implant is being advanced into Schlemm's canal subject the ocular implant to pure bending with little or no twisting. The ocular implant may be configured such that a net twisting moment applied to each spine by the normal forces supporting the landing surfaces is substantially zero. The ocular implant may also be configured such that the normal forces supporting the landing surfaces primarily or exclusively act to bend each spine along the preferential bending plane thereof. In some useful embodiments, the preferential bending plane of each spine extends in a direction that is at right angles to a conical surface defined by the ocular implant.

While exemplary embodiments of the present invention have been shown and described, modifications may be made, and it is therefore intended in the appended claims to cover all such changes and modifications which fall within the true spirit and scope of the invention.

What is claimed is:

1. An ocular implant adapted to be disposed within Schlemm's canal of a human eye and configured to support Schlemm's canal in an open state, the ocular implant comprising:
    a body extending along a curved longitudinal central axis and configured to bend in a curvature plane, the body comprising a central channel, first and second frames and a spine interposed between the first and second frames, wherein the spine extends circumferentially from one side of the curvature plane and from an opposite side of the curvature plane, the body having dimensions adapted to be fit within Schlemm's canal;
    each frame comprising a first strut extending circumferentially on the one side of the curvature plane and a second strut extending circumferentially on the opposite side of the curvature plane, the first strut extending further out of the curvature plane than the corresponding second strut such that the first and second frames are not symmetric about the curvature plane.

2. The ocular implant of claim 1 wherein the body has a curved resting shape along the curvature plane.

3. The ocular implant of claim 1 wherein the spine comprises a first spine, the implant further comprising a third frame and a second spine interposed between the second and third frames, the third frame comprising a first strut on the one side of the curvature plane and a second strut on the opposite side of the curvature plane, the first strut of the third frame extending further out of the curvature plane than the corresponding second strut such that the third frame is not symmetric about the curvature plane.

4. The ocular implant of claim 3 wherein the first, second and third frames are substantially identical.

5. The ocular implant of claim 1 further comprising a first opening bordered by the first and second struts of the first frame and a second opening bordered by the first and second struts of the second frame, the first and second openings communicating with the central channel.

6. The ocular implant of claim 1 further comprising a channel opening bordered by circumferential extents of the spine and the first and second struts, the channel opening communicating with the central channel.

7. The ocular implant of claim 1 wherein the curvature plane bisects the spine.

8. An ocular implant adapted to be disposed within Schlemm's canal of a human eye and configured to support Schlemm's canal in an open state, the ocular implant comprising:
    a body extending along a curved longitudinal central axis and configured to bend in a curvature plane, the body comprising a central channel, first and second frames and a spine interposed between the first and second frames, wherein the spine extends circumferentially from one side of the curvature plane and from an opposite side of the curvature plane, the body having dimensions adapted to be fit within Schlemm's canal;
    each frame comprising a first strut extending circumferentially on the one side of the curvature plane to a first landing surface and a second strut extending circumferentially on the opposite side of the curvature plane to a second landing surface, a footprint line drawn between the first landing surface and the second landing surface of each of the first frame and the second frame defining a roll angle with respect to the curvature plane of other than 90 degrees.

9. The ocular implant of claim 8 wherein the body has a curved resting shape along the curvature plane.

10. The ocular implant of claim 8 wherein the spine comprises a first spine, the implant further comprising a third frame and a second spine interposed between the second and third frames, the third frame comprising a first strut on the one side of the curvature plane extending circumferentially on the one side of the curvature plane to a first landing surface and a second strut on the opposite side extending circumferentially on the opposite side of the curvature plane to a second landing surface, a footprint line drawn between the first landing surface and the second landing surface of the third frame defining a roll angle with respect to the curvature plane of other than 90 degrees.

11. The ocular implant of claim 10 wherein the first, second and third frames are substantially identical.

12. The ocular implant of claim 8 further comprising a first opening bordered by the first and second struts of the first frame and a second opening bordered by the first and second struts of the second frame, the first and second openings communicating with the central channel.

13. The ocular implant of claim 8 further comprising a channel opening bordered by circumferential extents of the spine and the landing surfaces of the first and second struts, the channel opening communicating with the central channel.

14. The ocular implant of claim 8 wherein the curvature plane bisects the spine.

* * * * *